United States Patent
Alley et al.

(10) Patent No.: US 10,858,376 B2
(45) Date of Patent: *Dec. 8, 2020

(54) TRICYCLIC BENZOXABOROLE COMPOUNDS AND USES THEREOF

(71) Applicants: GlaxoSmithKline Intellectual Property (No. 2) Limited, Brentford (GB); Anacor Pharmaceuticals, Inc., Palo Alto, CA (US)

(72) Inventors: Michael Richard Kevin Alley, Santa Clara, CA (US); Vincent S. Hernandez, Watsonville, CA (US); Jacob J. Plattner, Palo Alto, CA (US); Xianfeng Li, Cupertino, CA (US); David Barros-Aguirre, Madrid (ES); Ilaria Giordano, Hertfordshire (GB)

(73) Assignees: GlaxoSmithKline Intellectual Property (No.2) Limited, Brentford (GB); Anacor Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/695,253

(22) Filed: Nov. 26, 2019

(65) Prior Publication Data

US 2020/0095266 A1 Mar. 26, 2020

Related U.S. Application Data

(63) Continuation of application No. 16/385,547, filed on Apr. 16, 2019, now Pat. No. 10,526,352, which is a continuation of application No. 15/792,251, filed on Oct. 24, 2017, now Pat. No. 10,308,668, which is a continuation of application No. 14/387,384, filed as application No. PCT/US2014/050370 on Aug. 8, 2014, now abandoned.

(60) Provisional application No. 61/918,976, filed on Dec. 20, 2013, provisional application No. 61/864,496, filed on Aug. 9, 2013.

(51) Int. Cl.
  A61K 31/69 (2006.01)
  C07F 5/04 (2006.01)
  C07F 5/02 (2006.01)
  A61K 45/06 (2006.01)

(52) U.S. Cl.
  CPC ............ *C07F 5/04* (2013.01); *A61K 31/69* (2013.01); *A61K 45/06* (2013.01); *C07F 5/025* (2013.01)

(58) Field of Classification Search
  CPC .................................................... A61K 31/69
  See application file for complete search history.

(56) References Cited

U.S. PATENT DOCUMENTS

| | | | |
|---|---|---|---|
| 7,205,425 B2 | 4/2007 | Shibasaki et al. |
| 7,446,236 B2 | 11/2008 | Naud et al. |
| 7,816,344 B2 | 10/2010 | Baker et al. |
| 8,530,452 B2 | 9/2013 | Gordeev et al. |
| 8,703,742 B2 | 4/2014 | Hernandez et al. |
| 2009/0227541 A1 | 9/2009 | Baker et al. |
| 2010/0048570 A1 | 2/2010 | Kim et al. |
| 2012/0115813 A1 | 5/2012 | Hernandez et al. |
| 2013/0035501 A1 | 2/2013 | Conde et al. |
| 2013/0064783 A1 | 3/2013 | Baker et al. |
| 2013/0165411 A1 | 6/2013 | Gordeev et al. |
| 2016/0168167 A1 | 6/2016 | Kim et al. |

FOREIGN PATENT DOCUMENTS

| | | |
|---|---|---|
| WO | WO2006096131 | 9/2006 |
| WO | WO2008157726 | 12/2008 |
| WO | WO2011127143 | 10/2011 |
| WO | WO2012033858 | 3/2012 |
| WO | WO2013093615 | 6/2013 |
| WO | WO2015016558 | 2/2015 |
| WO | WO2015021396 | 2/2015 |

OTHER PUBLICATIONS

Adamczyk-Wozniak et al., "Benzoxaboroles—Old Compounds with new applications," J. Organometallic Chem., vol. 694, Issue 22, 2009, pp. 3533-3541.

(Continued)

*Primary Examiner* — Karen Cheng
(74) *Attorney, Agent, or Firm* — Dority & Manning, P.A.

(57) ABSTRACT

Compounds of Formula II,

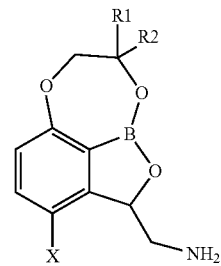

wherein X is selected from chloro, fluoro, bromo and iodo, $R^1$ and $R^2$ are each independently selected from H, —$CH_3$, —$CH_2CH_3$, —$CH_2CH_2CH_3$, or —$CH(CH_3)_2$; compositions containing them, their use in therapy, including their use as anti-mycobacterial agents, for example in the treatment of a mycobacterial infection in a mammal, and methods for the preparation of such compounds, are provided.

18 Claims, 4 Drawing Sheets

(56) References Cited

OTHER PUBLICATIONS

Canadian Office Action dated May 23, 2017 for Canadian Application No. 2,794,684.
English translation of Saudi Arabian Office Action, dated Jan. 11, 2017, for Saudi Arabian Application No. 516370551.
Hernandes et al., "Halogen Atoms in the Modern Medicinal Chemistry: Hints for the Drug Design," Current Drug Targets, vol. 11, No. 3, Mar. 2010, pp. 303-314.
King, "Bioisosteres, Conformational Restriction, and Pro-drugs—Case History: An Example of a Conformational Restriction Approach," Med Chem: Principle and Practice, Chapter 14, XP 002033086, 1994, pp. 206-208.
U.S. Office Action Related to U.S. Appl. No. 14/969,467 dated Jul. 19, 2017.
U.S. Office Action issued in U.S. Appl. No. 15/550,693, dated Mar. 19, 2018.
U.S. Office Action issued in U.S. Appl. No. 15/550,658, dated Jul. 6, 2018.
Vippagunta et al., "Crystalline solids," Elsevier Science B.V., Advanced Drugs Delivery Reviews 48 (2001), pp. 3-26.

US 10,858,376 B2

TRICYCLIC BENZOXABOROLE COMPOUNDS AND USES THEREOF

PRIORITY

This application is a continuation of and claims priority to U.S. application Ser. No. 16/385,547 filed Apr. 16, 2019, which is a continuation of and claims priority to U.S. application Ser. No. 15/792,251 filed Oct. 24, 2017, which is a continuation of and claims priority to U.S. application Ser. No. 14/387,384 filed Sep. 23, 2014 pursuant to 35 U.S.C. § 371 as a United States National Phase Application of International Patent Application Serial No. PCT/US2014/050370 filed Aug. 8, 2014, which claims priority to U.S. Provisional Application No. 61/864,496 filed Aug. 9, 2013 and U.S. Provisional Application No. 61/918,976 filed Dec. 20, 2013, and the entire contents of each of the foregoing applications are hereby incorporated by reference.

FIELD OF THE INVENTION

This invention relates to compounds, compositions containing them, their use in therapy, including their use as anti-mycobacterials, for example in the treatment of tuberculosis, and methods for the preparation of such compounds.

BACKGROUND OF THE INVENTION

*Mycobacterium* is a genus in the class of bacteria called Actinobacteria with its own distinct family known as Mycobacteriacae. *Mycobacterium* contains various obligate and opportunistic pathogens of animals, which may also be transmitted to humans and cause disease in humans, thus exhibiting a considerable zoonotic potential. During the past few decades, members of the *Mycobacterium avium-intracellulare* complex (MAIC) emerged as pathogens of human diseases, including lymphadenitis in children, pulmonary tuberculosis-like disease, and disseminated infections (occurring predominantly in immunocompromised persons, particularly AIDS patients). Similarly, important animal diseases result from infections in an animal by members of this group, e.g., avian tuberculosis and paratuberculosis in ruminants. MAIC includes *M. intracellulare* and 4 subspecies of *M. avium*, namely, *M. avium* subsp. *avium*, *M. avium* subsp. *hominissuis*, *M. avium* subsp. *silvaticum*, and *M. avium* subsp. *paratuberculosis*. Whereas members of the *M. tuberculosis* complex are transmitted by direct host contact, MAIC species are acquired predominantly from environmental sources, including soil, water, dust, and feed.

*Mycobacterium tuberculosis* (MTB) is a small aerobic non-motile high-GC bacillus with an "outer-membrane" that is unusually thick, "waxy," hydrophobic, rich in mycolic acids, and extremely impermeable, making mycobacterium infections difficult to treat. One third of the world's population is thought to be infected (including latent MTB), but this number increases to upwards of 80% of the population in many Asian and African countries. If untreated, the death rate from active MTB infections is more than 50%. In addition, the combination of HIV and MTB is deadly and increasing numbers of MTB strains are becoming resistant to standard of care drugs; approximately 300,000 new cases of multidrug resistant (MDR) *M. tuberculosis* are reported each year. Multidrug resistant (MDR) *M. tuberculosis* are resistant to isoniazid and rifampicin, and extensive drug resistant (XDR) *M. tuberculosis* are also resistant to at least one quinolone and one aminoglycoside. As can be seen in FIG. 1, XDR *M. tuberculosis* has been reported across much of the globe.

Add to these issues the ease of transmission, as shown in FIG. 2, the globalization of travel, and the ongoing relocation and emigration of many segments of the world's population and it is apparent that MTB is becoming a global crisis.

Synthetic drugs for treating tuberculosis (TB) have been available for over half a century, but incidences of the disease continue to rise world-wide. More than 2 billion people are currently infected with *M. tuberculosis*, most being latent cases, and it is estimated that over 9 million new cases occur each year, worldwide, resulting in from 1.7 to nearly 2 million deaths per year. In 2004 alone approximately 24,500 new infections and close to 5,500 deaths were recorded, each day. See Zignol, M et al., M. Surveillance of anti-tuberculosis drug resistance in the world: an updated analysis, 2007-2010. Bull. World Health Organ 2012, 90 (2), 111-119D) Co-infection with HIV is driving the increase in incidence (Williams, B. G.; Dye, C. Science, 2003, 301, 1535) and the cause of death in 31% of AIDS patients in Africa can be attributed to TB. See Corbett, E. L et al., Arch. Intl. Med., 2003, 163, 1009, Septkowitz, A et al., Clin. Microbiol. Rev. 1995, 8, 180).

The limitations of tuberculosis therapy and prevention are well known. The current available vaccine, BCG was introduced in 1921 and fails to protect most people past childhood. According to a 2006 report—"International Standards for Tuberculosis Care", a document developed by the Tuberculosis Coalition for Technical Assistance (TBCTA) which partners include Centers for Disease Control, American Thoracic Society, Tuberculosis Foundation, KNCV, the World Health Organization and the International Union Against Tuberculosis and Lung Disease—patients who do become infected with active disease currently endure two months of combination therapy with medicines introduced between 50 and 60 years ago—isoniazid (1952), rifampin (1963), pyrazinamide (1954) and ethambutol (1961)—followed by another 4 months of isoniazid and rifampin (also known as rifampicin). Alternatively the continuation phase could include Isoniazid and ethambutol for six months when adherence cannot be assessed, but according to this report, a longer continuation phase is associated with a higher rate of failure and relapse, especially in patients with HIV infection. Moreover, as detailed in this report, the doses of antituberculosis drugs used should conform to international recommendation and fixed-dose combinations of two (isoniazid and rifampicin), three (isoniazid, rifampicin, and pyrazinamide), and four (isoniazid, rifampicin, pyrazinamide, and ethambutol) drugs are highly recommended, especially when it is not possible to monitor the patient to ensure the treatment is ingested.

Daily dosing is required in these treatment phases and poor compliance drives the emergence and spread of multi-drug-resistant strains, which are challenging to treat. Shorter courses of more active agents which can be taken less frequently and which present a high barrier to the emergence of resistance, i.e. agents which are effective against multi-drug resistant strains of TB (MDR-TB), are urgently required. A March 2013 report (http://www.aidsmap.com/Once-weekly-continuation-phase-TB-treatment-equals-standard-of-care/page/2589498) suggests that a two-drug combination of rifapentine (a long-acting derivative of rifampicin) with moxifloxacin (a fluoroquinolone antibiotic that has not been used previously in TB treatment) can allow tuberculosis (TB) treatment to be taken once-weekly during the four-month continuation phase and achieves the same standard of care as the traditional continuation treatment of daily treatment with isoniazid and rifampin. Such a treatment phase would allow treatment supervision to extend throughout the continuation phase, increasing adherence. However, moxifloxacin is not yet approved for treatment of TB, and the once-weekly treatment protocol is not yet endorsed or approved as an alternative standard of care treatment—guideline panels at international and national levels will need to review the published evidence to determine if this alternative continuation treatment protocol should be recommended and adopted. In addition, rifapentine is expensive, and interactions between rifapentine and antiretroviral drugs in the non-nucleoside reverse transcriptase inhibitor (NNRTI) and protease inhibitor classes may prevent its use in TB patients who are also HIV positive and taking antiretroviral medicines. Thus, at present, the costs/benefits analysis of a continuation treatment with weekly rifapentine versus daily rifampicin is yet to be fully assessed.

The tuberculosis drug Sirturo™ (bedaquiline) was approved in the United States in late December 2012, and another, delamanid, is attempting to gain regulatory approval in the EU. However, both are reserved for drug-resistant tuberculosis, which accounts for just 5% of new cases. A 2007 Editorial and News Focus in Nature Medicine discusses many aspects of TB such as pathogenesis, epidemiology, drug discovery and vaccine development to date (*Nature Medicine,* 2007, *Focus on Tuberculosis,* Vol 13(3), pages 263-312), noting that 125 years after the anniversary of the discovery of *Mycobacterium tuberculosis,* more than one-third of people in the world are infected with *M. tuberculosis,* and of these, more than 1 in 10 will develop the disease known as tuberculosis, formerly known as consumption, in their lifetime.

When coupled with the emergence of multi-drug resistant strains of *Mycobacterium tuberculosis* (MDR-TB), the scale of the problem is amplified. The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. There is therefore a need to discover and develop new chemical entities to treat TB (recent leads are reviewed in: Grosset J H, Singer T G, Bishai W R. New Drugs for the Treatment of Tuberculosis: Hope and Reality. *Int J Tuberc Lung Dis.* 2012 August; 16(8):1005-14).

The present invention relates to tricyclic benzoxaborole compounds that show unexpected selectivity for inhibiting replication of *Mycobacterium tuberculosis* (*M. tuberculosis*) versus inhibition (toxicity) of human cells compared to other benzoxaborole compounds, and exhibit sub-micromolar MIC values against mycobacterium species, particularly *Mycobacterium tuberculosis* and *Mycobacterium tuberculosis* complex (MTC), *Mycobacterium avium* and *Mycobacterium avium* complex (MAC) and *Mycobacterium avium intracellulare* complex (MAIC). Generally speaking, a benzoxaborole has the following structure and substituent numbering system:

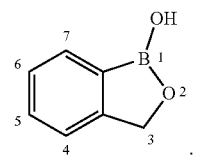

Certain benzoxaboroles which are substituted at position 7 form a tricyclic benzoxaborole compound. When the resulting tricyclic benzoxaborole is additionally substituted with a halogen substituent at position 4 and an aminomethyl substituent at position 3, such compounds are surprisingly selective towards and effective against mycobacteria including *M. tuberculosis*. The selectivity observed is assessed by comparing MIC values for such compounds relative to inhibition (toxicity) of these compounds to human cells, compared to other benzoxaborole compounds.

Boron-containing molecules such as benzoxaboroles that are useful as antimicrobials have been described previously, see e.g. "Benzoxaboroles—Old compounds with new applications" Adamczyk-Woźniak, A. et al., *Journal of Organometallic Chemistry* Volume 694, Issue 22, 15 Oct. 2009, Pages 3533-3541, and U.S. Pat. Pubs. US20060234981, US20070155699, US20090227541, WO2012033858, and US2013165411.

US20090227541 discloses a multitude of compounds, including two tricyclic benzoxaborole compounds with differing antibacterial activity against a panel of Gram negative bacteria (See e.g. Tables 1 and 2), but does not disclose tricyclic benzoxaborole compounds with halogen substitution on the benzoxaborole ring. WO2012033858 discloses benzoxaborole compounds with activity against *Mycobacterium tuberculosis,* including certain benzoxaborole compounds (see e.g. Examples 1.A through 1.V), but again, no tricyclic benzoxaborole compounds are disclosed with halogen substitution on the benzoxaborole ring. US2013165411 discloses tricyclic benzoxaborole compounds showing activity against *Acinetobacter baumannii, Pseudomonas aeruginosa, Escherichia coli* and *Klebsiella pneumoniae* (see Table 1), but notes specifically that the halogen-substituted tricyclic compounds investigated (Examples 17, 18 and 19) lack activity against *A. baumannii*, with MIC values ≥16 μg/μL antibacterial activity (see FIG. 1B).

SUMMARY OF THE INVENTION

The inventors have surprisingly found that tricyclic benzoxaborole compounds as described herein show unexpected selectivity for inhibiting replication of *Mycobacterium tuberculosis* (*M. tuberculosis*) versus inhibition (toxicity) of human cells compared to other benzoxaborole compounds. These tricyclic benzoxaborole compounds exhibit sub-micromolar MIC values against *M. tuberculosis,* which is comparable to or better than the MIC values for current therapies available for inhibiting *M. tuberculosis*. Further, in other embodiments, the tricyclic benzoxaborole compounds as described herein are envisioned for use in combination with current anti-tubercular compounds and are envisioned to achieve greater efficacy in treating animals, including humans, infected with *M. tuberculosis*.

Resistance remains an issue in the treatment of tuberculosis (TB) and one clinical strategy is to focus on early combination with other TB drugs and to expedite early assessment of the compound's efficacy in patients. Compounds of Formula II or Formula IIa offer a unique opportunity to address the serious issues which arise during the treatment of TB, such as multi-drug resistance, extensive-drug resistance, reactivity and/or adverse interaction between therapeutic agents in a multi-drug combination, and treatment length, thereby addressing potential patient needs.

In certain embodiments of the present invention there is featured combinations of anti-tuberculosis agents and certain tricyclic benzoxaboroles, for use in the treatment of *Mycobacterium tuberculosis* infections in animals, including humans. In particular embodiments, such tricyclic benzoxaboroles are used, in combination with other know anti-tuberculosis agents, for treating an animal subject with a *Mycobacterium tuberculosis* infection, particularly in an animal subject that is additionally infected with a human retrovirus, in particular a human immunodeficiency virus (HIV).

In an exemplary embodiment, the invention is a compound as described herein, or a pharmaceutically acceptable salt thereof.

In particular embodiments, the tricyclic benzoxaborole is a compound or a salt thereof, including a pharmaceutically acceptable salt thereof, having a structure according to Formula II:

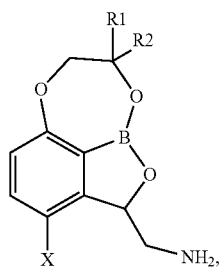

Formula II wherein X is selected from chloro, fluoro, bromo and iodo; $R^1$ and $R^2$ are each independently selected from H, —$CH_3$, —$CH_2CH_3$, —$CH_2CH_2CH_3$, and —$CH(CH_3)_2$.

In particular embodiments there is provided a compound of Formula II or a salt thereof, wherein X is chloro or bromo; $R^1$ and $R^2$ are each independently selected from H, —$CH_3$, —$CH_2CH_3$, —$CH_2CH_2CH_3$, and —$CH(CH_3)_2$.

In particular embodiments there is provided a compound of Formula II or a salt thereof, wherein X is fluoro, $R^1$ and $R^2$ are as described herein.

In particular embodiments there is provided a compound of Formula II or a salt thereof, wherein X is chloro, $R^1$ and $R^2$ are as described herein.

In particular embodiments there is provided a compound of Formula II or a salt thereof, wherein X is bromo, $R^1$ and $R^2$ are as described herein.

In particular embodiments there is provided a compound of Formula II or a salt thereof, wherein X is iodo, $R^1$ and $R^2$ are as described herein.

In particular embodiments there is provided a compound of Formula II or a salt thereof, wherein X is chloro or bromo, $R^1$ and $R^2$ are each independently selected from H, —$CH_3$, and —$CH_2CH_3$.

In particular embodiments there is provided a compound of Formula II or a salt thereof, wherein X is chloro or bromo, $R^1$ and $R^2$ are each independently selected from H and —$CH_3$.

In particular embodiments there is provided a compound of Formula II or a salt thereof, wherein X is fluoro or iodo, $R^1$ and $R^2$ are each independently selected from H and —$CH_3$.

In particular embodiments there is provided a compound of Formula IIa

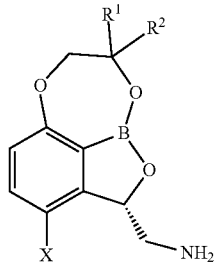

Formula IIa wherein X is fluoro, chloro, bromo or iodo, and $R^1$ and $R^2$ are each independently selected from H, —$CH_3$, —$CH_2CH_3$, —$CH_2CH_2CH_3$, and —$CH(CH_3)_2$, or a salt thereof, including a pharmaceutically acceptable salt thereof.

In particular embodiments there is provided a compound of Formula IIa wherein X is fluoro, chloro, bromo or iodo and $R^1$ and $R^2$ are each independently selected from H, —$CH_3$, and —$CH_2CH_3$, or a salt thereof, including a pharmaceutically acceptable salt thereof.

In particular embodiments there is provided a compound of Formula IIa wherein X is fluoro, chloro, bromo or iodo and $R^1$ and $R^2$ are each independently selected from H and —$CH_3$, or a salt thereof, including a pharmaceutically acceptable salt thereof.

In particular embodiments there is provided a compound of Formula IIa or a salt thereof, wherein X is fluoro, and $R^1$ and $R^2$ are as described herein.

In particular embodiments there is provided a compound of Formula IIa or a salt thereof, wherein X is chloro, and $R^1$ and $R^2$ are as described herein.

In particular embodiments there is provided a compound of Formula IIa or a salt thereof, wherein X is bromo, and $R^1$ and $R^2$ are as described herein.

In particular embodiments there is provided a compound of Formula IIa or a salt thereof, wherein X is iodo, and $R^1$ and $R^2$ are as described herein.

In particular embodiments there is provided a compound of Formula IIa wherein X is chloro or bromo and $R^1$ and $R^2$ are each independently selected from H, —$CH_3$, —$CH_2CH_3$, —$CH_2CH_2CH_3$, and —$CH(CH_3)_2$, or a salt thereof, including a pharmaceutically acceptable salt thereof.

In particular embodiments there is provided a compound of Formula IIa wherein X is chloro or bromo, and $R^1$ and $R^2$ are each independently selected from H, —$CH_3$, and —$CH_2CH_3$, or a salt thereof, including a pharmaceutically acceptable salt thereof.

In particular embodiments there is provided a compound of Formula IIa wherein X is chloro or bromo, and $R^1$ and $R^2$ are each independently selected from H and —$CH_3$, or a salt thereof, including a pharmaceutically acceptable salt thereof.

In particular embodiments, the tricyclic benzoxaborole is a compound of Formula II as indicated below:

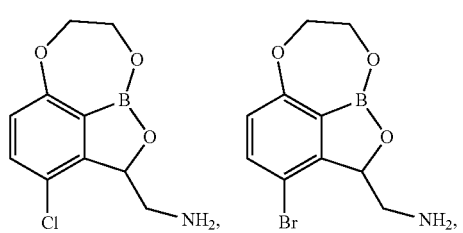
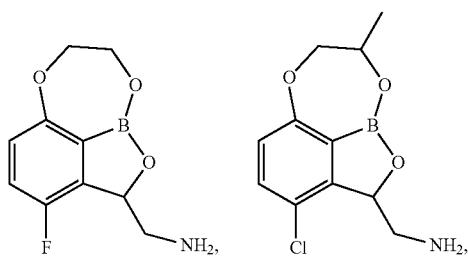
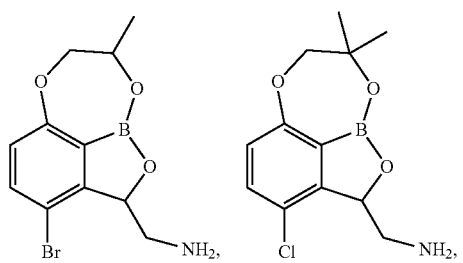
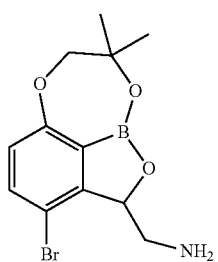

or a pharmaceutically acceptable salt thereof.

In particular embodiments, the tricyclic benzoxaborole is a compound of Formula IIa as indicated below:

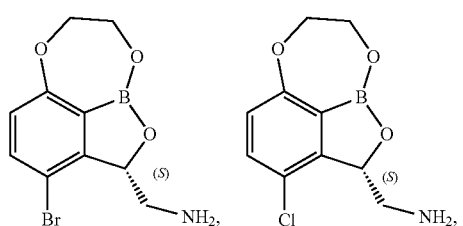
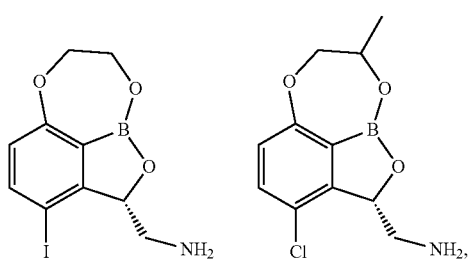

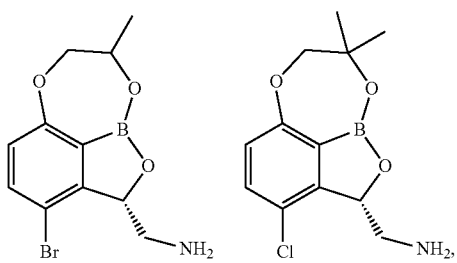
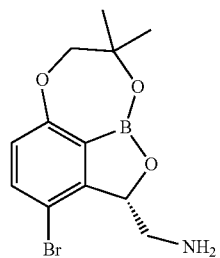

or a pharmaceutically acceptable salt thereof.

In other embodiments, the tricyclic benzoxaborole is a compound of Formula II as indicated below:

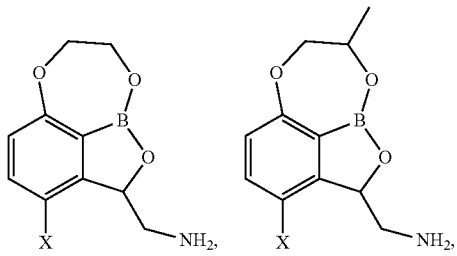
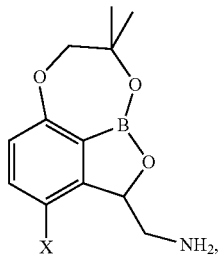

wherein X is as defined herein, or a pharmaceutically acceptable salt thereof.

In other embodiments, the tricyclic benzoxaborole is a compound of Formula IIa as indicated below:

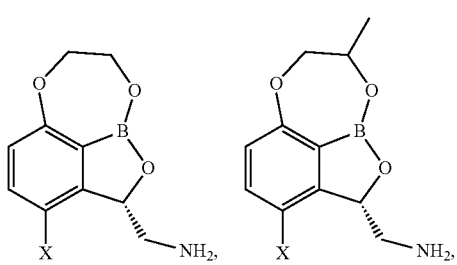

-continued

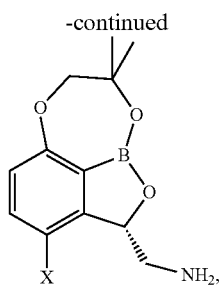

wherein X is as defined herein, or a pharmaceutically acceptable salt thereof.

In still other embodiments, the tricyclic benzoxaborole is a compound of Formula II as indicated below:

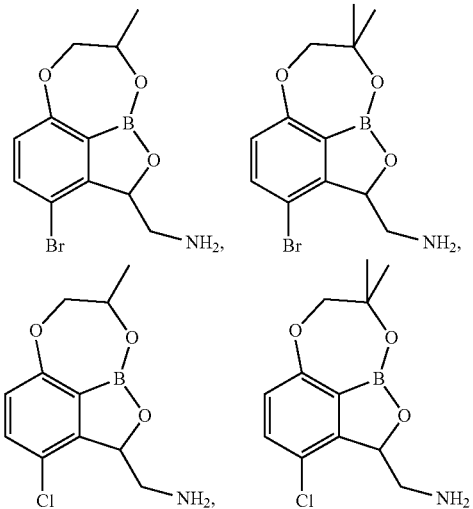

and a pharmaceutically acceptable salt thereof.

In still other embodiments, the tricyclic benzoxaborole is a compound of Formula IIa as indicated below:

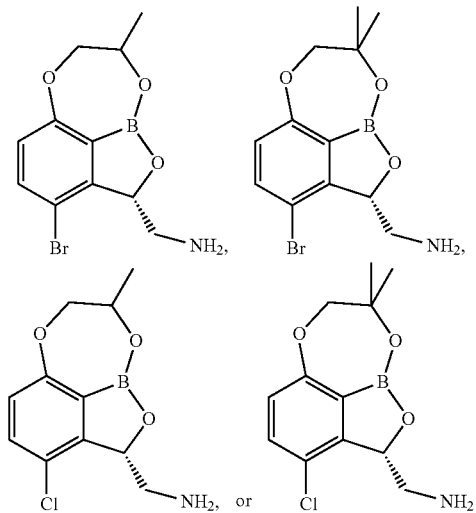

or a pharmaceutically acceptable salt thereof.

In another embodiment there is provided a compound, (S)-(3-chloro-7,8-dihydro-2H-1,6,9-trioxa-9a-borabenzo[cd]azulen-2-yl)methanamine, having the formula:

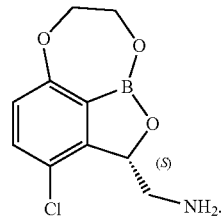

In another embodiment there is provided a compound, (S)-(3-chloro-7,8-dihydro-2H-1,6,9-trioxa-9a-borabenzo[cd]azulen-2-yl)methanamine, having the formula:

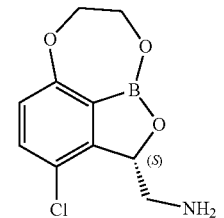

or a pharmaceutically acceptable salt thereof.

Another embodiments provides a pharmaceutically acceptable salt of a compound, (S)-(3-chloro-7, 8-dihydro-2H-1,6,9-trioxa-9a-borabenzo[cd]azulen-2-yl)methanamine, having the formula:

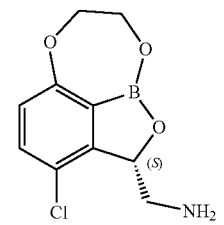

Another embodiment provides a pharmaceutical composition comprising a compound, (S)-(3-chloro-7, 8-dihydro-2H-1,6, 9-trioxa-9a-borabenzo[cd]azulen-2-yl)methanamine, having the formula:

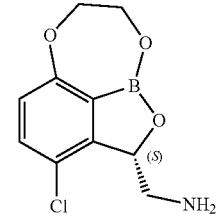

together with at least one pharmaceutically acceptable excipient.

In yet another embodiment there is provided a compound, (S)-(3-bromo-8,8-dimethyl-7,8-dihydro-2H-1,6,9-trioxa-9a-borabenzo[cd]azulen-2-yl)methanamine, having the formula:

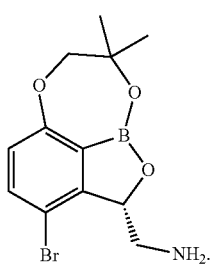 [SMILES: CC1(C)COc2ccc(Br)c3c2B(O[C@@H]3CN)O1]

Still another embodiment provides a compound, (S)-(3-bromo-8,8-dimethyl-7,8-dihydro-2H-1,6,9-trioxa-9a-borabenzo[cd]azulen-2-yl)methanamine, having the formula:

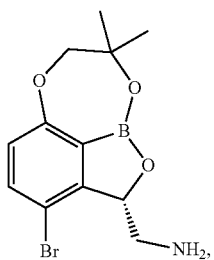 [SMILES: CC1(C)COc2ccc(Br)c3c2B(O[C@@H]3CN)O1]

or a pharmaceutically acceptable salt thereof.

Another embodiment provides a pharmaceutically acceptable salt of a compound, (S)-(3-bromo-8,8-dimethyl-7,8-dihydro-2H-1,6,9-trioxa-9a-borabenzo[cd]azulen-2-yl)methanamine, having the formula:

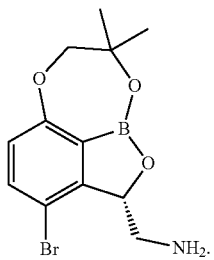 [SMILES: CC1(C)COc2ccc(Br)c3c2B(O[C@@H]3CN)O1]

Another embodiment provides a pharmaceutical composition comprising a compound, (S)-(3-bromo-8, 8-di methyl-7, 8-dihydro-2H-1,6,9-trioxa-9a-borabenzo[cd]azulen-2-yl)methanamine, having the formula:

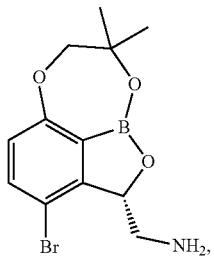 [SMILES: CC1(C)COc2ccc(Br)c3c2B(O[C@@H]3CN)O1]

together with at least one pharmaceutically acceptable excipient.

One embodiment provides a compound of Formula II or Formula IIa or a salt thereof, which is:

(3-bromo-7,8-dihydro-2H-1,6,9-trioxa-9a-borabenzo[cd]azulen-2-yl)methanamine;
(S)-(3-bromo-7,8-dihydro-2H-1,6,9-trioxa-9a-borabenzo[cd]azulen-2-yl)methanamine;
(3-chloro-7,8-dihydro-2H-1,6,9-trioxa-9a-borabenzo[cd]azulen-2-yl)methanamine;
(S)-(3-chloro-7,8-dihydro-2H-1,6,9-trioxa-9a-borabenzo[cd]azulen-2-yl)methanamine;
(3-chloro-8-methyl-7,8-dihydro-2H-1,6,9-trioxa-9a-borabenzo[cd]azulen-2-yl)methanamine;
(3-bromo-8-methyl-7,8-dihydro-2H-1,6,9-trioxa-9a-borabenzo[cd]azulen-2-yl)methanamine;
(3-bromo-8,8-dimethyl-7,8-dihydro-2H-1,6,9-trioxa-9a-borabenzo[cd]azulen-2-yl)methanamine;
(S)-(3-bromo-8,8-dimethyl-7,8-dihydro-2H-1,6,9-trioxa-9a-borabenzo[cd]azulen-2-yl)methanamine;
(3-chloro-8,8-dimethyl-7,8-dihydro-2H-1,6,9-trioxa-9a-borabenzo[cd]azulen-2-yl)methanamine;
(S)-(3-chloro-8,8-dimethyl-7,8-dihydro-2H-1,6,9-trioxa-9a-borabenzo[cd]azulen-2-yl)methanamine;
(3-fluoro-7,8-dihydro-2H-1,6,9-trioxa-9a-borabenzo[cd]azulen-2-yl)methanamine; or
(S)-(3-iodo-7,8-dihydro-2H-1,6,9-trioxa-9a-borabenzo[cd]azulen-2-yl)methanamine.

In a related embodiment, the pharmaceutically acceptable salt is selected from hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like. In other related embodiments, the pharmaceutically acceptable salt is derived from organic acids including acetic acid, propionic acid, isobutyric acid, maleic acid, malonic acid, benzoic acid, succinic acid, suberic acid, fumaric acid, glucaronic acid, galacturonic acid, lactic acid, mandelic acid, phthalic acid, benzenesulfonic acid, p-tolylsulfonic acid, citric acid, tartaric acid, methanesulfonic acid, and the like. Still other related embodiments the pharmaceutically acceptable salt includes salts of amino acids such as arginate, lysinate and the like.

In particular aspects of the invention, the compound of Formula II or Formula IIa is a mixture of diastereomers. In other particular aspects of the invention, the compound of Formula II or Formula IIa is a diastereomer. In other particular aspects of the invention, the compound of Formula II is a racemic mixture of enantiomers. In still other particular aspects of the invention, the compound of Formula II is a specific enantiomer. In particular aspects of the invention when $R^1$ and $R^2$ are both H or $CH_3$, the compound of Formula II or Formula IIa has (S) stereochemistry at the chiral center. One embodiment provides a combination comprising: a first therapeutic agent wherein the first therapeutic agent is a compound as described herein, or a pharmaceutically acceptable salt thereof; optionally a second therapeutic agent; optionally a third therapeutic agent; optionally a fourth therapeutic agent; optionally a fifth therapeutic agent; and optionally a sixth therapeutic agent.

A related embodiment provides a combination as described wherein the optional second, third, fourth, fifth and sixth therapeutic agent is independently selected from isoniazid, rifampin, pyrazinamide, ethambutol, moxifloxacin, rifapentine, clofazimine, bedaquiline (TMC207), nitroimidazo-oxazine PA-824, delamanid (OPC-67683), an oxazolidinone such as linezolid, tedizolid, radezolid, sutezolid (PNU-100480), or posizolid (AZD-5847), EMB analogue SQ109, a benzothiazinone, a dinitrobenzamide or an antiviral agent including an antiretroviral agent.

A related embodiment provides a combination as described wherein the antiretroviral agents is zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

Another embodiment of the invention provides a combination as described wherein the second, third, fourth, fifth and sixth therapeutic agent is selected from a therapeutic agent approved or recommended for the treatment of tuberculosis.

One embodiment of the present invention provides a pharmaceutical formulation comprising a first therapeutic agent, said first therapeutic agent being a therapeutically effective amount of a compound of Formula II or Formula IIa according to any of the embodiments described herein or a pharmaceutically acceptable salt thereof. A related embodiment provides a combination as described herein and a pharmaceutically acceptable excipient, adjuvant or diluent. In another embodiment, the pharmaceutical formulation may further comprise a second therapeutic agent.

Another embodiment provides a method of killing mycobacteria and/or inhibiting replication of mycobacteria that causes disease in an animal, comprising contacting the mycobacteria with an effective amount of a compound of Formula II or Formula IIa as described herein or a pharmaceutically acceptable salt thereof, so as to kill the mycobacteria and/or prevent the replication of the mycobacteria.

Another embodiment of the invention provides a method of treating a mycobacterium infection in an animal comprising: administering to the animal any one of: (i) a therapeutically effective amount of a compound of Formula II or Formula IIa as described herein or a pharmaceutically acceptable salt thereof; (ii) a therapeutically effective amount of a combination comprising a compound of Formula II or Formula IIa as described herein or a pharmaceutically acceptable salt thereof; or (iii) a therapeutically effective amount of a pharmaceutical formulation comprising a compound of Formula II or Formula IIa as described herein or a pharmaceutically acceptable salt thereof, so as to treat the mycobacterium infection in the animal.

In a further aspect, the invention provides a method of killing mycobacteria and/or inhibiting replication of mycobactera or a method of treating a mycobacterial infection in an animal such as livestock and pets, including cattle sheep, goats, dogs and cats, or a human, including an immune-suppressed human said method comprising: contacting the mycobactera with an effective amount of a compound of Formula II or Formula IIa as described herein, thereby killing the mycobacteria and/or inhibiting replication of the mycobacteria, or said method comprising administering to the animal with the mycobacterial infection a therapeutically effective amount of a compound of Formula II or a compound of Formula IIa, or a pharmaceutically acceptable salt thereof. In an exemplary embodiment, the compound of Formula II or compound of Formula IIa is part of a pharmaceutical formulation described herein. In another exemplary embodiment, the contacting occurs under conditions which permit entry of the combination into the mycobacterium.

Another embodiment of the invention provides a method as described herein, wherein the mycobacteria is selected from *Mycobacterium tuberculosis, Mycobacterium avium* including subspecies (subsp.) *Mycobacterium avium* subsp. *avium, Mycobacterium avium* subsp. *hominissuis, Mycobacterium avium* subsp. *silvaticum,* and *Mycobacterium avium* subsp. *paratuberculosis; Mycobacterium kansasii, Mycobacterium malmoense, Mycobacterium simiae, Mycobacterium szulgai, Mycobacterium xenopi, Mycobacterium scrofulaceum, Mycobacterium abscessus, Mycobacterium chelonae, Mycobacterium haemophilum, Mycobacterium leprae, Mycobacterium marinum, Mycobacterium fortuitum, Mycobacterium parafortuitum, Mycobacterium gordonae, Mycobacterium vaccae, Mycobacterium bovis, Mycobacterium bovis* BCG, *Mycobacterium africanum, Mycobacterium canetti, Mycobacterium caprae, Mycobacterium microti, Mycobacterium pinnipedi, Mycobacterium leprae, Mycobacterium ulcerans, Mycobacterium intracellulare, Mycobacterium tuberculosis* complex. (MTC), *Mycobacterium avium* complex (MAC), *Mycobacterium avian-intracellulare* complex (MAIC), *Mycobacterium gordonae* clade; *Mycobacterium kansasii* clade; *Mycobacterium chelonae* clade; *Mycobacterium fortuitum* clade; *Mycobacterium parafortuitum* clade; and *Mycobacterium vaccae* clade.

Another embodiment provides a method of treating a mycobacterium infection in an animal comprising: administering to the animal any one of: (i) a therapeutically effective amount of a compound of Formula II or Formula IIa as described herein or a pharmaceutically acceptable salt thereof; (ii) a therapeutically effective amount of a combination comprising a compound of Formula II or Formula IIa as described herein or a pharmaceutically acceptable salt thereof; or (iii) a therapeutically effective amount of a pharmaceutical formulation comprising a compound of Formula II or Formula IIa as described herein or a pharmaceutically acceptable salt thereof, so as to treat the mycobacterium infection in the animal, wherein the mycobacterium infection is a *M. tuberculosis* infection.

Another embodiment provides a compound of Formula II or Formula IIa as described herein or a pharmaceutically acceptable salt thereof, for use in the treatment of a disease resulting from a mycobacterial infection in an animal, including a human. Another embodiment provides a compound as described herein, wherein the disease is selected from tuberculosis, leprosy, Johne's disease, Buruli or Bairnsdale ulcer, Crohn's disease, pulmonary disease or pulmonary infection. pneumonia, bursa, synovial, tendon sheaths, localized abscess, lymphadenitis, skin and soft tissue infections Lady Windermere syndrome, MAC lung disease, disseminated *Mycobacterium avium* complex (DMAC), disseminated *Mycobacterium avium intracellulare* complex (DMAIC), hot-tub lung, MAC mastitis, MAC pyomyositis, *Mycobacterium avum paratuberculosis*, or granuloma, disease.

One embodiment provides the use of a compound of Formula II or Formula IIa as described herein or a pharmaceutically acceptable salt thereof in the manufacture of a medicament for the treatment of mycobacterial infection in an animal.

Another embodiment provides a method of treating a disease resulting from a mycobacterial infection in an animal, particularly in a mammal, more particularly in a human, which method comprises administering to the animal in need of such treatment an effective amount of a compound Formula II as described herein or a pharmaceutically acceptable salt thereof. Another embodiment provides a method as described, wherein the disease is selected from tuberculosis, leprosy, Johne's disease, Buruli or Bairnsdale ulcer, Crohn's disease, pulmonary disease or pulmonary infection. pneumonia, bursa, synovial, tendon sheaths, localized abscess, lymphadenitis, skin and soft tissue infections Lady Windermere syndrome, MAC lung disease, disseminated *Mycobacterium avium* complex (DMAC), disseminated *Mycobacterium avium intracellulare* complex (DMAIC), hot-tub lung, MAC mastitis, MAC pyomyositis, *Mycobacterium* avum *paratuberculosis*, or granuloma disease.

Another embodiment provides a method of treating a mycobacterial infection in an animal, particularly in a mammal, which method comprises administering to the animal in need of such treatment a therapeutically effective amount of a compound described herein, or pharmaceutically acceptable salt thereof. Another embodiment provides a method of treating a mycobacterial infection in an animal, particularly a mammal, wherein the mycobacterial infection is *Mycobacterium tuberculosis*.

In one embodiment there is provided a pharmaceutical formulation comprising a first therapeutic agent, said first therapeutic agent being a therapeutically effective amount of a compound described herein or pharmaceutically acceptable salt thereof, and a pharmaceutically acceptable excipient, adjuvant or diluent.

More particularly, a pharmaceutical formulation is provided comprising a first therapeutic agent that is a compound of Formula II or Formula IIa, said first therapeutic agent being a therapeutically effective amount of a compound as described herein or pharmaceutically acceptable salt thereof, in any embodiment as described herein; a pharmaceutically acceptable excipient, adjuvant or diluent; and a second therapeutic agent that is not a compound of Formula II or Formula IIa. In related aspects, the pharmaceutical formulation comprises a first therapeutic agent that is a compound of Formula II or Formula IIa as described herein, or a pharmaceutically acceptable salt thereof, and optionally comprises a second therapeutic agent that is not a compound of Formula II or Formula IIa, and optionally comprises a third therapeutic agent, and optionally comprises a fourth therapeutic agent, and optionally comprises a fifth therapeutic agent, and optionally comprises a sixth therapeutic agent. In related aspects, the second, third, fourth, fifth and sixth therapeutic agent is an anti-mycobacterial agent other than a compound of Formula II or Formula IIA. In related aspects, the second, third, fourth, fifth and sixth therapeutic agent is selected from isoniazid, rifampin, pyrazinamide, ethambutol, moxifloxacin, rifapentine, clofazimine, bedaquiline (TMC207), nitroimidazo-oxazine PA-824, delamanid (OPC-67683), oxazolidinone such as linezolid, tedizolid, radezolid, sutezolid (PNU-100480), and posizolid (AZD-5847), EMB analogue SQ109, a benzothiazinone, a dinitrobenzamide and an antiviral agent including an antiretroviral agent. In related aspects, the second, third, fourth, fifth and sixth therapeutic agent is a therapeutic agent approved and/or recommended for the treatment of tuberculosis.

A related embodiment provides a pharmaceutical formulation comprising a compound of Formula II or Formula IIa, or a salt thereof, and optionally comprises a second, third, fourth, fifth or sixth therapeutic agent, wherein the optional first, second, third, fourth, fifth or sixth therapeutic agent is an antiretroviral agent selected from of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

As described herein, embodiments of the invention include coadministering, whether simultaneously, sequentially or in combination, a first therapeutic agent that is a substituted benzoxaborole or salt thereof as described herein, preferably a substituted benzoxaborole of Formula II or Formula IIa as described herein, or a pharmaceutically acceptable salt thereof, optionally in combination with a second therapeutic agent, optionally in combination with a third therapeutic agent, optionally in combination with a fourth therapeutic agent, optionally in combination with a fifth and/or a sixth therapeutic agent, to a subject exposed to or infected with a mycobacterium species, including a *Mycobacterium tuberculosis* species. In certain embodiments, the first therapeutic agent is a tricyclic benzoxaborole compound of Formula II or Formula IIa as described herein or a pharmaceutically acceptable salt thereof, and the second and/or third and/or fourth therapeutic agent is an anti-tubercular agent. In certain embodiments, the mycobacterium species is a drug-resistant variant; in certain embodiments the mycobacterium species is a multi-drug resistant variant.

In other particular embodiments there is provided a method for killing mycobacteria comprising contacting the mycobacteria or an animal, including a human, exposed to or infected with a mycobacterium with a first therapeutic agent that is a compound of Formula II or Formula IIa as described herein, or a pharmaceutically acceptable salt thereof, optionally contacting the cells or subject with a second therapeutic agent, optionally contacting the cells or subject with a third therapeutic agent, optionally contacting the cells or subject with a fourth therapeutic agent, optionally contacting the cells or subject with a fifth and/or a sixth therapeutic agent, such that contacting kills mycobacteria cells. In particular embodiments, the first therapeutic agent is a substituted benzoxaborole that is a compound of Formula II or Formula IIa as described herein, or a pharmaceutically acceptable salt thereof and the optional second, third, fourth, fifth and/or sixth therapeutic agent is an anti-tubercular agent or a salt thereof. In other particular embodiments, the subject was exposed to or is infected with *Mycobacterium tuberculosis*.

Still other particular embodiments provide a method for inhibiting the replication of mycobacterial cells, the method comprising contacting the mycobacterial cells or an animal, including a human exposed to or infected with a mycobacterial cells with a first therapeutic agent that is a compound as described herein or a salt thereof, optionally contacting the mycobacterial cells or animal with a second therapeutic agent, optionally contacting the mycobacterial cells or animal with a third therapeutic agent, optionally contacting the mycobacterial cells or animal with a fourth therapeutic agent, optionally contacting the mycobacterial cells or animal with a fifth and/or a sixth therapeutic agent, such that contacting inhibits the replication of the mycobacterial cells. In particular embodiments, the first therapeutic agent is a substituted benzoxaborole that is a compound as described herein or a salt thereof and the optional second, third, fourth, fifth and/or sixth therapeutic agent is an anti-tubercular agent or a salt thereof. In other particular embodiments, the subject was exposed to or is infected with *Mycobacterium tuberculosis*.

BRIEF DESCRIPTIONS OF THE DRAWINGS

Figure 1:
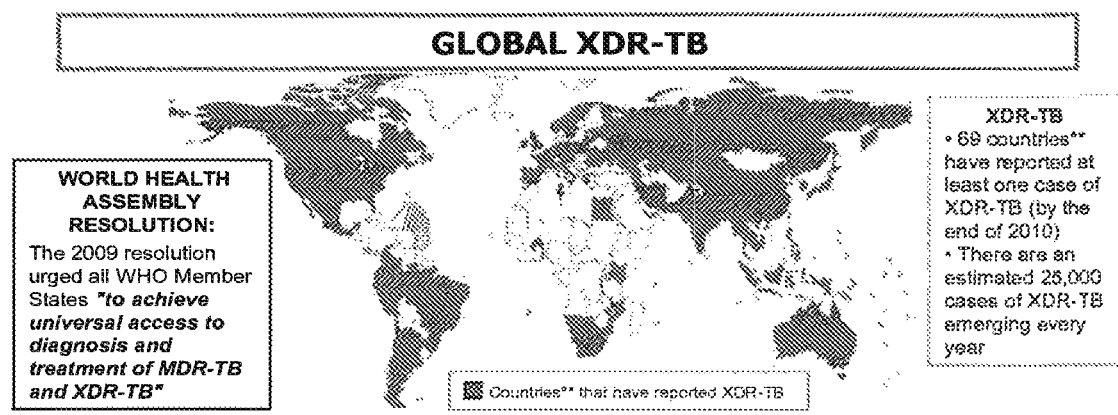
FIG. 1 is a world map indicating where, geographically, XDR-TB has been documented.
Figure 2:
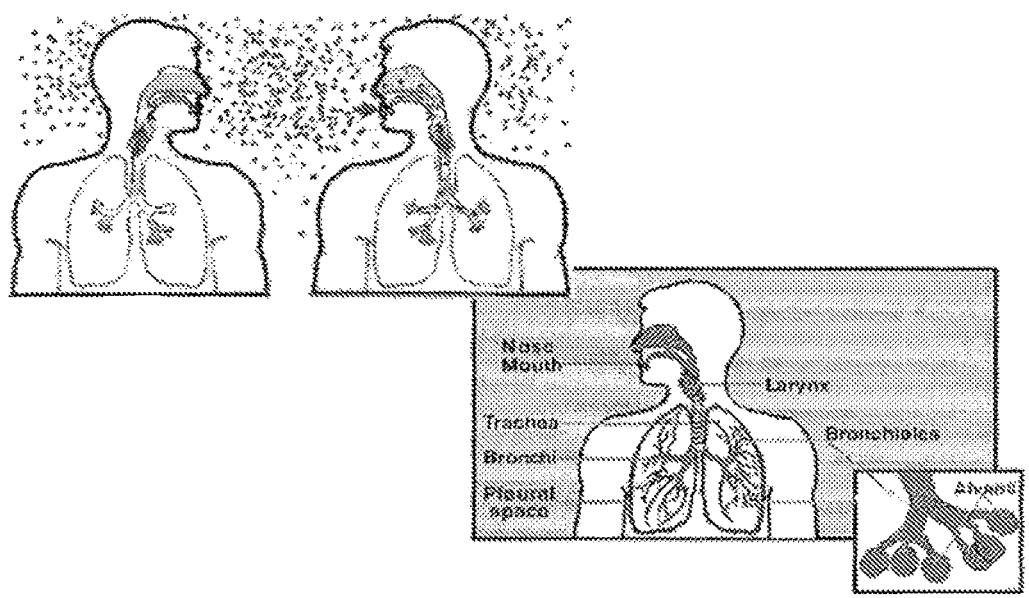
FIG. 2 shows transmission of tuberculosis.

Tables 1A and 1B provide MIC values for Example 4 G4-Cl tested against 97 *M. tuberculosis* Clinical Isolates: Sensitive (A) and Resistant (B). Table 1A is MIC results for Example 4 against *M. tuberculosis* strains sensitive to known TB agents and Table 1B is MIC results for Example 4 against *M. tuberculosis* strains resistant to one or more known TB agents. The resistance pattern of clinical isolates is indicated by the following abbreviations H: Isoniazide, R: Rifampicin, T: Ethionamide, S: Streptomycin, E: Ethambutol, Z: Pyrazynamide, K: Kanamycin, A: Amikacin and CP: Capreomycin.

Tables 2A and 2B provide MIC values for Example 4 G4-Cl tested against 40 strains of *M. tuberculosis* Clinical Isolates: Sensitive (A) and Resistant (B). Table 2A is MIC results for Example 4 against *M. tuberculosis* strains sensitive to (Standard of Care TB agents?) and Table 2B is MIC results for Example 4 against *M. tuberculosis* strains resistant to one or more known TB agents.

Tables 2C and 2D provide MIC values for Example 2 G2-Br tested against 40 strains of *M. tuberculosis* Clinical Isolates: Sensitive (A) and Resistant (B). Table 2C is MIC results for Example 2 against *M. tuberculosis* strains sensitive to known TB agent and Table 2D is MIC results for Example 2 against *M. tuberculosis* strains resistant to one or more known TB agents. The resistance pattern of clinical isolates is indicated by the following abbreviations H: Isoniazide, R: Rifampicin, T: Ethionamide, S: Streptomycin, E: Ethambutol, Z: Pyrazynamide, K: Kanamycin, A: Amikacin and CP: Capreomycin.

Table 3 provides MIC values against non-Mycobacterial strains for Compounds of Formula II or Formula IIa.

Table 4A provides LeuRS inhibition IC50 values, MIC values against the *M. tuberculosis* standard strain Mtb H37Rv, toxicity values against human HepG2 cells, and selectivity values for Certain Comparator Tricyclic Benzoxaborole Compounds.

Table 4B provides the data classifications listed in Table 4A for Compounds of Formula II or Formula IIa.

DETAILED DESCRIPTION OF SPECIFIC EMBODIMENTS

"Animal" as used herein means any of a kingdom (Animalia) of living things including many-celled organisms, including livestock and pets, including cattle, sheep, goats, dogs and cats, or a human, including an immune-suppressed human.

"Combination of the invention," as used herein refers to the combinations of compounds discussed herein, salts (e.g. pharmaceutically acceptable salts), prodrugs, solvates and hydrates of these compounds.

"Diastereomer" as used herein refers to one of a pair of stereoisomers that is not mirror images of the other stereoisomer.

"Enantiomer" as used herein refers to one of a pair of non-superimposable racemic compounds (racemates) that is a mirror image of the other enantiomer. Enantiomers have the property of rotating the plane of polarized light in one direction or another when in pure form but as a racemic mixture, the mixture does not rotate the plane of polarized light.

"Effective" amount of a compound, combination thereof or formulation thereof, means an amount of a compound that is the active agent, including a combination of formulation thereof, such that the amount is sufficient to provide the desired local or systemic effect. A "therapeutically effective" or "pharmaceutically effective" amount refers to the amount of compound, including a combination or formulation thereof, sufficient to achieve a desired therapeutic or pharmaceutical result.

The term "pharmaceutically acceptable salt" is meant to include a salt of a compound described herein which is prepared with relatively nontoxic acids or bases, depending on the particular substituents found on the compounds described herein. When compounds as described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine or l-lysine), or magnesium salt, or a similar salt. When compounds as described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds as described herein contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds as described herein. Additionally, prodrugs can be converted to the compounds of the invention by chemical or biochemical methods in an ex vivo environment.

Certain of the compounds of Formula II and Formula IIa may form acid addition salts with one or more equivalents of the acid. The present invention includes within its scope all possible stoichiometric and non-stoichiometric forms.

The compounds of Formula II and Formula IIa may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water). The subject invention also includes isotopically-labeled compounds which are identical to those recited in Formula II and Formula IIa but for the fact that one or more atoms are replaced by an atom having an atomic mass or mass number different from the atomic mass or mass number most commonly found in nature. Examples of isotopes that can be incorporated into compounds as described herein include isotopes of hydrogen, carbon, nitrogen, oxygen, fluorine, iodine and chlorine such as $^3$H, $^{11}$C, $^{14}$C, $^{18}$F, $^{123}$I or $^{125}$I.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3$H or $^{14}$C have been incorporated, are useful in drug and/or substrate tissue distribution assays. Tritiated, ie. $^3$H, and carbon-14, ie. $^{14}$C, isotopes are particularly preferred for their ease of preparation and detectability. $^{11}$C and $^{18}$F isotopes are particularly useful in PET (positron emission tomography).

Because the compounds of Formula II and Formula IIa as described herein are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

One embodiment provides a tricyclic benzoxaborole compound or a salt thereof having a structure according to Formula II:

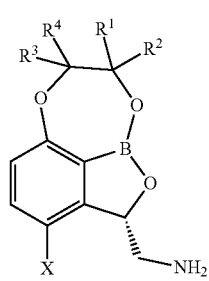

Formula II wherein X is selected from chloro, fluoro, bromo and iodo; $R^1$ and $R^2$ are each independently H, —CH$_3$, —CH$_2$CH$_3$, —CH$_2$CH$_2$CH$_3$, and —CH(CH$_3$)$_2$.

One embodiment provides a compound of Formula II wherein X is chloro or bromo and $R^1$ and $R^2$ are independently selected from H, —CH$_3$, —CH$_2$CH$_3$, —CH$_2$CH$_2$CH$_3$, and —CH(CH$_3$)$_2$.

One embodiment provides a compound of Formula II or a salt thereof, wherein X is chloro or bromo; $R^1$ and $R^2$ are independently H, —CH$_3$, or —CH$_2$CH$_3$.

One embodiment provides a compound of Formula II or a salt thereof, wherein X is chloro or bromo; $R^1$ and $R^2$ are independently selected from H and —CH$_3$.

One embodiment provides a compound of Formula II or a salt thereof, wherein X is fluoro or iodo; $R^1$ and $R^2$ are independently selected from H and —CH$_3$.

Another embodiment provides a compound of Formula IIa

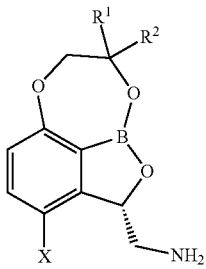

Formula IIa wherein X is fluoro, chloro, bromo or iodo, and $R^1$ and $R^2$ are independently H or —CH$_3$, or a pharmaceutically acceptable salt thereof.

In one aspect the invention provides a pharmaceutical composition comprising a compound of Formula II, or a pharmaceutically acceptable salt or solvate thereof, and one or more pharmaceutically acceptable carriers, excipients or diluents.

Another aspect of the invention further provides a method of treatment of a mycobacterial infection in a mammal, particularly in a human, which method comprises administering to a mammal in need of such treatment an effective amount of a first therapeutic agent that is a compound of Formula II or a compound of Formula IIa, or a pharmaceutically acceptable salt or solvate thereof. Related embodiments further comprise administering to a mammal in need of such treatment an effective amount of a first therapeutic agent that is a compound of Formula II or a compound of Formula IIa, or a pharmaceutically acceptable salt thereof, optionally administering in combination with an effective amount of a second therapeutic agent, optionally administering in combination with an effective amount of a third therapeutic agent, optionally administering in combination with an effective amount of a fourth therapeutic agent, optionally administering in combination with an effective amount of a fifth therapeutic agent, optionally administering in combination with an effective amount of a sixth therapeutic agent.

In related aspects of the embodiment the optional second, third, fourth, fifth and sixth therapeutic agent is an antimycobacterial agent. In related aspects, administering the first therapeutic agent and optionally administering the second, third, fourth, fifth and sixth therapeutic agent occurs concurrently, or administering the first therapeutic agent and optionally administering the second, third, fourth, fifth and sixth therapeutic agent occurs sequentially. In other related aspects of the invention, any one of the second, third, fourth, fifth or sixth therapeutic agent is selected from an antimicrobial agent, an antiviral agent, an anti-infective agent, an analgesic, a vitamin, a nutritional supplement, an anti-inflammatory agent, an analgesic, and an steroid.

The invention yet further provides a compound of Formula II, or a pharmaceutically acceptable salt or solvate thereof, for use in the treatment of a mycobacterial infection in a mammal, particularly in a human. In related aspects, the mammal is a human wherein the mycobacterial infection is a *Mycobacterium tuberculosis* infection. In other aspects, the human with a *Mycobacterium tuberculosis* infection is also infected with a retrovirus, including a human immunodeficiency virus.

The invention still further provides the use of a compound of Formula II or Formula IIa, or a pharmaceutically acceptable salt or solvate thereof, in the manufacture of a medicament for use in the treatment of a mycobacterial infection in a mammal, particularly in a human.

The invention also provides a pharmaceutical composition comprising a compound of Formula II or Formula IIa, or a pharmaceutically acceptable salt, or solvate thereof, and one or more pharmaceutically acceptable carriers, excipients or diluents, for use in the treatment of a mycobacterial infection in a mammal, particularly in a human.

The invention also provides a pharmaceutical composition comprising a compound of Formula II or Formula IIa, or a pharmaceutically acceptable salt, or solvate thereof, and one or more pharmaceutically acceptable carriers, excipients or diluents, for use in the treatment of mycobacterial infections in a mammal, particularly in a human.

In another particular embodiment the substituted benzoxaborole in the combination has a structure which is

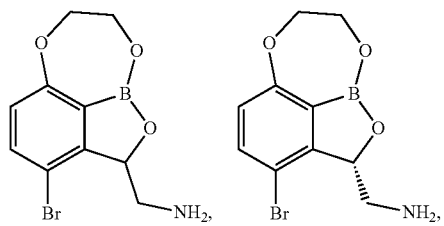

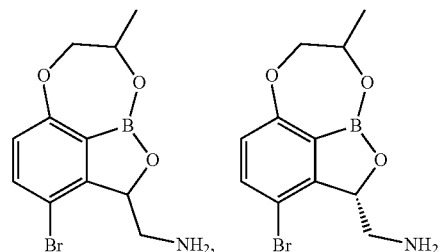

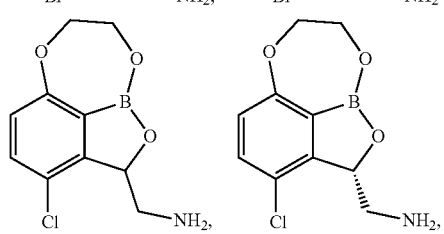

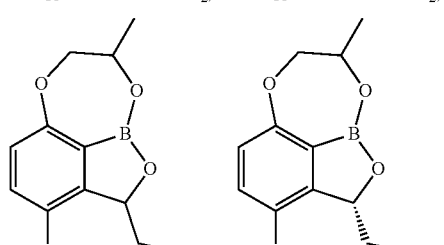

-continued

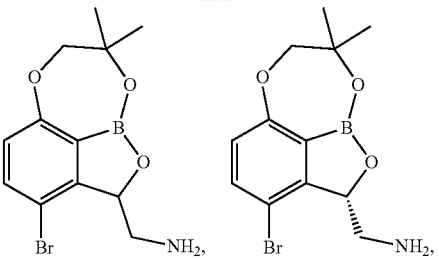

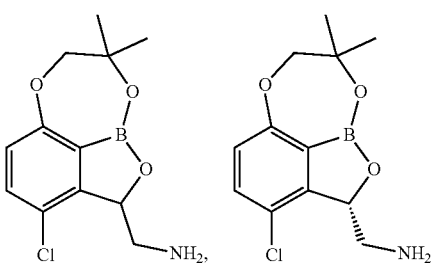

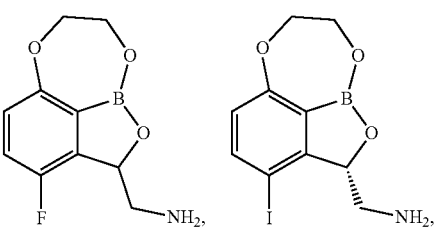

or a pharmaceutically acceptable salt thereof.

In one particular embodiment, the compound is

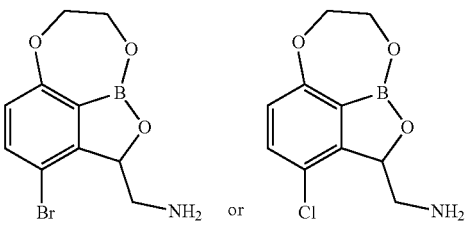 [SMILES: NCC1OB2OCCOc3ccc(Br)c1c32 ; "or" ; NCC1OB2OCCOc3ccc(Cl)c1c32]

or a pharmaceutically acceptable salt thereof.

In one particular embodiment, the compound is

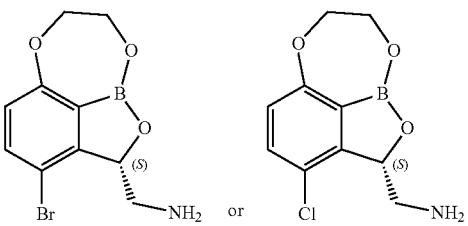

or a pharmaceutically acceptable salt thereof.

In one particular embodiment, the compound is

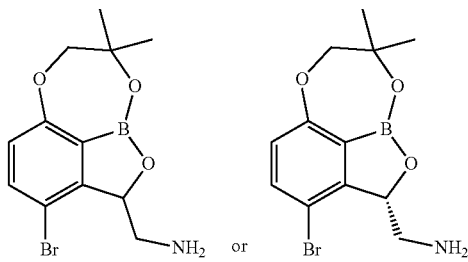 [SMILES: CC1(C)COc2ccc(Br)c3c2B(OC3CN)O1 ; "or" ; CC1(C)COc2ccc(Br)c3c2B(O[C@@H]3CN)O1]

or a pharmaceutically acceptable salt thereof.

In one particular embodiment, the compound is

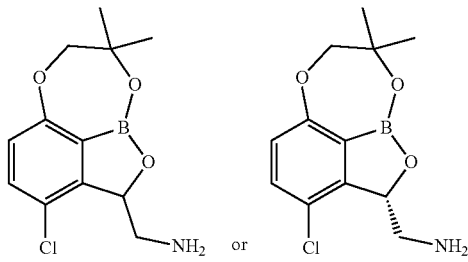 [SMILES: CC1(C)COc2ccc(Cl)c3c2B(OC3CN)O1 ; "or" ; CC1(C)COc2ccc(Cl)c3c2B(O[C@@H]3CN)O1]

or a pharmaceutically acceptable salt thereof.

An embodiment of the invention provides a compound which is:
(3-bromo-7,8-dihydro-2H-1,6,9-trioxa-9a-borabenzo[cd]azulen-2-yl)methanamine;
(S)-(3-bromo-7,8-dihydro-2H-1,6,9-trioxa-9a-borabenzo[cd]azulen-2-yl)methanamine;
(3-chloro-7,8-dihydro-2H-1,6,9-trioxa-9a-borabenzo[cd]azulen-2-yl)methanamine;
(S)-(3-chloro-7,8-dihydro-2H-1,6,9-trioxa-9a-borabenzo[cd]azulen-2-yl)methanamine;
(3-chloro-8-methyl-7,8-dihydro-2H-1,6,9-trioxa-9a-borabenzo[cd]azulen-2-yl)methanamine;
(3-bromo-8-methyl-7,8-dihydro-2H-1,6,9-trioxa-9a-borabenzo[cd]azulen-2-yl)methanamine;
(3-bromo-8,8-dimethyl-7,8-dihydro-2H-1,6,9-trioxa-9a-borabenzo[cd]azulen-2-yl)methanamine;
(S)-(3-bromo-8,8-dimethyl-7,8-dihydro-2H-1,6,9-trioxa-9a-borabenzo[cd]azulen-2-yl)methanamine;
(3-chloro-8,8-dimethyl-7,8-dihydro-2H-1,6,9-trioxa-9a-borabenzo[cd]azulen-2-yl)methanamine;
(S)-(3-chloro-8,8-dimethyl-7,8-dihydro-2H-1,6,9-trioxa-9a-borabenzo[cd]azulen-2-yl)methanamine;
(3-fluoro-7,8-dihydro-2H-1,6,9-trioxa-9a-borabenzo[cd]azulen-2-yl)methanamine;
(S)-(3-iodo-7,8-dihydro-2H-1,6,9-trioxa-9a-borabenzo[cd]azulen-2-yl)methanamine;
or a pharmaceutically acceptable salt thereof.

In another particular embodiment, the treatment of a mycobacterial infection or condition occurs through inhibition of an editing domain of an aminoacyl tRNA synthetase by means of binding to the editing active site. In another exemplary embodiment, the treatment of a mycobacterial infection or condition occurs through blocking of an editing domain of an aminoacyl tRNA synthetase.

In a particular embodiment, the mycobacterial infection and/or disease is treated through oral administration of the combination of the invention. In an exemplary embodiment, the mycobacterial infection and/or disease is treated through intravenous administration of the combination of the invention.

Pharmaceutical Formulations

In another aspect, the invention is a pharmaceutical formulation which includes: (a) a pharmaceutically acceptable excipient; (b) a combination of the invention. In another aspect, the pharmaceutical formulation includes: (a) a pharmaceutically acceptable excipient; and (b) a combination described herein. In another aspect, the pharmaceutical formulation includes: (a) a pharmaceutically acceptable excipient; and (b) a combination described herein, or a salt, prodrug, hydrate or solvate thereof. In another aspect, the pharmaceutical formulation includes: (a) a pharmaceutically acceptable excipient; and (b) a combination described herein, or a salt, hydrate or solvate thereof. In another aspect, the pharmaceutical formulation includes: (a) a pharmaceutically acceptable excipient; and (b) a combination described herein, or a salt, hydrate or solvate thereof. In another aspect, the pharmaceutical formulation includes: (a) a pharmaceutically acceptable excipient; and (b) a salt of a combination described herein. In an exemplary embodiment, the salt is a pharmaceutically acceptable salt. In another aspect, the pharmaceutical formulation includes: (a) a pharmaceutically acceptable excipient; and (b) a prodrug of a combination described herein. In another aspect, the pharmaceutical formulation includes: (a) a pharmaceutically acceptable excipient; and (b) a combination described herein. In an exemplary embodiment, the pharmaceutical formulation is a unit dosage form. In an exemplary embodiment, the pharmaceutical formulation is a single unit dosage form.

In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a three unit dosage form. In an exemplary embodiment, the pharmaceutical formulation is a four unit dosage form. In an exemplary embodiment, the pharmaceutical formulation is a five unit dosage form. In an exemplary embodiment, the pharmaceutical formulation is a six unit dosage form. In an exemplary embodiment, the pharmaceutical formulation is a one, two, three, four, five, six or seven unit dosage form comprising a first unit dosage form and a second, third, fourth, fifth and/or sixth unit dosage form, wherein the first unit dosage form includes a) a therapeutically effective amount of a compound as described herein and b) a first pharmaceutically acceptable excipient; and the second, third, fourth, fifth, and/or sixth unit dosage form includes c) a therapeutically acceptable amount of an additional therapeutic agent that is an anti-mycobacterial agent and d) a second pharmaceutically acceptable excipient.

Information regarding excipients of use in the formulations of the invention can be found in Remington: The Science and Practice of Pharmacy, 21st Ed., Pharmaceutical Press (2011) which is incorporated herein by reference.

Combinations

In an exemplary embodiment, the invention provides a) a first therapeutic agent that is a tricyclic benzoxaborole compound or salt thereof as described herein; b) a second therapeutic activity. In certain embodiments, the second therapeutic agent is an antibacterial agent, more specifically an anti-tubercular agent, more specifically an anti-*M. tuberculosis* agent.

In an exemplary embodiment, the combination is part of a pharmaceutical formulation described herein. Such conditions are known to one skilled in the art and specific conditions are set forth in the Examples appended hereto.

Dosage forms of the Combination

The individual components of the combinations of the invention, for example, a combination described herein, may be administered either simultaneously or sequentially in a unit dosage form. The unit dosage form may be a single or multiple unit dosage form. In an exemplary embodiment, the invention provides a combination in a single unit dosage form. An example of a single unit dosage form is a capsule wherein both the tricyclic benzoxaborole compound and additional therapeutic agent are contained within the same capsule. In an exemplary embodiment, the invention provides a combination in a two unit dosage form. An example of a two unit dosage form is a first capsule which contains the tricyclic benzoxaborole compound and a second capsule which contains the additional therapeutic agent. Thus the term 'single unit' or 'two unit' or 'multiple unit' refers to the object which the patient ingests, not to the interior components of the object. Appropriate doses of tricyclic benzoxaborole compound will be readily appreciated by those skilled in the art. Appropriate doses of an additional therapeutic agent that is not a compound of Formula II or Formula IIA will be readily appreciated by those skilled in the art. In one particular embodiment, the tricyclic benzoxaborole compound is present in the combination in a therapeutically effective amount. In one particular embodiment, the additional therapeutic agent that is not a compound of Formula II or Formula IIA is present in the combination in an amount sufficient to kill or reduce the presence, amount or growth rate of mycobacteria exposed to the substituted benzoxaborole, including *M. tuberculosis*.

Additional therapeutic agent(s) in the Combination

The combinations of the invention, for example, a combination described herein, may also include an additional therapeutic agent or therapeutic agents. The invention thus provides, in a further aspect, a combination comprising a tricyclic benzoxaborole compound described herein or a pharmaceutically acceptable salt thereof, and at least one additional therapeutic agent. The invention thus provides, in a further aspect, a combination comprising a tricyclic benzoxaborole compound described herein or a pharmaceutically acceptable salt thereof, and at least one additional therapeutic agent. In an exemplary embodiment, the additional therapeutic agent is an antimycobacterial agent. In one aspect, the invention comprises: a) a combination of the invention; and b) at least one additional therapeutic agent. In another exemplary embodiment, the invention comprises: a) a combination of the invention; b) a first additional therapeutic agent; and c) a second additional therapeutic agent. In another exemplary embodiment, the invention comprises: a) a combination of the invention; b) a first additional therapeutic agent; c) a second additional therapeutic agent; and d) a third additional therapeutic agent. The first additional therapeutic agent or second additional therapeutic agent or third additional therapeutic agent may be selected from the additional therapeutic agents described herein.

The combinations may conveniently be presented for use in the form of a pharmaceutical formulation. In a further aspect of the present invention there is provided a pharmaceutical combination comprising a compound of Formula II, or a pharmaceutically acceptable salt or solvate thereof, together with one or more additional therapeutic agents, and one or more pharmaceutically acceptable carriers, excipients or diluents. The individual components of such combinations may be administered either sequentially or simultaneously in separate or combined pharmaceutical Formulations by any convenient route.

When an additional therapeutic agent is used with a combination as described herein against the same disease state, the dose of each compound may differ from that when the compound is used alone. Appropriate doses will be readily appreciated by those skilled in the art. It will be appreciated that the amount of a compound as described herein required for use in treatment will vary with the nature of the condition being treated and the age and the condition of the patient and will be ultimately at the discretion of the attendant physician or veterinarian.

Preparation of Boron-Containing Compounds

Compounds of use in the invention can be prepared using commercially available starting materials, known intermediates, or by using the synthetic methods described herein, or published in references described and incorporated by reference herein, such as U.S. Pat. No. 7,816,344 and PCT Pat. Pubs. WO2010080558 and WO2011127143. The general procedures used to synthesize the compounds of Formula II and Formula IIa, are described in reaction Schemes 1-5 and are illustrated in the Examples.

Certain tricyclic benzoxaborole compounds may be prepared by a Mitsunobu reaction to convert the hydroxyl substituent of 2-bromo-3-hydroxy-benzaldehyde into the tetrahydropyranyloxyethoxy ether with tetrahydropyranyloxyethanol in triphenylphosphine ($PPh_3$), tetrahydrofuran (THF) and diisopropyl azodicarboxylate (DIAD), followed by Miyaura borylation of the bromine substituent using bis(pinocolato)diboron diboron ($B_2pin_2$) with a palladium catalyst ($PdCl_2$) and potassium acetate (KOAc), and then reductive ring closure to form the tricyclic compound using sodium borohydride ($NaBH_4$) in anhydrous methanol (MeOH), as outlined in Scheme 1.

Scheme I

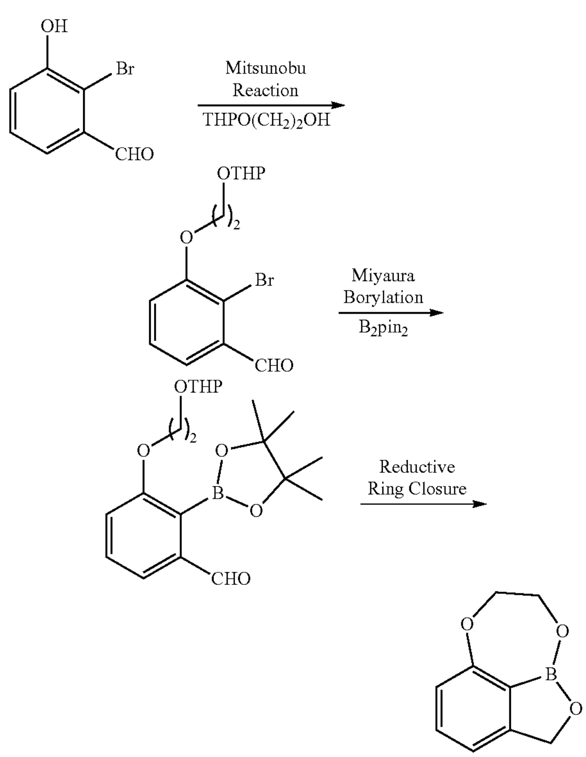

THP-protected alkyl bromide may also be used to attach a substituent to hydroxybenzaldehyde via a SN2 reaction to prepare tricyclic benzoxaborole compounds. Examples of the use of a SN2 reaction for preparing tricyclic benzoxaborole compounds can be seen in the Examples described below, such as in Example 1, step (b) and Example 4, Method B, step (c).

Other tricyclic benzoxaborole compounds as described herein may be prepared as outlined in Schemes 2 and 3, wherein a nitro-aldol reaction is performed on the aldehyde substituent of, for example, 3-(2-benzyloxy-ethoxy)-2-(4,4,5,5-tetramethyl-[1,3,2]dioxaborolan-2-yl)-benzaldehyde using nitromethane (MeNO$_2$) with base (NaOH) to prepare the nitro-substituted benzyl-protected benzoxaborole compound, followed by ring-closure to and reduction of the nitro substituent to the amine with Pd(OH)$_2$/C in glacial acetic acid to form the desired tricyclic benzoxaborole compound.

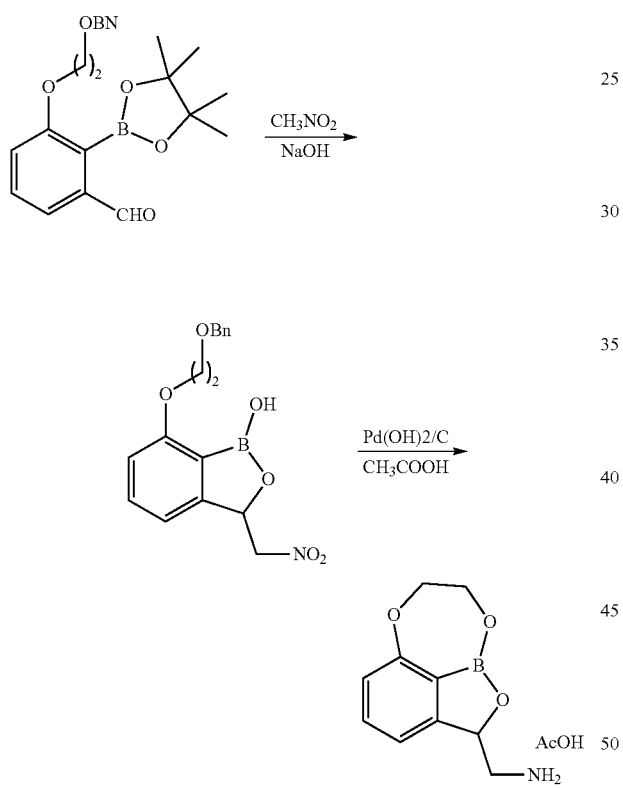

Scheme 2

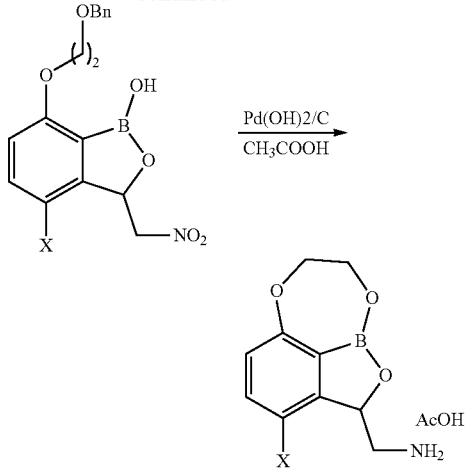

-continued

Other tricyclic benzoxaborole compounds as described herein may be prepared as outlined in Scheme 4.

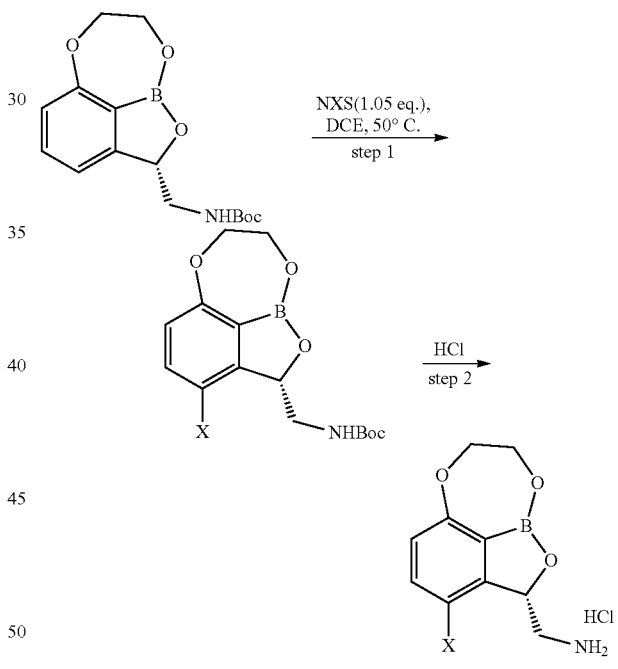

Scheme 4

Other tricyclic benzoxaborole compounds as described herein may be prepared as outlined in Scheme 5.

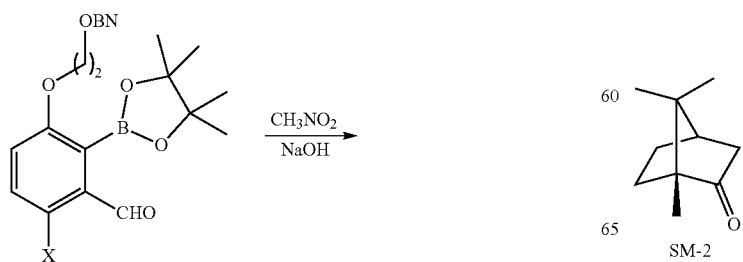

Scheme 3

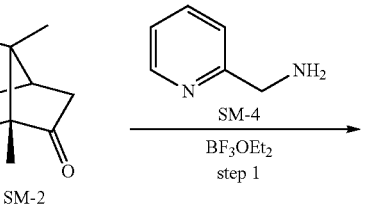

Scheme 5

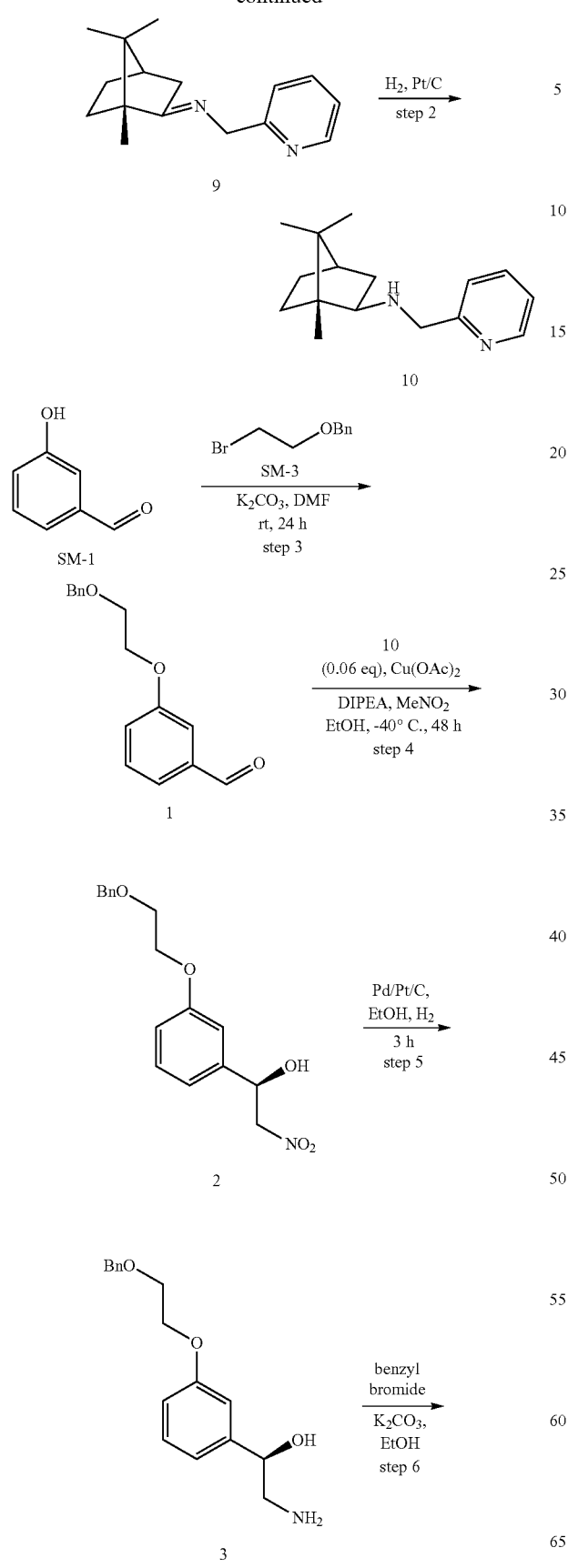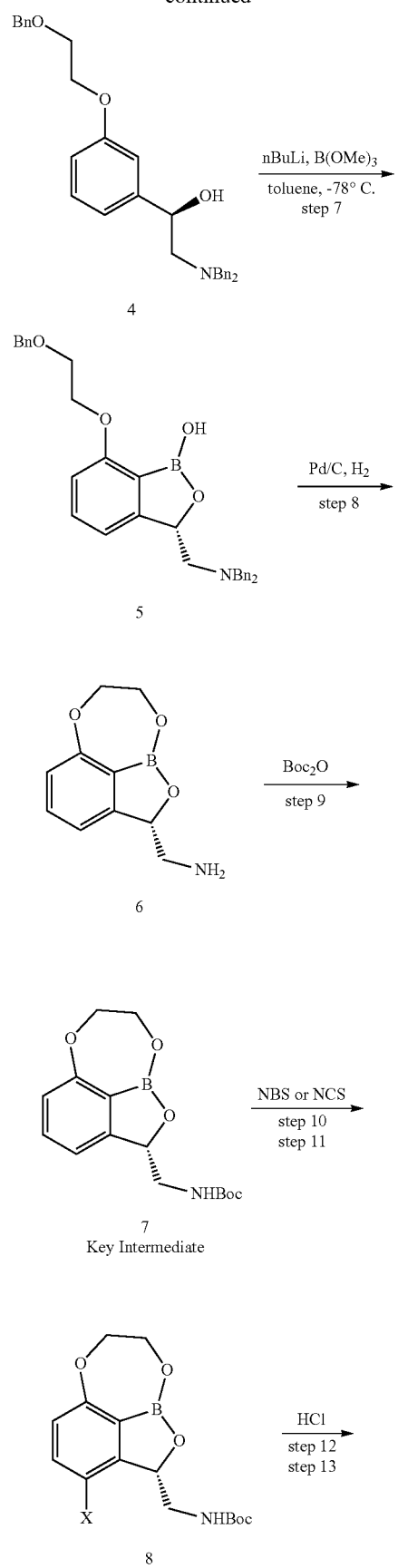

-continued

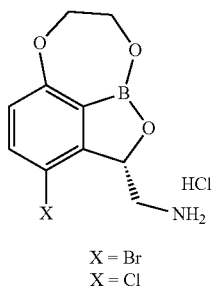

X = Br
X = Cl

Alternatively, certain tricyclic benzoxaborole compounds may be prepared as outlined in Scheme 6. A mixture of (S)-tert-butyl ((7,8-dihydro-2H-1,6,9-trioxa-9a-borabenzo[cd]azulen-2-yl)methyl)carbamate (13.25 kg) and NCS (8.75 kg) in dichloroethane (132.5 L) was heated at 70° C. until the reaction judged complete by HPLC. The mixture was concentrated under reduced pressure, cooled to 25° C. and acetone (106 L) added. The slurry was filtered, washing with acetone (26.5 L). The wet cake was slurried in water (13.25 L) and 1,4-dioxane (66.25 L), heated to 50° C. for 20-30 minutes, cooled to 15° C., filtered and the cake washed with 1,4-dioxane (26.5 L). The wet cake was dissolved in methanol (68.9 L), filtered and the filtrate concentrated under reduced pressure. Methyl tertiary butyl ether (66.25 L) was added to the residue and the mixture concentrated under reduced pressure. Methyl tertiary butyl ether (78.7 L), isopropanol (8.7 L) and sulphuric acid (4.6 L) were added, the mixture heated to 50° C. and stirred until the sulphate content was 24.32-29.72%. The mixture was cooled to 25° C., stirred for 1 hour, filtered, the cake washed with methyl tertiary butyl ether (17.5 L) and dried to give the desired product (42%).

Scheme 6

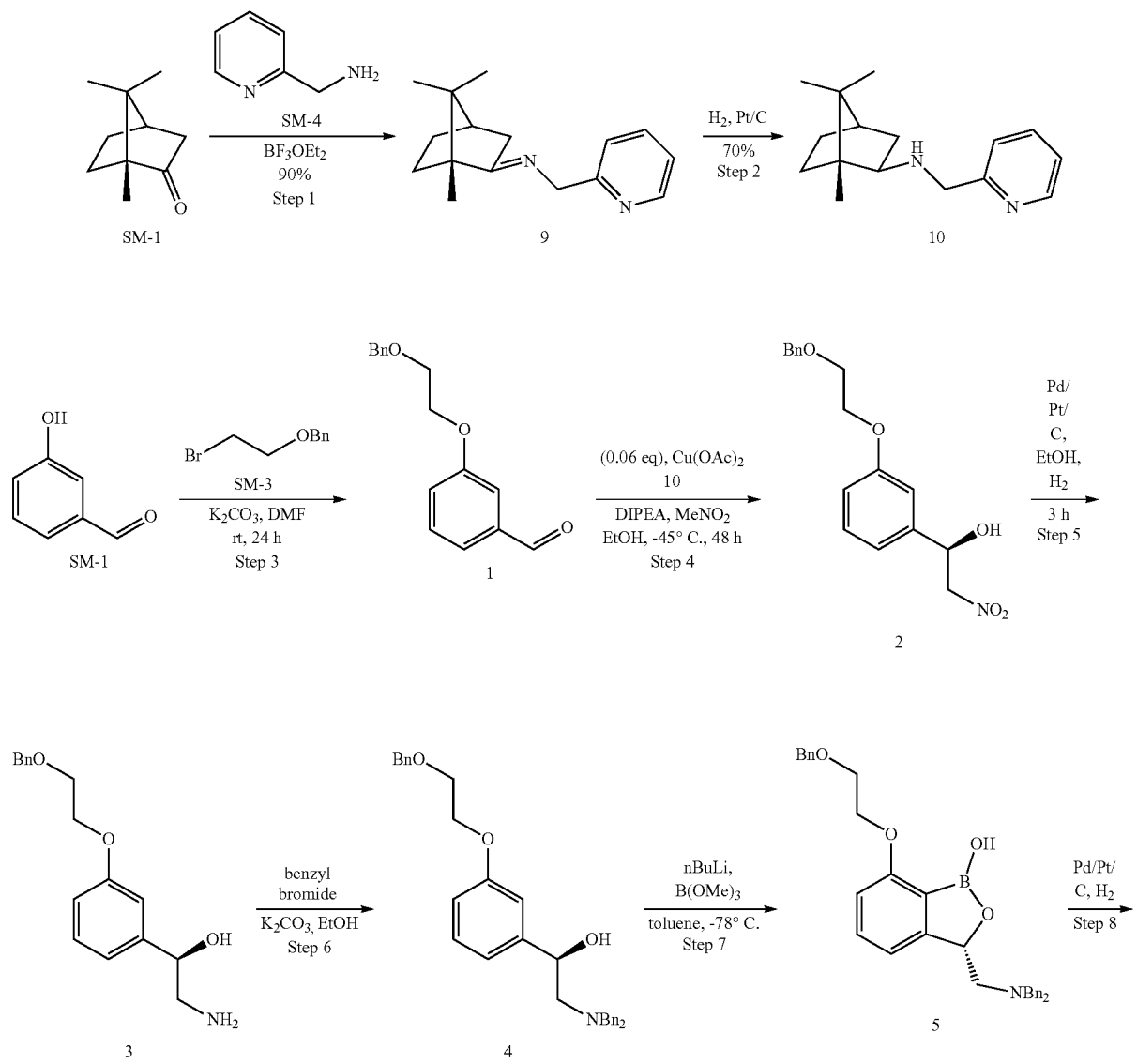

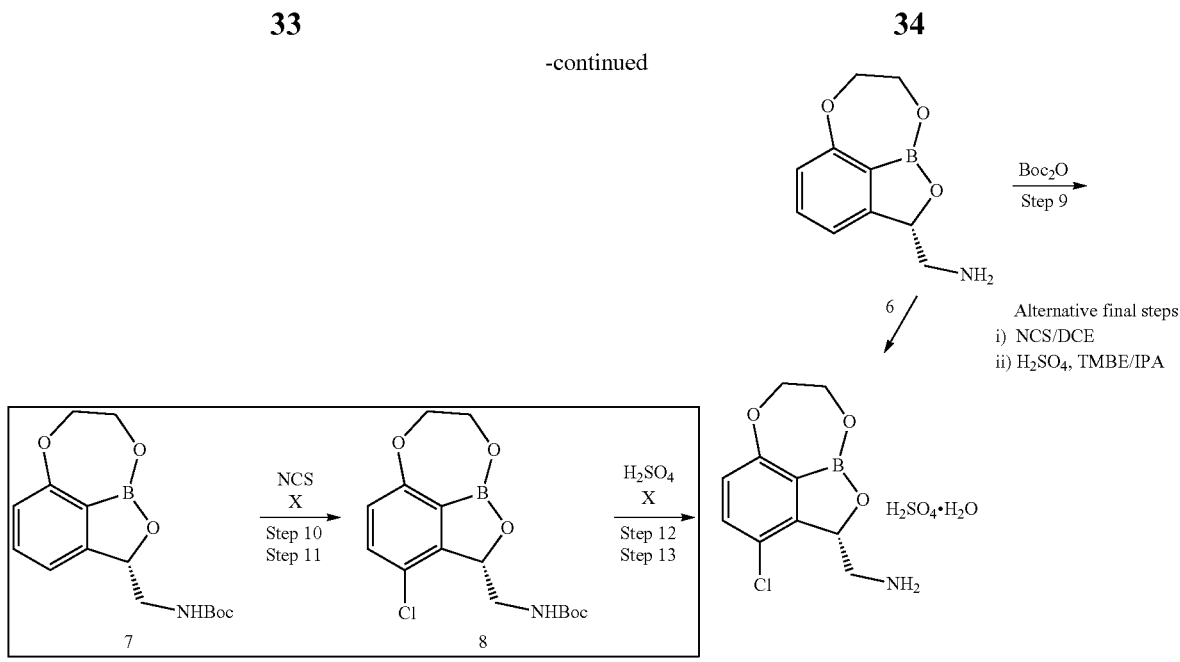

As can be seen in Scheme 6, in this route the final steps 10/11 and 12/13 are replaced with alternative final steps, eliminating the protection/deprotection steps.

Composition and Formulations

The compounds as described herein may be formulated for administration in any convenient way for use in human or veterinary medicine, by analogy with formulation of anti-mycobacterial agents, or formulation of other anti-tubercular agents.

The compounds described herein will normally, but not necessarily, be formulated into pharmaceutical compositions prior to administration to a patient. In one aspect, the invention is directed to a pharmaceutical composition comprising a compound of Formula II or compound of Formula IIa, or a pharmaceutically acceptable salt. In another aspect the invention is directed to a pharmaceutical composition comprising a compound of Formula II or a compound of Formula IIa, or a pharmaceutically acceptable salt, and one or more pharmaceutically acceptable carriers, excipients or diluents. The carrier, excipient or diluent must be "acceptable" in the sense of being compatible with the other ingredients of the Formulation and not deleterious to the recipient thereof.

The pharmaceutical compositions described herein include those in a form adapted for oral, or parenteral use and may be used for the treatment of a mycobacterial infection in a mammal including a human.

The pharmaceutical compositions described herein include those in a form adapted for oral, topical or parenteral use and may be used for the treatment of mycobacterial infections in a mammal including a human.

The composition may be formulated for administration by any convenient route. For the treatment of tuberculosis, the compositions may be in the form of tablets, capsules, powders, granules, lozenges, aerosols or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

In one aspect of the invention, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 20-1000 mg of the active ingredient. The dosage as employed for adult human treatment will typically range from 50 to 300 mg per day, for instance 150 to 200 mg per day depending on the route and frequency of administration. Such a dosage corresponds to 0.5 to 5 mg/kg per day. Preferably the dosage is from 0.5 to 2 mg/kg per day and more preferably the dose is less than 1 mg/kg per day.

The compound of Formula II or Formula IIa, or a pharmaceutically acceptable pharmaceutically acceptable salt or solvate thereof, may be the sole therapeutic agent in the compositions described herein, or it may be present in the Formulation in combination with one or more additional therapeutic agents. The invention thus provides, in a further aspect, a combination comprising a compound of Formula II, or a pharmaceutically acceptable salt, solvate thereof together with one or more additional therapeutic agents.

The one or more additional therapeutic agent is, for example, an agent useful for the treatment of tuberculosis in a mammal. Examples of such therapeutic agents include, rifampin, pyrazinamide, ethambutol, moxifloxacin, rifapentine, clofazimine, bedaquiline (TMC207), nitroimidazo-oxazine PA-824, delamanid (OPC-67683), oxazolidinone such as linezolid, tedizolid, radezolid, sutezolid (PNU-100480), and posizolid (AZD-5847), EMB analogue SQ109, a benzothiazinone, a dinitrobenzamide and an antiviral agent including an antiretroviral agent, or any TB agent being developed for the treatment of TB with a positive response in Phase IIa EBA trials, or any TB agent under development by the Global Alliance for Tuberculosis.

When a compound of Formula II or Formula IIa, or a pharmaceutically acceptable salt or solvate thereof is used in combination with one or more additional therapeutic agents, the dose of the compound or agent may differ from that when the compound or agent is used alone. Appropriate doses will be readily appreciated by those skilled in the art. It will be appreciated that the amount of a compound described herein and the one or more additional therapeutic agents required for use in treatment will vary with the nature of the condition being treated and the age and the condition of the patient and will be ultimately at the discretion of the attendant physician or veterinarian.

The combinations may conveniently be presented for use in the form of a pharmaceutical Formulation. In a further aspect of the present invention there is provided a pharmaceutical combination comprising a compound of Formula II, or a pharmaceutically acceptable salt or solvate thereof, together with one or more additional therapeutic agents, and one or more pharmaceutically acceptable carriers, excipients or diluents. The individual components of such combinations may be administered either sequentially or simultaneously in separate or combined pharmaceutical Formulations by any convenient route.

When administration is sequential, either the compound of the present invention or one or more additional therapeutic agent may be administered first. When administration is simultaneous, the combination may be administered either in the same or different pharmaceutical composition. When combined in the same Formulation it will be appreciated that the compound and agents must be stable and compatible with each other and the other components of the Formulation. When formulated separately they may be provided in any convenient formulation, conveniently in such manner as are known for such compounds in the art.

Methods of Inhibiting Bacterial Growth or Killing Bacteria

The combinations of the invention are expected to exhibit potency against mycobacteria and therefore have the potential to kill mycobacteria and/or inhibit the replication of mycobacteria. The combinations of the invention are expected to exhibit potency against mycobacteria possessing resistance to standard-of-care anti-mycobacterial agents, and thus have the potential to kill mycobacteria and/or inhibit the replication of such "resistant" mycobacteria. In aspects of the invention, compounds as described herein possess a remarkable activity against a selection of drug sensitive mycobacterial isolates, including, MDR-TB (multidrug resistant TB) and XDR-TB (extensively-drug resistant TB) clinical isolates, exhibiting MIC values of <0.32 µM and the majority have MIC values at between 0.04-0.08 µM in 96 isolates investigated.

In a further aspect, the invention provides a method of killing mycobacteria and/or inhibiting replication of mycobactera or a method of treating a mycobacterial infection in an animal such as livestock and pets, including cattle sheep, goats, dogs and cats, or a human, including an immune-suppressed human said method comprising: contacting the mycobactera with an effective amount of a combination as described herein, thereby killing the mycobacteria and/or inhibiting replication of the mycobacteria, or said method comprising administering to the animal with the mycobacterial infection a therapeutically effective amount of a combination of the invention, wherein the combination comprises a compound of Formula II or a compound of Formula IIa, or a pharmaceutically acceptable salt thereof. In an exemplary embodiment, the combination is part of a pharmaceutical formulation described herein. In another exemplary embodiment, the contacting occurs under conditions which permit entry of the combination into the mycobacterium.

In an exemplary embodiment, the mycobacteria is killed or its replication is inhibited, or the mycobacterial infection is treated, through oral administration of a combination as described herein. In an exemplary embodiment, the mycobacteriais killed or its replication is inhibited, or the mycobacterial infection is treated, through intravenous administration of a combination as described herein. In an exemplary embodiment, the mycobacterium is killed or its replication is inhibited, or the mycobacterial infection is treated, through subcutaneous administration of a combination as described herein, wherein the combination comprises a compound of Formula II or a compound of Formula IIa, or a pharmaceutically acceptable salt thereof.

In exemplary embodiments, the mycobacteria is contacted or the mycobacterial infection is treated with a combination as described herein comprising a first therapeutic agent that is a compound of Formula II or a compound of Formula IIa, or salt thereof, and optionally comprising a second, third, fourth, fifth and sixth therapeutic agent in a population of mycobacteria comprising a resistant mycobacterium with a mutation conferring resistance to any one or more of the optional second, third, fourth, fifth and sixth therapeutic agent. In related embodiments, the optional second, third, fourth, fifth and sixth therapeutic agent, or a salt thereof, is an anti-mycobacterial agent, particularly a known anti-mycobacterial agent, more preferably a standard-of-care anti-mycobacterial agent.

In another exemplary embodiment, there is provided a method of killing and/or inhibiting replication of mycobacteria that causes or is associated with a disease in an animal, or a method of treating a mycobacterial infection in an animal, the method comprising contacting the mycobacteria with an effective amount of a compound of Formula II or Formula IIa or a salt thereof, so as to kill and/or prevent replication of the mycobacterium, or administering to the animal a therapeutically effective amount of a compound of Formula II or Formula IIa or a salt thereof, wherein the mycobacteria is selected from *Mycobacterium tuberculosis*, *Mycobacterium avium* including subspecies (subsp.) *Mycobacterium avium* subsp. *avium*, *Mycobacterium avium* subsp. *hominissuis*, *Mycobacterium avium* subsp. *silvaticum*, and *Mycobacterium avium* subsp. *paratuberculosis*; *Mycobacterium balnei*, *Mycobacterium sherrisii*, *Mycobacterium africanum*, *Mycobacterium microti*, *Mycobacterium silvaticum*, *Mycobacterium colombiense*, *Mycobacterium indicus pranii*, *Mycobacterium gastri*, *Mycobacterium gordonae*, *Mycobacterium hiberniae*, *Mycobacterium nonchromagenicum*, *Mycobacterium terrae*, *Mycobacterium trivial*, *Mycobacterium kansasii*; *Mycobacterium malmoense*; *Mycobacterium simiae*; *Mycobacterium triplex*, *Mycobacterium genavense*, *Mycobacterium florentinum*, *Mycobacterium lentiflavum*, *Mycobacterium palustre*, *Mycobacterium kubicae*, *Mycobacterium parascrofulaceum*, *Mycobacterium heidelbergense*, *Mycobacterium interjectum*, *Mycobacterium szulgai*; *Mycobacterium branderi*, *Mycobacterium cookie*, *Mycobacterium celatum*, *Mycobacterium bohemicum*, *Mycobacterium haemophilum*, *Mycobacterium lepraemurium*, *Mycobacterium lepromatosis*, *Mycobacterium botniense*, *Mycobacterium chimaera*, *Mycobacterium conspicuum*, *Mycobacterium doricum*, *Mycobacterium forcinogenes*, *Mycobacterium heckeshornense*, *Mycobacterium lacus*, *Mycobacterium monacense*, *Mycobacterium montefiorense*, *Mycobacterium murale*, *Mycobacterium nebraskense*, *Mycobacterium saskatchewanenese*, *Mycobacterium scrofulaceum*, *Mycobacterium shimoidel*, *Mycobacterium tusciae*, *Mycobacterium xenopi*, *Mycobacterium intermedium*, *Mycobacterium bolletii*, *Mycobacterium fortuitum*, *Mycobacterium foruitum* subsp. *acetamidolyticum*, *Mycobacterium boenickei*, *Mycobacterium perigrinum*, *Mycobacterium porcinum*, *Mycobacterium senegalense*, *Mycobacterium septicum*, *Mycobacterium neworleansense*, *Mycobacterium houstonense*, *Mycobacterium mucogenicum*, *Mycobacterium mageritense*, *Mycobacterium brisbanense*, *Mycobacterium cosmeticum*, *Mycobacterium parafortuitum*, *Mycobacterium austroafricanum*, *Mycobacterium diemhoferi*, *Mycobacterium hodieri*, *Mycobacterium neoaurum*, *Mycobacterium prederkisbergense*, *Mycobacterium aurum*, *Mycobacterium vaccae*, *Mycobacterium chitae*, *Mycobacterium fallax*, *Mycobacterium confluentis*, *Mycobacterium flavenscens*, *Mycobacterium madagascariense*, *Mycobacterium phlei*, *Mycobacterium smegmatis*, *Mycobacterium goodie*, *Mycobacterium colinskui*, *Mycobacterium thermoresistbile*, *Mycobacterium gadium*, *Mycobacterium kormossense*, *Mycobacterium obuense*, *Mycobacterium sphagni*, *Mycobacterium agri*, *Mycobacterium aichiense*, *Mycobacterium alvei*, *Mycobacterium arupense*, *Mycobacterium brumae*, *Mycobacterium canariasense*, *Mycobacterium chubuense*, *Mycobacterium conceptionense*, *Mycobacterium duvalii*, *Mycobacterium elephantis*, *Mycobacterium gilvum*, *Mycobacterium hassiacum*, *Mycobacterium holsaticum*, *Mycobacterium immunogenum*, *Mycobacterium massiliense*, *Mycobacterium moriokaense*, *Mycobacterium psychrotoleranse*, *Mycobacterium pyrenivorans*, *Mycobacterium vanbaalenii*, *Mycobacterium pulveris*, *Mycobacterium arosiense*, *Mycobacterium aubagnense*, *Mycobacterium caprae*, *Mycobacterium chlorophenolicum*, *Mycobacterium fluoroanthenivorans*, *Mycobacterium kumamotonense*, *Mycobacterium novocastrense*, *Mycobacterium parmense*, *Mycobacterium phocaicum*, *Mycobacterium poriferae*, *Mycobacterium rhodesiae*, *Mycobacterium seolense*, *Mycobacterium tokalense*, *Mycobacterium xenopi*; *Mycobacterium scrofulaceum*; *Mycobacterium abscessus*; *Mycobacterium chelonae*; *Mycobacterium haemophilum*; *Mycobacterium leprae*; *Mycobacterium marinum*; *Mycobacterium fortuitum*; *Mycobacterium bovis*; *Mycobacterium ulcerans*; *Mycobacterium pseudoshottsii*, *Mycobacterium shottsii*, *Mycobacterium intracellulare*; *Mycobacterium tuberculosis* complex (MTC); *Mycobacterium avian-intracellulare* complex (MAIC) member and *Mycobacterium avium* complex (MAC) member.

In related aspects, the mycobacterium is *Mycobacterium tuberculosis*. In other aspects, the mycobacterium is *Mycobacterium avium*, *Mycobacterium kansasii*, *Mycobacterium malmoense*, *Mycobacterium simiae*, *Mycobacterium szulgai*, *Mycobacterium xenopi*, *Mycobacterium scrofulaceum*, *Mycobacterium abscessus*, *Mycobacterium chelonae*, *Mycobacterium haemophilum*, *Mycobacterium leprae*, *Mycobacterium marinum*, *M. fortuitum*, *Mycobacterium bovis*, *M. bovis* BCG, *M. africanum*, *M. canetti*, *M. caprae*, *M. microti*, *M. pinnipedi*, *M. leprae* or *Mycobacterium ulcerans*. In related embodiments, the mycobacterium is a subspecies (subsp.) of *Mycobacterium avium*, including *Mycobacterium avium* subsp. *avium*, *Mycobacterium avium* subsp. *hominissuis*, *Mycobacterium avium* subsp. *silvaticum*, and *Mycobacterium avium* subsp. *paratuberculosis*. In another related embodiment, the mycobacterium is *Mycobacterium intracellulare*. In further related embodiments, the mycobacterium is a member of the *Mycobacterium tuberculosis* complex. (MTC) the *Mycobacterium avium* complex (MAC) or the *Mycobacterium avian-intracellulare* complex (MAIC). In related embodiments, the mycobacterium is a non-tuberculosis complex or clade, including: *Mycobacterium avium* complex; *Mycobacterium gordonae* clade; *Mycobacterium kansasii* clade; *Mycobacterium chelonae* clade; *Mycobacterium fortuitum* clade; *Mycobacterium parafortuitum* clade; and *Mycobacterium vaccae* clade.

In an exemplary embodiment, the mycobacteria in the methods described herein comprises a resistant mycobacterium. In an exemplary embodiment, the resistant mycobacterium is a mutation of a mycobacteria described herein.

Methods of Treating and/or Preventing Disease

The combinations of the present invention exhibit potency against mycobacteria, and therefore have the potential to achieve therapeutic efficacy in animals, including humans.

In another aspect, the invention provides a method of treating and/or preventing a disease. The method includes administering to the animal a therapeutically effective amount of a combination of the invention, sufficient to treat and/or prevent the disease. In an exemplary embodiment, the combination of the invention can be used in human or veterinary medical therapy, particularly in the treatment or prophylaxis of mycobacterial-associated disease. In an exemplary embodiment, the combination is described herein.

In another exemplary embodiment, the animal is as defined herein. In another exemplary embodiment, the disease a systemic disease or a cutaneous disease. In another exemplary embodiment, the disease is a respiratory disease.

ABBREVIATIONS

In describing the invention, chemical elements are identified in accordance with the Periodic Table of the Elements.

Abbreviations and symbols utilized herein are in accordance with the common usage of such abbreviations and symbols by those skilled in the chemical arts. The following abbreviations are used herein:

AcOH acetic acid
Ac$_2$O acetic anhydride
AIBN 2-2'-Azoisobutyronitrile
BOC N-tert-butoxycarbonyl
BOC anhydride di-tert-butyl dicarbonate
B$_2$pin$_2$ bis(pinacolato)diboron diboron, also known as 4,4,4',4',5,5,5',5'-octamethyl-2,2'-bi(1,3,2-dioxaborolane
Celite® a filter aid composed of acid-washed diatomaceous silica, (a trademark of Manville Corp., Denver, Colo.)
CTAB cetyltrimethylammonium bromide
DCM dichloromethane
DIAD diisopropyl azodicarboxylate
DIBAL-H diisobutyl aluminium hydride
DME dimethoxyethane
DCE dichloroethane
DMF dimethylformamide
DMSO-d6 deuterated dimethylsulfoxide
DMSO dimethylsulfoxide
ESI Electrospray ionization
ES MS Electrospray mass spectrometry
Et$_2$O diethyl ether
EtOH ethanol
EtOAc, EA ethyl acetate
h hours
HPLC high performance liquid chromatography
KOAc potassium acetate
LCMS Liquid chromatography mass spectroscopy
mCPBA meta-chloro perbenzoic acid
MeNO$_2$ nitromethane
MeOH methanol
NBS N-bromosuccinimide
NCS N-chlorosuccinimide
NIS N-iodosuccinimide
NXS N-halosuccinimide
NaBH(OAc)$_3$ sodium triacetoxyborohydride
NMR Nuclear Magnetic Resonance spectroscopy
PE petroleum ether
PPh$_3$ triphenylphosphine
rt or r.t. room temperature
RT retention time
SFC supercritical fluid chromatography
t-BuOMe methyl t-butyl ether
TFA trifluoroacetic acid
THF tetrahydrofuran
uv ultraviolet

EXAMPLES

The following examples illustrate the invention. These Examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Reactions involving metal hydrides including lithium hydride, lithium aluminium hydride, di-isobutylaluminium hydride, sodium hydride, sodium borohydride and sodium triacetoxyborohydride are carried out under argon unless otherwise specified.

SYNTHESIS

Example 1 3-bromo-7,8-dihydro-2H-1,6,9-trioxa-9a-borabenzo[cd]azulen-2-yl)methanamine hydrochloride (G1-Br)

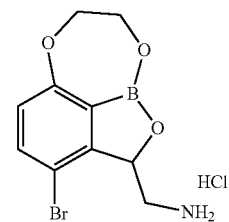 [SMILES: NCC1OB2OCCOc3ccc(Br)c1c32 ; Cl]

(a) 2-bromo-3-hydroxybenzaldehyde

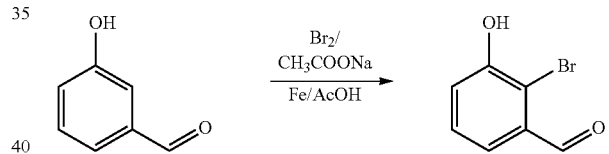

A suspension of 3-hydroxybenzaldehyde (5 g, 40 mmol), iron powder (172 mg, 3 mmol) and sodium acetate (6.72 g, 80 mmol) in acetic acid (40 mL) was warmed until a clear solution was obtained and then cooled to room temperature. To this mixture was added dropwise a solution of bromine (7.2 g, 45 mmol) in glacial acetic acid (10 mL) over 15 min. After the addition, the reaction mixture was stirred for 2 h and then poured into ice-water. The resulting mixture was extracted with dichloromethane (3×50 mL). The combined extracts were dried over anhydrous Na$_2$SO$_4$ and concentrated. The residue was re-crystallized from dichloromethane to afford the product (2.3 g, 28%). $^1$H NMR (300 MHz, DMSO-d$_6$): δ 10.75 (s, 1H), 10.26 (s, 1H), 7.38-7.24 (m, 3H).

(b) 2-bromo-3-(2-((tetrahydro-2H-pyran-2-yl)oxy)ethoxy)benzaldehyde

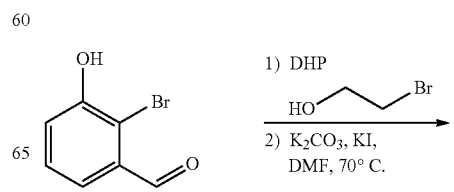

-continued

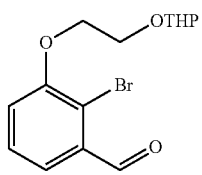

Dihydropyran (1.26 g, 15 mmol) was added dropwise at 0° C. to 2-bromoethanol (1.875 g, 15 mmol). The mixture was stirred 30 min at 0° C. and then 2 h at rt. 2-bromo-3-hydroxy benzaldehyde (2 g, 10 mmol) was added to this mixture, followed by potassium carbonate (1.518 g, 11 mmol), potassium iodide (332 mg, 2 mmol) and dry DMF (20 mL). The reaction was stirred at 70° C. overnight. The solution was cooled to rt and diluted with diethyl ether (100 mL). The inorganic salts were removed by filtration and the filtrate was diluted with hexanes (100 mL). The organic layer was washed with water (50 mL×3), and then concentrated to dryness under reduced pressure. The residue was purified by column chromatography on silica gel using ethyl acetate and petroleum ether as eluents to give the target compound (3 g, 92%) as a yellow oil. MS (ESI) m/z=351 [M+23]$^+$, Rf=0.7 (PE:EA=3).

$^1$H NMR (300 MHz, DMSO-d$_6$): δ 10.29 (s, 1H), 7.50-7.41 (m, 3H), 4.75 (s, 1H), 4.31-4.28 (m, 2H), 4.00-3.94 (m, 1H), 3.82-3.75 (m, 2H), 3.47-3.43 (m, 1H), 1.73-1.50 (m, 6H).

(c) 3-(2-((tetrahydro-2H-pyran-2-yl)oxy)ethoxy)-2-(4,4,5,5-tetramethyl-1,3,2-dioxaborolan-2-yl)benzaldehyde

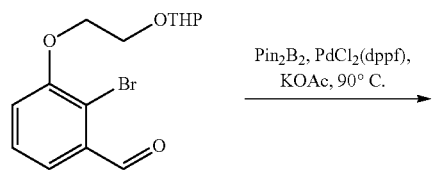

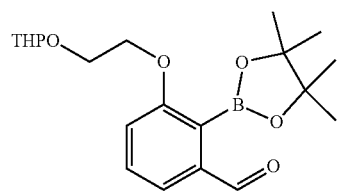

A solution of 2-bromo-3-(2-(tetrahydro-2H-pyran-2-yloxy)ethoxy)benzaldehyde (160 g, 0.49 mol), 4,4,4',4',5,5,5',5'-octamethyl-2,2'-bi(1,3,2-dioxaborolane) (249 g, 0.98 mol), Pd(dppf)Cl$_2$ (20 g, 24.5 mmol) and KOAc (144 g, 1.47 mol) in DMF (2.0 L) was stirred at 90° C. overnight. Then the reaction mixture was treated with water (4 L) and then extracted with EtOAc (3×1.5 L). The combined organic layers were washed with brine (250 mL), dried over anhydrous Na$_2$SO$_4$ and concentrated to dryness in vacuo. The residue was purified by column chromatography on silica gel (petroleum ether: ethyl acetate=10:1 to 2:1) to give the target compound as a yellow oil (88 g, yield 48%). MS (ESI) m/z=317 [M+H]$^+$, Rf=0.4 (PE:EA=3). $^1$H NMR (300 MHz, DMSO-d$_6$): δ 9.88 (s, 1H), 7.60-7.51 (m, 2H), 7.31-7.28 (d, 1H), 4.64-4.63 (m, 1H), 4.16-4.13 (m, 2H), 4.00-3.94 (m, 1H), 3.82-3.75 (m, 2H), 3.47-3.43 (m, 1H), 1.73-1.50 (m, 6H), 1.29 (m, 12H).

(d) 2-(nitromethyl)-7,8-dihydro-2H-1,6,9-trioxa-9a-borabenzo[cd]azulene

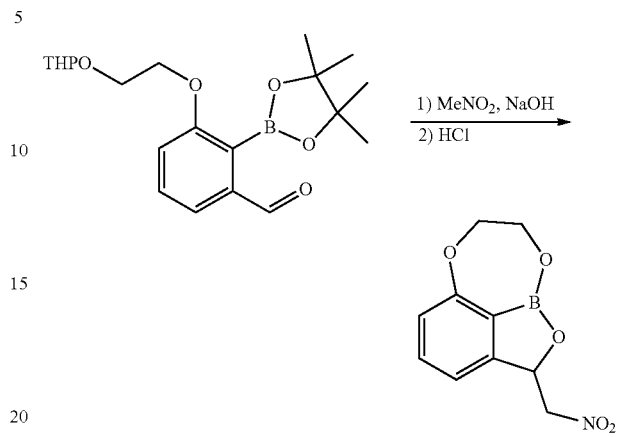

To a solution of NaOH (4.8 g, 0.12 mol) in water (100 mL) was added nitromethane (18.3 g, 0.3 mol) at 5-10° C. After stirring for 15 min at 5-10° C., cetyltrimethylammonium bromide (CTAB) (2.2 g, 6 mmol) was added to the reaction mixture and followed by the addition of 3-(2-(tetrahydro-2H-pyran-2-yloxy)ethoxy)-2-(4,4,5,5-tetramethyl-1,3,2-dioxaborolan-2-yl)benzaldehyde (45 g, 0.12 mol) at 5-10° C. The reaction mixture was stirred at rt for 5 h. The reaction mixture was acidified to pH=1 using diluted hydrochloric acid and stirred at rt overnight. The reaction mixture was filtered to give the target compound (14.5 g, 51%) as a white solid. $^1$H NMR (300 MHz, DMSO-d$_6$): δ 7.50-7.45 (t, 1H), 7.16-7.13 (d, 1H), 6.91-6.88 (d, 1H), 5.91-5.88 (m, 1H), 5.37-5.31 (m, 1H), 4.69-4.61 (m, 2H), 4.41-4.14 (m, 3H).

(e) (7,8-dihydro-2H-1,6,9-trioxa-9a-borabenzo[cd]azulen-2-yl)methanamine hydrochloride

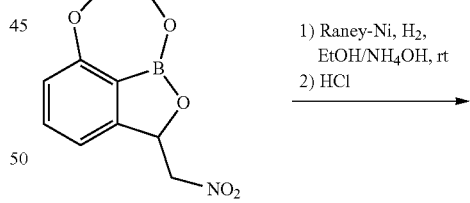

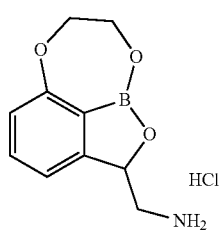

A solution of 2-(nitromethyl)-7,8-dihydro-2H-1,6,9-trioxa-9a-borabenzo[cd]azulene (1.5 g, 6.4 mmol), Raney Ni (200 mg) and 2 M NH$_3$ in EtOH (5 mL) in ethanol (40 mL) was shaken under an atmosphere of H2 for 2 h at rt. The mixture was filtered through a bed of Celite and the filtrate was concentrated in vacuo. The crude amine was dissolved in EtOH (20 mL) and a saturated solution of HCl (gas) in Et₂O (30 mL) was added immediately. After 1 h, the suspension was filtered and the resulting solid was washed with acetonitrile/hexanes (2:1, 2×20 mL) to give the compound as a white solid (700 mg, 45%). MS (ESI) m/z=206/224 [M+H]⁺.

(f) tert-butyl ((7,8-dihydro-2H-1,6,9-trioxa-9a-borabenzo[cd]azulen-2-yl)methyl)carbamate

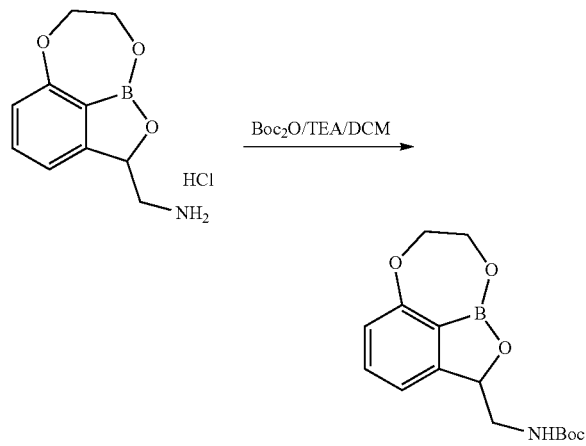

To a mixture of (7,8-dihydro-2H-1,6,9-trioxa-9a-borabenzo[cd]azulen-2-yl)methanamine hydrochloride (700 mg, 2.9 mmol) and triethylamine (878.7 mg, 8.7 mmol) in dichloromethane (10 mL) at 0° C. was added di-tert-butyl dicarbonate (948 mg, 4.35 mmol) and the mixture was stirred for 2 h at room temperature. The reaction was quenched with sat. NaHCO₃ (15 mL) and the resulting mixture was extracted with EtOAc (3×20 mL). The combined organic layers were dried over anhydrous Na₂SO₄ and concentrated in vacuo. The residue was purified by flash-column chromatography using ethyl acetate and petroleum ether as eluents to give the desired product (500 mg, 56%). MS (ESI) m/z=250 [M−56]⁺.

(g) tert-butyl ((3-bromo-7,8-dihydro-2H-1,6,9-trioxa-9a-borabenzo[cd]azulen-2-yl)methyl)carbamate

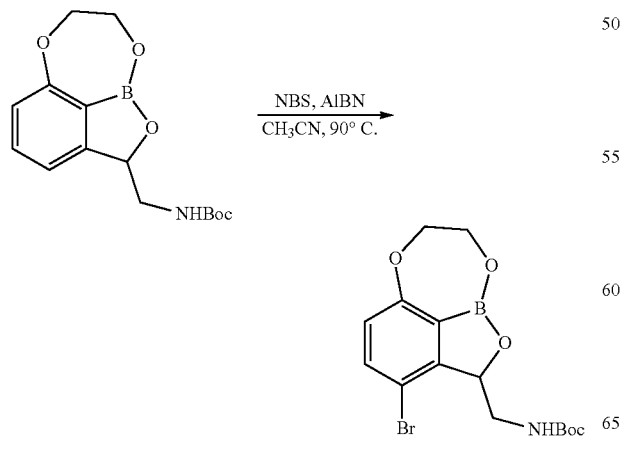

To a solution of tert-butyl ((7,8-dihydro-2H-1,6,9-trioxa-9a-borabenzo[cd]azulen-2-yl)methyl)carbamate (0.5 mg, 1.64 mmol) and NBS (354 mg, 2.0 mmol) in acetonitrile (15 mL) was added AIBN (27 mg) and the mixture was stirred for 1 h at 90° C. The reaction mixture was then concentrated under vacuum and the residue was purified by preparatory-HPLC to give the desired product (300 mg, 50%). MS (ESI) m/z=328/330 [M−56]⁺.

(h) Title Compound

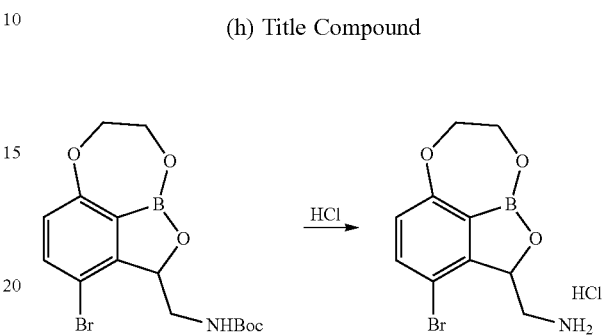

A mixture of tert-butyl ((3-bromo-7,8-dihydro-2H-1,6,9-trioxa-9a-borabenzo[cd]azulen-2-yl)methyl)carbamate (0.2 g, 0.522 mmol) in saturated HCl (gas) in Et₂O (10 mL) was stirred at rt for 1 h and concentrated to dryness (water bath temperature <30° C.). The residue was triturated with acetonitrile (2×5 mL) and the white solid was dried under high vacuum to give the product (140 mg, 83%) as a white solid. ¹H NMR (300 MHz, DMSO-d₆): δ 8.36 (s, 3H), 7.64-7.61 (d, 1H), 6.93-6.90 (d, 1H), 5.51-5.49 (d, 1H), 4.69 (m, 1H), 4.36-4.23 (m, 3H), 3.62 (m, 1H), 3.05-3.01 (m, 1H). MS (ESI) m/z=284/286 [M+H]⁺.

Example 2 (S)-(3-bromo-7,8-dihydro-2H-1,6,9-trioxa-9a-borabenzo[cd]azulen-2-yl)methanamine hydrochloride (G2-Br)

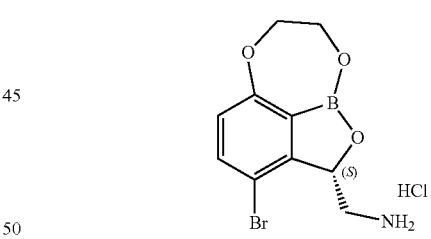

Method A (a) Title Compound

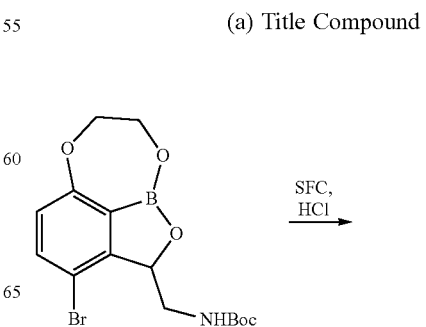

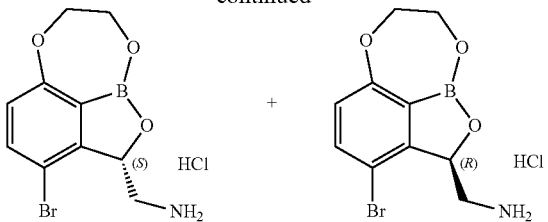

The racemic compound tert-butyl((3-bromo-7,8-dihydro-2H-1,6,9-trioxa-9a-borabenzo[cd]azulen-2-yl)methyl)carbamate (Example 1, (g)) was separated via supercritical fluid chromatography (SFC) (chiral column CHIRALCEL OJ-H, eluted with MeOH (15%) and $CO_2$ (85%) and two chiral compounds (S)-tert-butyl ((3-bromo-7,8-dihydro-2H-1,6,9-trioxa-9a-borabenzo[cd]azulen-2-yl)methyl)carbamate (second eluting isomer, RT=3.8 min) and (R)-isomer tert-butyl ((3-bromo-7,8-dihydro-2H-1,6,9-trioxa-9a-borabenzo[cd]azulen-2-yl)methyl)carbamate (first eluting isomer, RT=3.3 min) were obtained. Each of the chiral compounds (1.2 g, 3.13 mmol) in saturated HCl (gas) in $Et_2O$ (20 mL) was stirred at room temperature for 1 h and concentrated to dryness (water bath <30° C.). The residue was washed with acetonitrile (2×5 mL) and the white solid was dried under high vacuum to give the product (900 mg, 90%) as a white solid. MS (ESI) m/z=284/286 $[M+H]^+$.

(S)-(3-bromo-7,8-dihydro-2H-1,6,9-trioxa-9a-borabenzo[cd]azulen-2-yl)methanamine hydrochloride $^1$H NMR (300 MHz, DMSO-$d_6$): δ 8.40 (s, 3H), 7.63-7.61 (d, 1H), 6.92-6.89 (d, 1H), 5.50-5.48 (d, 1H), 4.68 (m, 1H), 4.35-4.22 (m, 3H), 3.60 (m, 1H), 3.00 (m, 1H).

(R)-(3-bromo-7,8-dihydro-2H-1,6,9-trioxa-9a-borabenzo[cd]azulen-2-yl)methanamine hydrochloride $^1$H NMR (300 MHz, DMSO-$d_6$): δ 8.30 (s, 3H), 7.64-7.61 (d, 1H), 6.93-6.90 (d, 1H), 5.51-5.49 (d, 1H), 4.68 (m, 1H), 4.36-4.23 (m, 3H), 3.61 (m, 1H), 3.05-3.01 (m, 1H).

Method B (a) (S)-tert-butyl ((3-bromo-7,8-dihydro-2H-1,6,9-trioxa-9a-borabenzo[cd]azulen-2-yl)methyl)carbamate

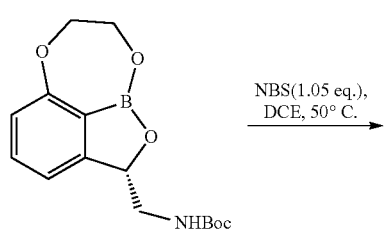

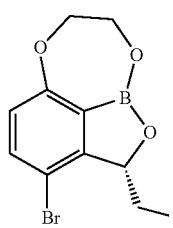

A mixture of (S)-tert-butyl ((7,8-dihydro-2H-1,6,9-trioxa-9a-borabenzo[cd]azulen-2-yl)methyl)carbamate (110.0 g, 360.50 mmol) (Example 4, Method B, (h)) and NBS (67.4 g, 378.53 mmol) in DCE (1.1 L) was heated at 50° C. for 6 h. The solution was washed with hot water (1 L) three times and the organic solution was concentrated under vacuum to obtain the desired product (132.0 g, crude) as a yellow gum (used in next step without purification). $^1$H NMR (400 MHz, DMSO-$d_6$): 7.57-7.55 (d, J=8 Hz, 1H), 6.96 (s, 1H), 6.85-6.83 (d, J=8 Hz, 1H), 5.25 (m, 1H), 4.71-4.69 (m, 1H), 4.34-4.07 (m, 3H), 3.76-3.69 (m, 1H), 3.17-3.16 (m, 1H), 1.33 (s, 9H). LC-MS: [M−55]=327.8.

(b) Title Compound

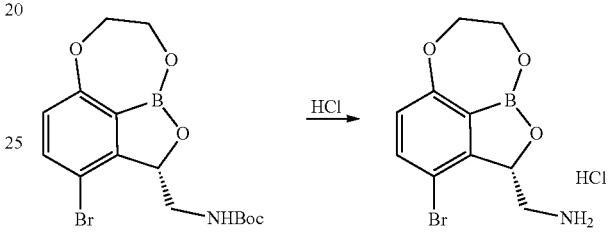

A solution of (S)-tert-butyl ((3-bromo-7,8-dihydro-2H-1,6,9-trioxa-9a-borabenzo[cd]azulen-2-yl)methyl)carbamate (130.0 g, crude) and conc. HCl (100 mL) in 1,4-dioxane (500 mL) was stirred at r.t. for 8 h, during which time colorless solids were precipitated and filtered and washed with 2-propanol (200 mL). The solid was dried under vacuum at 50° C. for 6 h to obtain the hydrochloride salt of desired product (60.0 g, 51.9% total yield over two steps) as a colorless solid. $^1$H NMR (400 MHz, DMSO-$d_6$): 8.45 (s, 3H), 7.64-7.62 (d, J=8, 1H), 6.92-6.90 (d, J=8, 1H), 5.52 (m, 1H), 4.69 (m, 1H), 4.37-4.15 (m, 3H), 3.74-3.50 (m, 1H), 3.05-2.95 (m, 1H). $^{13}$C NMR (400 MHz, DMSO-$d_6$): 161.80, 151.28, 137.57, 118.64, 107.18, 80.04, 73.86, 69.18, 41.88. LC-MS: $[M+1]^+$=283.9.

Example 3 3-chloro-7,8-dihydro-2H-1,6,9-trioxa-9a-borabenzo[cd]azulen-2-yl)methanamine hydrochloride (G3-Cl)

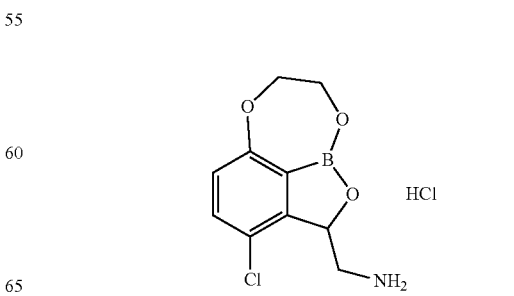

(a) 3-chloro-2-(nitromethyl)-7,8-dihydro-2H-1,6,9-trioxa-9a-borabenzo[cd]azulene

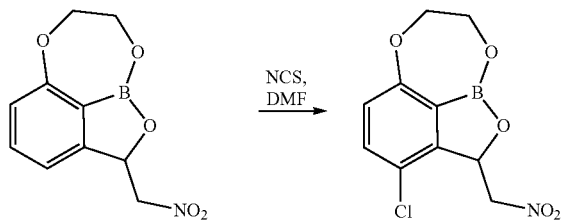

To a solution of 2-(nitromethyl)-7,8-dihydro-2H-1,6,9-trioxa-9a-borabenzo[cd]azulene (29 g, 123.4 mmol) (Example 1, (d)) in DMF (250 mL) at 80° C. was added a solution of NCS (16.5 g, 123.4 mmol) in DMF (100 mL). The mixture was stirred for 30 min at 80° C. The reaction mixture was poured into ice-water and extracted with EtOAc (200 mL×3). The combined organic layers were washed with brine, dried over Na$_2$SO$_4$, filtered and concentrated under reduced pressure. The residue was purified by recrystallization from petroleum ether/ethyl acetate (10:1) to give 24 g of crude product. MS (ESI) m/z=270 [M+H]$^+$. $^1$H NMR (300 MHz, DMSO-d$_6$): δ 7.52-7.49 (d, 1H), 6.99-6.96 (d, 1H), 5.96-5.93 (m, 1H), 5.42-5.30 (m, 1H), 4.80-4.61 (m, 2H), 4.43-4.17 (m, 3H).

(b) Title Compound

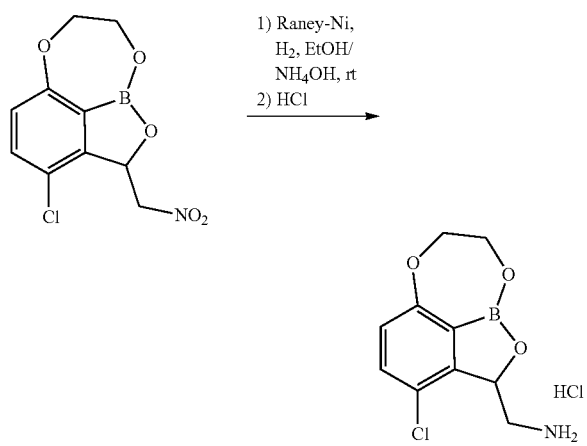

A solution of 3-chloro-2-(nitromethyl)-7,8-dihydro-2H-1,6,9-trioxa-9a-borabenzo[cd]azulene (24 g, 89.22 mmol), Raney Ni (4.0 g) and 7 M NH$_3$ in MeOH (20 mL) in methanol (300 mL) was shaken under an atmosphere of H$_2$ for 2 h at rt. The mixture was filtered through a bed of Celite and the filtrate was concentrated under vacuum. The crude amine was dissolved in MeOH (20 mL) and concentrated HCl (5 mL) was added. The resulting mixture was stirred at rt for 1 h and then concentrated under reduced pressure. The resulting solid was washed with acetonitrile/hexanes (2:1, 2×200 mL) to give the desired product (12 g, 50%) as a white solid. $^1$H NMR (300 MHz, DMSO-d$_6$): δ 8.19 (s, 3H), 7.51-7.48 (d, 1H), 6.99-6.96 (d, 1H), 5.56-5.54 (d, 1H), 4.69 (m, 1H), 4.36-4.23 (m, 3H), 3.58 (m, 1H), 3.05-3.01 (m, 1H). MS (ESI) m/z=240 [M+H]$^+$.

Example 4-1 (S)-(3-chloro-7,8-dihydro-2H-1,6,9-trioxa-9a-borabenzo[cd]azulen-2-yl)methanamine hydrochloride (G4-Cl)

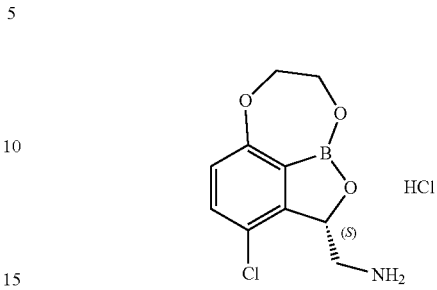

Method A (a) tert-butyl ((3-chloro-7,8-dihydro-2H-1,6,9-trioxa-9a-borabenzo[cd]azulen-2-yl)methyl)carbamate

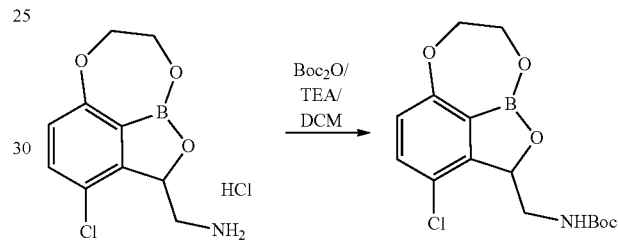

To a mixture of (3-chloro-7,8-dihydro-2H-1,6,9-trioxa-9a-borabenzo[cd]azulen-2-yl)methanamine hydrochloride (8.0 g, 33.7 mmol) (Example 3, (b)) and triethylamine (10.2 g, 101.2 mmol) in dichloromethane (250 mL) at 0° C. was added di-tert-butyl dicarbonate (11 g, 50.6 mmol) and the mixture was stirred for 2 h at rt. The reaction was quenched with sat. NaHCO$_3$ (150 mL) and the resulting mixture was extracted with EtOAc (2×200 mL). The combined organic layers were dried over anhydrous Na$_2$SO$_4$ and concentrated under vacuum. The residue was purified by preparative-HPLC using Daisogel 10μ C18 column (250×50 mm) and eluted with gradient water/acetonitrile (0.05% TFA) to give the desired product (4.6 g, 47%). MS (ESI) m/z=284 [M−56]$^+$.

(b) Title Compound

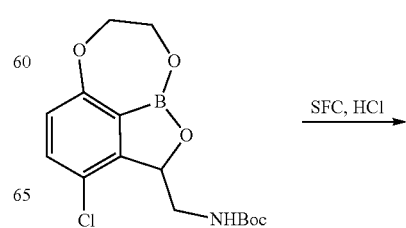

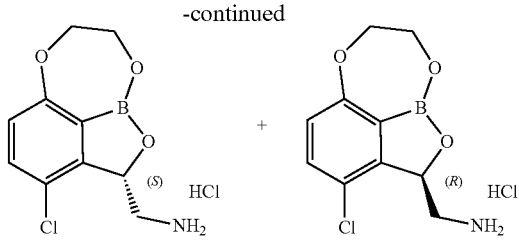

The racemic compound tert-butyl ((3-chloro-7,8-dihydro-2H-1,6,9-trioxa-9a-borabenzo[cd]azulen-2-yl)methyl)carbamate was separated via SFC (chiral column CHIRALCEL OJ-H) eluted with EtOH (15%) and CO$_2$ (85%) and the two chiral compounds (S)-tert-butyl ((3-chloro-7,8-dihydro-2H-1,6,9-trioxa-9a-borabenzo[cd]azulen-2-yl)methyl)carbamate (second eluting isomer, RT=2.9 min) and (R)-tert-butyl ((3-chloro-7,8-dihydro-2H-1,6,9-trioxa-9a-borabenzo[cd]azulen-2-yl)methyl)carbamate (first eluting isomer, RT=2.6 min) were obtained. Each of the chiral compounds (4.6 g, 13.6 mmol) was stirred at rt in 80 mL of saturated HCl (gas) in Et$_2$O for 1 h and concentrated to dryness (water bath temperature <30° C.). The residue was triturated with acetonitrile (2×5 mL) and the white solid was dried under high vacuum to give the two products (S)-(3-chloro-7,8-dihydro-2H-1,6,9-trioxa-9a-borabenzo[cd]azulen-2-yl)methanamine hydrochloride (1.2 g) and (R)-(3-chloro-7,8-dihydro-2H-1,6,9-trioxa-9a-borabenzo[cd]azulen-2-yl)methanamine hydrochloride (2.3 g) respectively as white solids. MS (ESI) m/z=240 [M+H]$^+$.

(S)-(3-chloro-7,8-dihydro-2H-1,6,9-trioxa-9a-borabenzo[cd]azulen-2-yl)methanamine hydrochloride $^1$H NMR (300 MHz, DMSO-d$_6$): δ 8.30 (s, 3H), 7.51-7.48 (d, 1H), 6.99-6.96 (d, 1H), 5.59-5.57 (d, 1H), 4.68 (m, 1H), 4.36-4.23 (m, 3H), 3.58 (s, 1H), 3.03-2.99 (m, 1H).

G4-Cl—(R) (R)-(3-chloro-7,8-dihydro-2H-1,6,9-trioxa-9a-borabenzo[cd]azulen-2-yl)methanamine hydrochloride $^1$H NMR (300 MHz, DMSO-d$_6$): δ 8.28 (s, 3H), 7.51-7.48 (d, 1H), 6.99-6.96 (d, 1H), 5.58-5.56 (d, 1H), 4.69 (m, 1H), 4.36-4.23 (m, 3H), 3.59 (m, 1H), 3.05-3.01 (m, 1H).
Method B (a) (Z)-1-(pyridin-2-yl)-N-((1R)-1,7,7-trimethylbicyclo[2.2.1]heptan-2-ylidene)methanamine

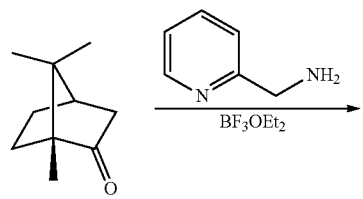

A mixture of (+)-camphor (371 g, 2.44 mol), pyridin-2-ylmethanamine (277 g, 2.56 mol) and BF$_3$.Et$_2$O (17 g, 0.12 mol) in toluene (3.7 L) was charged into a 5 L round bottom flask equipped with a Dean Stark trap, reflux condenser, thermometer and nitrogen inlet. The mixture was heated to reflux with azeotropic removal of water for 20 h. The mixture was cooled to 15° C. and quenched with 5% aqueous sodium bicarbonate (2.5 L), the organic phase was separated and washed with water (1.25 L×2), then the mixture was concentrated down to 2 L under vacuum. The residue was used in next step without purification. $^1$H NMR (400 MHz, DMSO-d$_6$): 8.47-8.48 (d, J=4.4 Hz, 1H), 8.77-8.74 (t, J=7.6 Hz, 1H), 7.43-7.41 (d, J=8.0 Hz, 1H), 7.25-7.22 (dd, J=4.8 Hz, 1H), 4.49-4.38 (dd, J=16.4 Hz, 2H), 2.46-2.42 (m, 1H), 1.97-1.93 (m, 2H), 1.84-1.79 (m, 1H), 1.71-1.64 (m, 1H), 1.33-1.22 (m, 2H), 0.93 (s, 3H), 0.92 (s, 3H), 0.73 (s, 3H). LCMS: [M+H]$^+$=243.

(b) (1R)-1,7,7-trimethyl-N-(pyridin-2-ylmethyl)bicyclo[2.2.1]heptan-2-amine

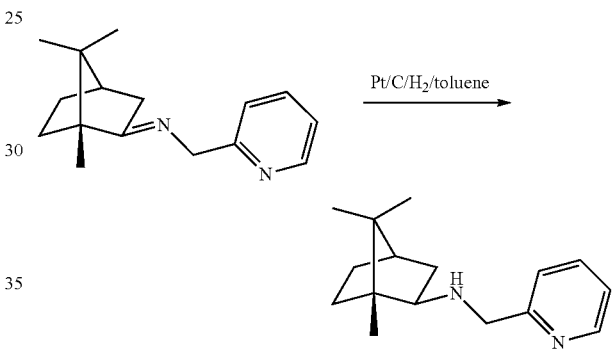

5% Pt/C (40 g) was charged into a 5 L pressure vessel, followed by a solution of (Z)-1-(pyridin-2-yl)-N-((1R)-1,7,7-trimethylbicyclo[2.2.1]heptan-2-ylidene)methanamine (2.44 mol) in toluene (2 L). The vessel was pressurized with 100 psi hydrogen for a period of 12 h. The solid was filtered through Celite® and the cake was washed with toluene (1 L). The filtrate was concentrated under vacuum to obtain the desired product (435 g obtained, total yield: 73%, over two steps) as a pale yellow oil. $^1$H NMR (400 MHz, DMSO-d$_6$): 8.49-8.48 (d, J=4.8 Hz, 1H), 7.75-7.71 (t, J=7.6 Hz, 1H), 7.40-7.38 (d, J=7.6 Hz, 1H), 7.24-7.21 (dd, J=5.2 Hz, 1H), 3.79-3.64 (dd, J=14.4 Hz, 2H), 2.53-2.49 (m, 1H), 1.99 (s, 1H), 1.68-1.42 (m, 5H), 1.05 (s, 3H), 0.87 (s, 3H), 0.78 (s, 3H), LCMS: [M+H]$^+$=245.

(c) 3-(2-(benzyloxy)ethoxy)benzaldehyde

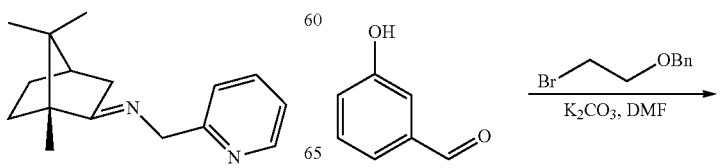

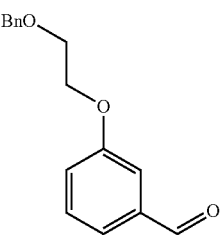

To a solution of 3-hydroxybenzaldehyde (2.90 kg, 23.75 mol), and ((2-bromoethoxy)methyl)benzene (4.26 kg, 19.79 mol) in DMF (9.3 L) was added $K_2CO_3$ (3.83 kg, 27.70 mol). The reaction mixture was stirred at r.t. for 24 h. Water (15 L) and tert-butyl methyl ether (23 L) were added to the reaction mixture. The organic phase was separated and washed with 1N NaOH (2×15 L) and water (15 L) sequentially, and then concentrated to a minimum. Ethanol (23 L) was added and the solution was concentrated under vacuum to afford the desired product (4.7 kg, 93%) as a colourless oil. $^1$H NMR (400 MHz, DMSO-$d_6$): 9.98 (s, 1H), 7.55-7.52 (m, 2H), 7.46 (s, 1H), 7.36-7.34 (m, 4H), 7.32-7.26 (m, 2H), 4.57 (s, 2H), 4.25-4.22 (t, J=4.4 Hz, 2H), 3.80-3.78 (t, J=4.4 Hz, 2H). LCMS: [M+Na]$^+$=279.

(d) (S)-1-(3-(2-(benzyloxy)ethoxy)phenyl)-2-nitroethanol

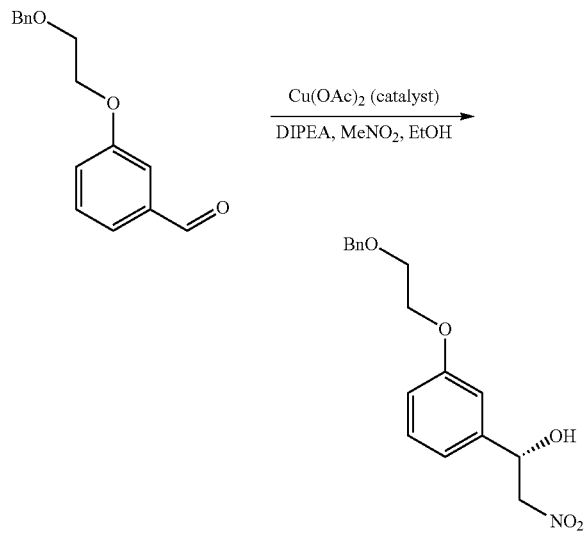

A mixture of copper (II) acetate (167 g, 0.92 mol), (1R)-1,7,7-trimethyl-N-(pyridin-2-ylmethyl)bicyclo[2.2.1]heptan-2-amine (269 g, 1.10 mol) in ethanol (19 L) was stirred at r.t. for 1 h, then a solution of 3-(2-(benzyloxy)ethoxy)benzaldehyde (4.70 kg, 18.34 mol) in ethanol (5 L) was added. The reaction mixture was cooled to a temperature range between −30° C. and −40° C., and then nitromethane (9.9 L, 183.40 mol) was added dropwise, keeping the temperature below −30° C., followed by the addition of diisopropylethylamine (285 g, 2.20 mol). The reaction was stirred at −30° C. for 24 h, and then quenched with trifluoroacetic acid (314 g, 2.75 mol). 1 N HCl (24 L) and TBME (47 L) were added to the resulting solution. The separated organic phase was washed with water (24 L) and then concentrated under vacuum. The residue was added to a mixture of petroleum ether/ethyl acetate=5:1 (10 L). Then the yellow solid was precipitated, and collected by filtration with Buchner funnel and dried under vacuum at 40° C. for 6 h to afford the desired product (5.00 kg, 86%) as a white solid. $^1$H NMR (400 MHz, DMSO-$d_6$): 7.38-7.25 (m, 6H), 7.03 (s, 1H), 7.01-6.99 (d, J=7.6 Hz, 1H), 6.90-6.87 (dd, J=8.0 Hz, 1H), 6.09-6.08 (d, J=5.2 Hz, 1H), 5.26-5.22 (m, 1H), 4.86-4.82 (dd, J=12.4 Hz, 1H), 4.57-4.51 (m, 3H), 4.15-4.13 (m, 2H), 3.78-3.76 (t, J=4.8 Hz, 2H). LC-MS: [M+Na]$^+$=340.

(e) (S)-1-(3-(2-(benzyloxy)ethoxy)phenyl)-2-(dibenzylamino)ethanol hydrochloride

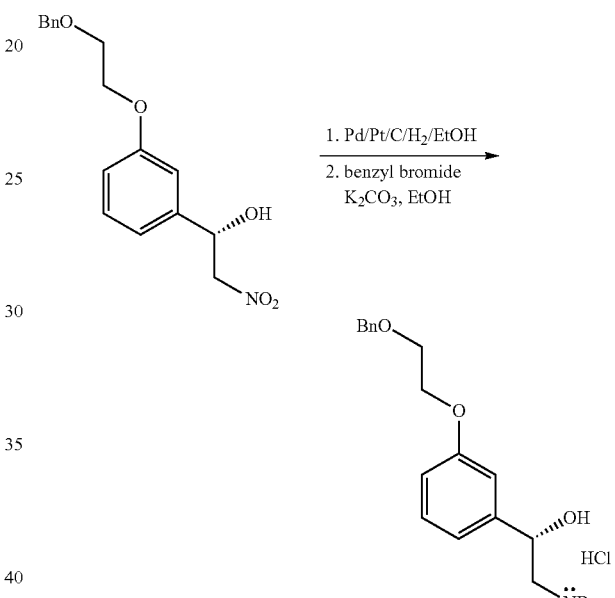

10% Pd/C (800 g) and 10% Pt/C (200 g) were charged to a pressure vessel, followed by a solution of (S)-1-(3-(2-(benzyloxy)ethoxy)phenyl)-2-nitroethanol (5.00 kg, 15.76 mol) in ethanol (50 L). The vessel was pressurized with 100 psi hydrogen for 12 h at r.t. The solid was filtered through Celite® and the cake was washed with ethanol (5 L). To the filtrate, $K_2CO_3$ (4.80 kg, 34.67 mol) and benzyl bromide (5.93 kg, 34.67 mol) were added sequentially. The reaction mixture was stirred at r.t. for 24 h. The solid was filtered and washed with ethanol (1 L). The filtrate was diluted with water (20 L) and then heated to 50° C. The solution was stirred at 50° C. for 30 min and then conc. HCl (1.5 L) was added dropwise over 1 h. The mixture was cooled to 0° C. and held at 0° C. for additional 30 min. The product was filtered and washed with 20% aqueous ethanol (1 L) to afford the hydrochloric salt of desired product (5.00 kg, 63% over two steps) as a colourless solid. $^1$H NMR (400 MHz, DMSO-$d_6$): 10.67 (s, 1H), 7.72-7.68 (m, 4H), 7.47-7.45 (m, 6H), 7.38-7.26 (m, 5H), 7.25-7.21 (t, J=7.6 Hz, 1H), 6.86-6.84 (d, J=8.0 Hz, 1H), 6.77 (s, 1H), 6.77-6.75 (d, J=7.2 Hz, 1H), 6.36 (s, 1H), 5.04-5.02 (d, J=9.2 Hz, 1H), 4.58 (s, 2H), 4.51-4.38 (m, 4H), 4.09-4.07 (t, J=4.0 Hz, 2H), 3.77-3.75 (t, J=3.2 Hz, 2H), 3.13-2.96 (m, 2H). LC-MS: [M+H]$^+$=468.

(f) (S)-7-(2-(benzyloxy)ethoxy)-3-((dibenzylamino)methyl)benzo[c][1,2]oxaborol-1(3H)-ol

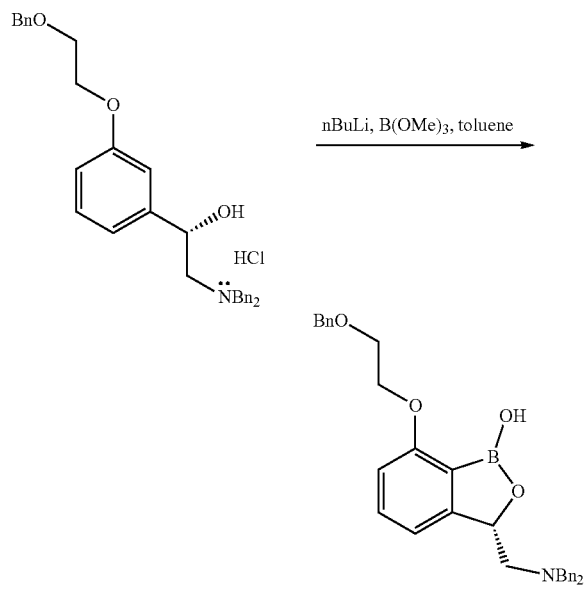

To a −30° C. solution of (S)-1-(3-(2-(benzyloxy)ethoxy)phenyl)-2-(dibenzylamino)ethanol hydrochloride (3.85 kg, 7.64 mol) in dry toluene (39 L) under $N_2$ atmosphere was added n-BuLi (15.3 L, 38.20 mol) dropwise over 6 h. After addition, the mixture was stirred at −30° C. for another 1 h, and then cooled to −70° C.; trimethyl borate (3.97 kg, 38.20 mol) was added dropwise keeping the temperature below −60° C. After addition, the reaction mixture was allowed to warm to r.t. and stirred overnight. The reaction was quenched with 5% aqueous $NaHCO_3$ (20 L) and stirred vigorously for 15 min, the resulting suspension was filtered and the filtrate was separated. The organic layer was washed with water (20 L×3) and concentrated under vacuum and the residue was purified by gel chromatography eluting with petroleum ether/ethyl acetate=5:1 to afford desired product (1.80 kg, 48%) as a yellow solid. $^1$H NMR (400 MHz, DMSO-$d_6$): 8.81 (s, 1H), 7.39-7.22 (m, 16H), 6.82-6.80 (d, J=7.6 Hz, 1H), 6.72-6.70 (d, J=7.6 Hz, 1H), 5.34-5.31 (dd, J=7.6 Hz, 1H), 4.60 (s, 2H), 4.22-4.19 (t, J=4.4 Hz, 2H), 3.80-3.72 (m, 6H), 2.88-2.84 (dd, J=13.6 Hz, 1H), 2.47-2.45 (dd, J=10 Hz, 1H). LC-MS: [M+H]$^+$=494.

(g) (S)-(7,8-dihydro-2H-1,6,9-trioxa-9a-borabenzo[cd]azulen-2-yl)methanamine hydrochloride

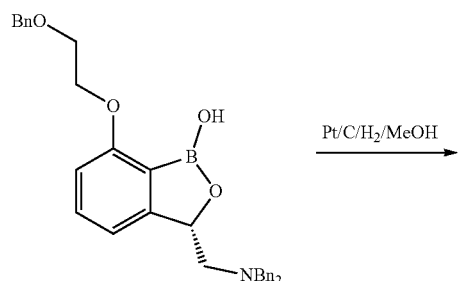

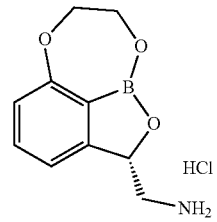

10% Pd/C (180 g) was charged to a pressure vessel, followed by a solution of (S)-7-(2-(benzyloxy)ethoxy)-3-((dibenzylamino)methyl)benzo[c][1,2]oxaborol-1(3H)-ol (1.80 kg, 3.65 mol) in methanol (18 L), toluene (3.6 L) and 1 N HCl (4 L). The vessel was pressurized with 100 psi hydrogen for a period of 12 h at 50° C. The solid was filtered through Celite and the cake was washed with methanol (1 L). The filtrate was concentrated under vacuum and the residue was treated with 2-propanol (3.6 L), stirred at r.t. for 30 min. The resulting solid was collected by filtration and washed with 2-propanol (500 mL), dried under vacuum at 50° C. for 6 h to afford the desired product (680 g, 77%) as a pale yellow powder.

$^1$H NMR (400 MHz, DMSO-$d_6$): 8.38 (s, 3H), 7.52-7.48 (t, J=8.0 Hz, 1H), 7.17-7.15 (d, J=7.6 Hz, 1H), 6.92-6.90 (d, J=7.6 Hz, 1H), 5.55 (m, 1H), 4.71-4.68 (m, 1H), 4.38-4.22 (m, 3H), 3.53-3.50 (m, 1H), 2.91-2.86 (m, 1H). LC-MS: [M+H]$^+$=206.

(h) (S)-tert-butyl ((7,8-dihydro-2H-1,6,9-trioxa-9a-borabenzo[cd]azulen-2-yl)methyl)carbamate

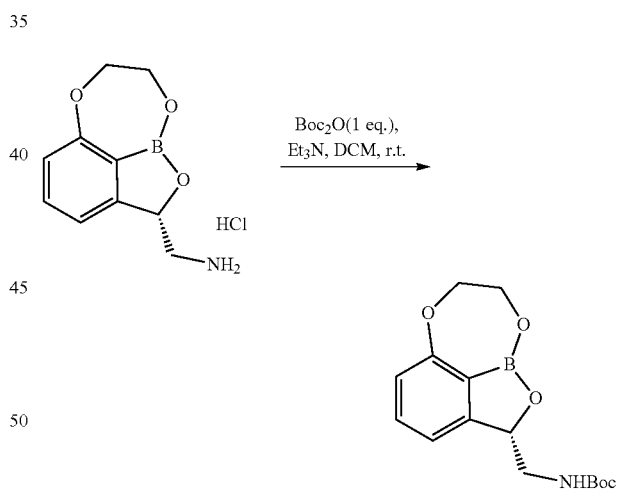

To a solution of (S)-(7,8-dihydro-2H-1,6,9-trioxa-9a-borabenzo[cd]azulen-2-yl)methanamine hydrochloride (390 g, 1.62 mol) and $Et_3N$ (163.4 g, 4.85 mol) in DCM (4.6 L) was added (Boc)$_2$O (353.0 g 1.62 mol) dropwise over 2 h at r.t. After addition, the reaction mixture was stirred at r.t. for another 3 h. The reaction was quenched with 1N HCl (4 L) and the organic phase was separated and washed with water (4 L), concentrated under vacuum to obtain desired product (460 g, 93%) as a pale white solid. $^1$H NMR (400 MHz, DMSO-$d_6$): 7.46-7.42 (t, J=7.6 Hz, 1H), 7.07 (s, 1H), 7.02-7.00 (d, J=7.2 Hz, 1H), 6.87-6.85 (d, J=8.0 Hz, 1H), 5.27 (m, 1H), 4.68-4.65 (m, 1H), 4.34-4.18 (m, 3H), 3.41 (s, 1H), 3.14-3.08 (m, 1H), 1.38 (s, 9H). LC-MS: [M−55]=250.

(i) (S)-tert-butyl ((3-chloro-7,8-dihydro-2H-1,6,9-trioxa-9a-borabenzo[cd]azulen-2-yl)methyl)carbamate

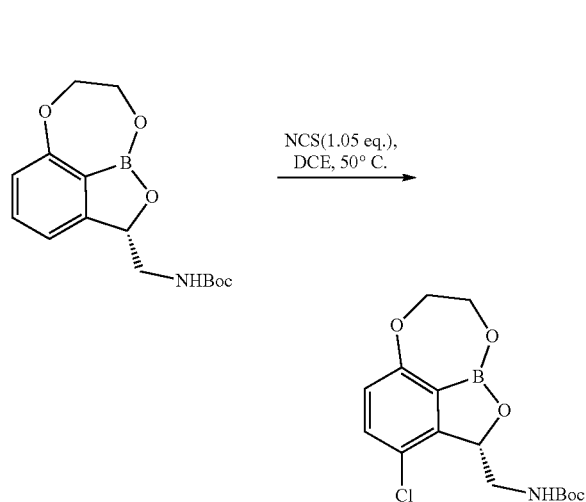

A mixture of (S)-tert-butyl ((7,8-dihydro-2H-1,6,9-trioxa-9a-borabenzo[cd]azulen-2-yl)methyl)carbamate (315.0 g, 1.03 mol) and NCS (144.5 g, 1.08 mol) in dichloroethane (3.5 L) was heated at 50° C. for 24 h. The solution was washed with hot water (50° C., 4 L×3) and the organic phase was concentrated under vacuum to obtain desired product (400.0 g, crude) as a yellow solid, which was used in the next step without further purification. $^1$H NMR (400 MHz, DMSO-$d_6$): 7.44-7.42 (d, J=8.4 Hz, 1H), 6.99 (s, 1H), 6.91-6.89 (d, J=8.4 Hz, 1H), 5.33 (m, 1H), 4.72-4.69 (m, 1H), 4.35-4.19 (m, 3H), 3.73-3.71 (m, 1H), 3.17-3.15 (m, 1H), 1.33 (s, 9H). LC-MS: [M−55]=284.

(j) Title Compound

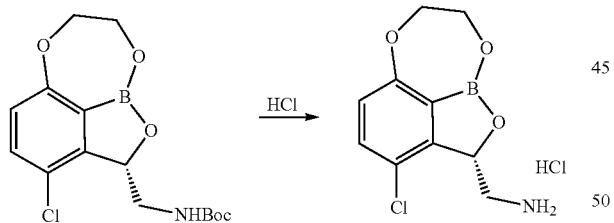

A solution of (S)-tert-butyl ((3-chloro-7,8-dihydro-2H-1,6,9-trioxa-9a-borabenzo[cd]azulen-2-yl)methyl)carbamate (400.0 g, crude) and conc. HCl (500 mL) in 1,4-dioxane (2 L) was stirred at r.t. for 8 h, during which time colourless solids were precipitated, collected and washed with 2-propanol (200 mL). The solid was recrystallized from H$_2$O and dioxane (400 mL/2000 mL) to obtain the hydrochloride salt of desired product (110.0 g, 39%, over two steps). $^1$H NMR (400 MHz, DMSO-$d_6$): 8.48-8.35 (br, 3H), 7.52-7.50 (d, J=8.8 Hz, 1H), 7.00-6.97 (d, J=8.4 Hz, 1H), 5.60 (m, 1H), 4.71 (m, 1H), 4.38-4.21 (m, 3H), 3.64-3.55 (m, 1H), 3.04-2.99 (m, 1H). $^{13}$C NMR (400 MHz, DMSO-d6): 161.22, 149.15, 134.61, 119.35, 118.31, 79.14, 73.92, 69.22, 41.88. LC-MS: [M+H]$^+$=240.

Example 4-11 (S)-(3-chloro-7,8-dihydro-2H-1,6,9-trioxa-9a-borabenzo[cd]azulen-2-yl)methanamine dihydrogensulfate.H$_2$O (G4-Cl)

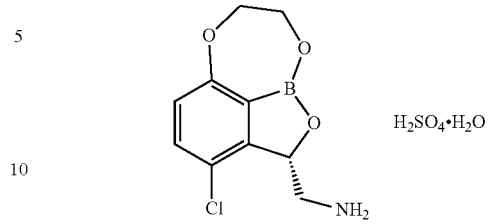

A mixture of (S)-tert-butyl ((7,8-dihydro-2H-1,6,9-trioxa-9a-borabenzo[cd]azulen-2-yl)methyl)carbamate (13.25 kg) and NCS (8.75 kg) in dichloroethane (132.5 L) was heated at 70° C. until the reaction judged complete by HPLC. The mixture was concentrated under reduced pressure, cooled to 25° C. and acetone (106 L) added. The slurry was filtered, washing with acetone (26.5 L). The wet cake was slurried in water (13.25 L) and 1,4-dioxane (66.25 L), heated to 50° C. for 20-30 minutes, cooled to 15° C., filtered and the cake washed with 1,4-dioxane (26.5 L). The wet cake was dissolved in methanol (68.9 L), filtered and the filtrate concentrated under reduced pressure. Methyl tertiary butyl ether (66.25 L) was added to the residue and the mixture concentrated under reduced pressure. Methyl tertiary butyl ether (78.7 L), isopropanol (8.7 L) and sulphuric acid (4.6 L) were added, the mixture heated to 50° C. and stirred until the sulphate content was 24.32-29.72%. The mixture was cooled to 25° C., stirred for 1 hour, filtered, the cake washed with methyl tertiary butyl ether (17.5 L) and dried to give the desired product (42%).

Example 5 (3-fluoro-7,8-dihydro-2H-1,6,9-trioxa-9a-borabenzo[cd]azulen-2-yl)methanamine hydrochloride) (G5-F)

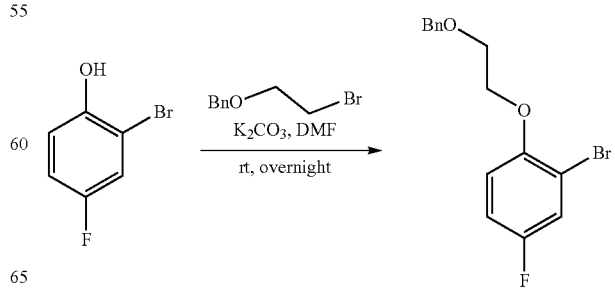

(a) 1-(2-(benzyloxy)ethoxy)-2-bromo-4-fluorobenzene

A solution of 2-bromo-4-fluorophenol (1.91 g, 10 mmol), ((2-bromoethoxy)methyl)benzene (2.6 g, 12 mmol) and K₂CO₃ (2.76 g, 20 mmol) in 40 mL of DMF was stirred at 25° C. for 16 h. Then the mixture was poured into 300 mL of water, extracted with ethyl acetate (200 mL), washed with water (200 mL) and brine (100 mL), and dried over anhydrous sodium sulfate. The solvent was evaporated at 40° C. under reduced pressure and the residue was purified by silica gel chromatography eluting with ethyl acetate and petroleum ether (1:5) to afford the product (3.1 g, 95%) as a colorless oil. $^1$H NMR (300 MHz, DMSO-d₆): δ 7.55 (dd, 1H), 7.36-7.15 (m, 7H), 4.60 (s, 2H), 4.22-4.19 (m, 2H), 3.80-3.77 (m, 2H).

(b) 3-(2-(benzyloxy)ethoxy)-2-bromo-6-fluorobenzaldehyde

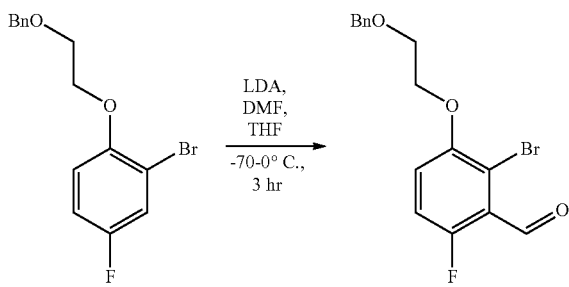 [SMILES: Fc1ccc(OCCOCc2ccccc2)c(Br)c1 ; O=Cc1c(F)ccc(OCCOCc2ccccc2)c1Br]

A solution of 1-(2-(benzyloxy)ethoxy)-2-bromo-4-fluorobenzene (1.6 g, 4.9 mmol) in 30 mL of THF was cooled to −70° C., and LDA (2.0 M in THF, 3.5 mL, 7 mmol) was added dropwise. The resulting mixture was kept stirring for 2 h at low temperature before a solution of DMF (1.1 g, 15 mmol) in THF (3 mL) was added. The mixture was stirred for 1 h and then allowed to warm to 0° C. It was quenched by saturated aq. NH₄Cl and the mixture was extracted with ethyl acetate (100 mL). The organic layer was washed with water (50 mL) and brine (50 mL), and dried over anhydrous sodium sulfate. The solvent was removed under reduced pressure and the residue was purified by silica gel chromatography eluting with ethyl acetate and petroleum ether (1:3) to afford the product (1.2 g, 69%) as a colorless oil. $^1$H NMR (300 MHz, DMSO-d₆): δ 10.22 (s, 1H), 7.48-7.27 (m, 7H), 4.60 (s, 2H), 4.29-4.26 (m, 2H), 3.82-3.79 (m, 2H).

(c) 6-(2-(benzyloxy)ethoxy)-3-fluoro-2-formylphenylboronic acid

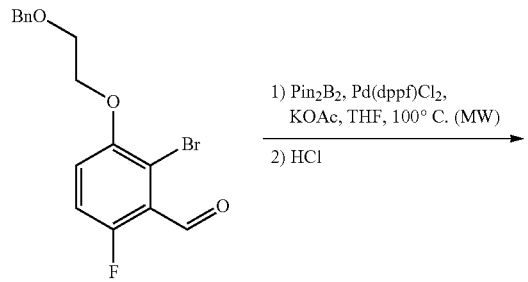

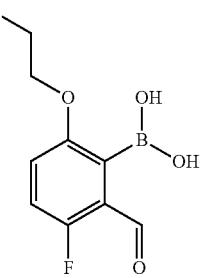

A solution of 3-(2-(benzyloxy)ethoxy)-2-bromo-6-fluorobenzaldehyde (1 g, 2.8 mmol), Pin₂B₂ (1 g, 4 mmol), KOAc (0.56 g, 6 mmol) and Pd(dppf)Cl₂ (0.05 g) in 30 mL of THF was degassed with N₂ for six times. Then the mixture was heated at 100° C. (microwave irradiated) for 4 h. The reaction mixture was cooled to room temperature, filtered, and concentrated under reduced pressure. The residue was purified by silica gel chromatography eluting with ethyl acetate and petroleum ether (1:5). The fractions were combined and concentrated under reduced pressure. The residue was dissolved in THF (20 mL) and 6N HCl (4 mL) and the resulting mixture was stirred at room temperature for 1 h. After it was extracted with ethyl acetate (20 ml×3), the combined organic layer was concentrated under reduced pressure to afford the crude product (0.5 g, 56%). It was used directly in the next step without further purification. LC-MS: 336.0 [M+H₂O]⁺.

(d) 7-(2-(benzyloxy)ethoxy)-4-fluoro-3-(nitromethyl)benzo[c][1,2]oxaborol-1(3H)-ol

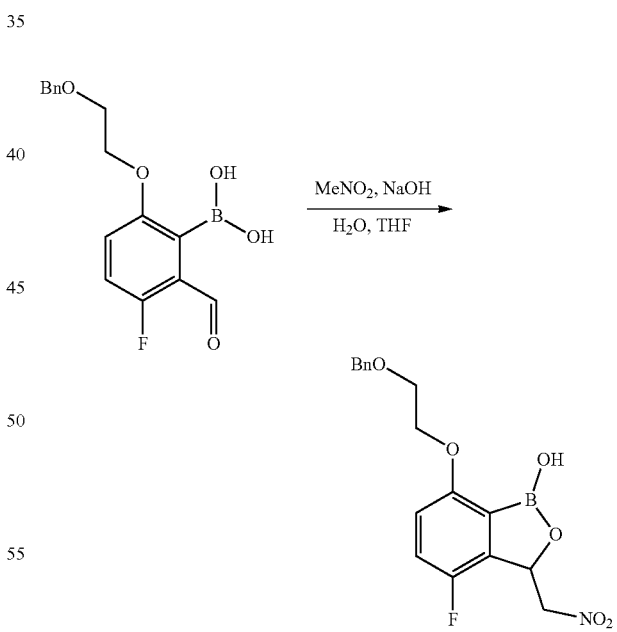

To a stirred solution of 6-(2-(benzyloxy)ethoxy)-3-fluoro-2-formylphenylboronic acid (0.5 g, 1.6 mmol) and CH₃NO₂ (0.2 g, 3.5 mmol) in 10 mL of THF was added a solution of NaOH (0.028 g, 0.7 mmol) in 3 mL of water at room temperature. Then the mixture was stirred at room temperature for 16 h and acidified with conc. HCl to pH=1 at 0° C. The mixture was extracted with ethyl acetate (20 mL) and the organic layer was washed with water (10 mL) and brine (10 mL) then dried over anhydrous sodium sulphate. After the solvent was removed under reduced pressure, the residue was purified by silica gel chromatography eluting with ethyl acetate and petroleum ether (1:10) to afford the crude product (0.5 g, 88%) as a colourless oil. LC-MS: 379.0 [M+H₂O]⁺.

(e) Title Compound

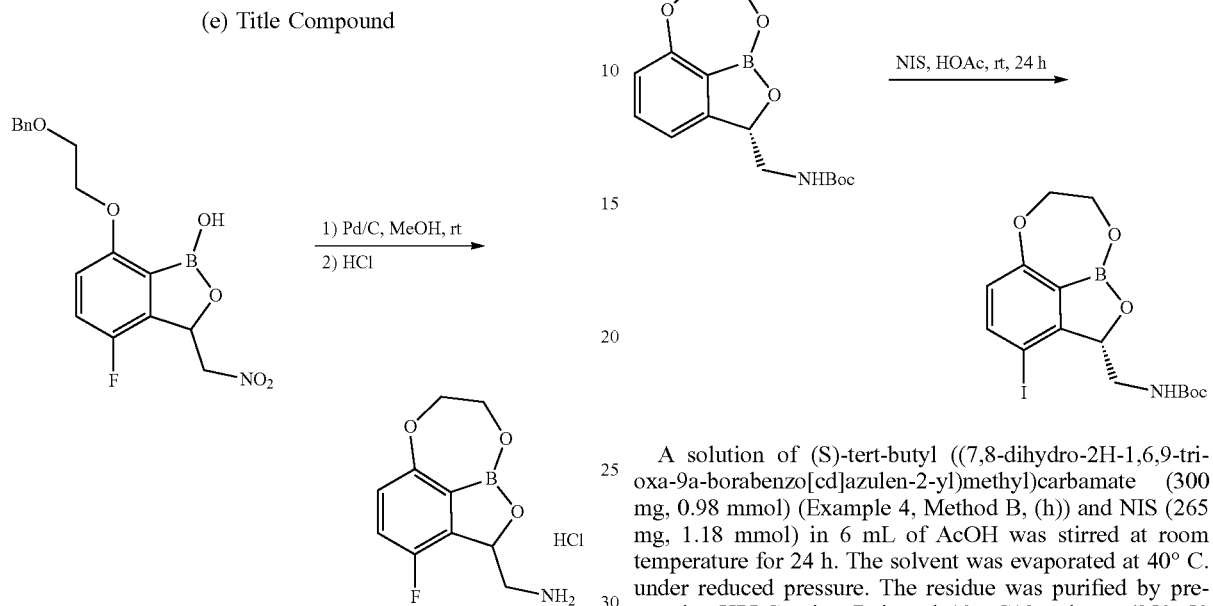

A solution of 7-(2-(benzyloxy)ethoxy)-4-fluoro-3-(nitromethyl)benzo[c][1,2]oxaborol-1(3H)-ol (0.5 g, 1.4 mmol) and Pd/C (10%, 0.1 g) in 20 mL of methanol was hydrogenated under 1 atm of H₂ at room temperature for 48 h. Then it was filtered through a bed of Celite and the filtrate was concentrated under reduced pressure to give an oil. The crude product was purified by preparative-HPLC using Daisogel 10μ C18 column (250×50 mm) and eluted with a gradient of water/acetonitrile (0.05% TFA). The collected fraction was concentrated under reduced pressure. The residue was dissolved in ether (5 mL) and 2N HCl (0.2 mL) was added. The resulting mixture was stirred at room temperature for 1 h. The solid was collected by filtration and washed with ether (10 mL) to give the title compound (0.035 g, 10%) as a white solid. LC-MS: 223.9 [M+H]⁺. ¹H NMR (400 MHz, DMSO-d₆): δ 8.22 (brs, 3H), 7.33 (t, 1H), 6.97 (dd, 1H), 5.68 (d, 1H), 4.69 (brs, 1H), 4.37-4.23 (m, 3H), 3.43-3.40 (m, 1H), 3.03 (t, 1H).

Example 6 (S)-(3-iodo-7,8-dihydro-2H-1,6,9-trioxa-9a-borabenzo[cd]azulen-2-yl)methanamine hydrochloride (G6-I)

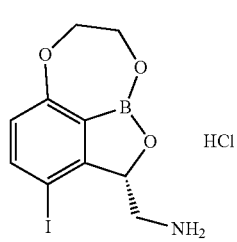 [SMILES: NC[C@H]1OB2OCCOc3ccc(I)c1c32 ; Cl]

(a) (S)-tert-butyl ((3-iodo-7,8-dihydro-2H-1,6,9-trioxa-9a-borabenzo[cd]azulen-2-yl)methyl)carbamate

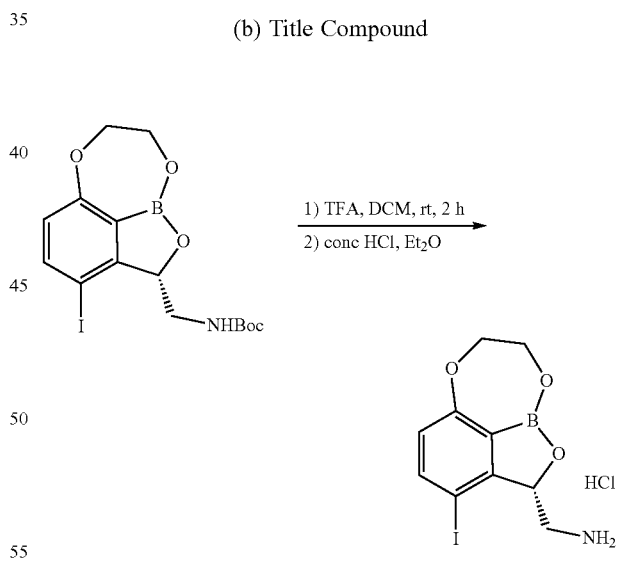

A solution of (S)-tert-butyl ((7,8-dihydro-2H-1,6,9-trioxa-9a-borabenzo[cd]azulen-2-yl)methyl)carbamate (300 mg, 0.98 mmol) (Example 4, Method B, (h)) and NIS (265 mg, 1.18 mmol) in 6 mL of AcOH was stirred at room temperature for 24 h. The solvent was evaporated at 40° C. under reduced pressure. The residue was purified by preparative-HPLC using Daisogel 10μ C18 column (250×50 mm) and eluted with a gradient of water/acetonitrile (0.05% TFA) to afford the product (200 mg, 47%) as light yellow oil. LC-MS: 432 [M+H]⁺.

(b) Title Compound

A solution of (S)-tert-butyl ((3-iodo-7,8-dihydro-2H-1,6,9-trioxa-9a-borabenzo[cd]azulen-2-yl)methyl)carbamate (140 mg, 0.32 mmol) and TFA (0.5 ml) in 5 mL of DCM was stirred at room temperature for 2 h. The solvent was evaporated at 40° C. under reduced pressure. The residue was dissolved in ether (5 mL) and 2N HCl in water (0.2 mL) was added. The resulting mixture was stirred at room temperature for 15 min. The solid was collected by filtration and washed with ether (10 mL) to give the title compound (90 mg, 75%) as a white solid. LC-MS: 332.0 [M+H]⁺. ¹H NMR (400 MHz, DMSO-d₆): δ 8.47 (brs, 3H), 7.80 (d, 1H), 6.78

(d, 1H), 5.37 (m, 1H), 4.72-4.53 (m, 1H), 4.4⁹⁻4.08 (m, 3H), 3.78-3.5₁ (m, 1H), 3.06-2.78 (m, 1H).

Example 7 (3-chloro-8-methyl-7,8-dihydro-2H-1,6,9-trioxa-9a-borabenzo[cd]azulen-2-yl)methanamine hydrochloride (G7-Cl)

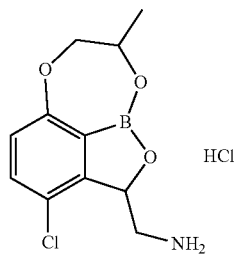 [SMILES: CC1COc2ccc(Cl)c3c2B(O1)OC3CN ; Cl]

(a) 2-bromo-3-(2-hydroxypropoxy)benzaldehyde

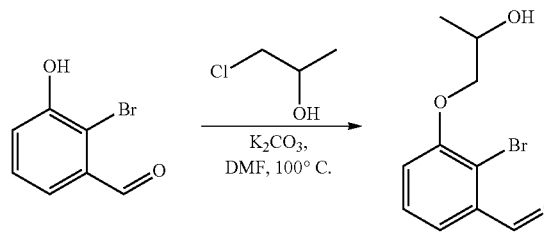

A solution of 2-bromo-3-hydroxybenzaldehyde (6.0 g, 29.85 mmol), 1-chloropropan-2-ol (8.46 g, 89.55 mmol) and K₂CO₃ (8.24, 59.7 mmol) in DMF (100 mL) was stirred at 100° C. overnight. Then the reaction mixture was quenched by adding water (4 L) and then extracted with EtOAc (3×1.5 L). The combined organic layers were washed with brine (250 mL), dried over anhydrous Na₂SO₄ and concentrated to dryness in vacuo. The residue was purified by column chromatography on silica gel (petroleum ether: ethyl acetate=5:1 to 2:1) to give the target crude compound (8.77 g). MS (ESI) m/z=259/261 [M+H]⁺.

(b) 3-(2-hydroxypropoxy)-2-(4,4,5,5-tetramethyl-1,3,2-dioxaborolan-2-yl)benzaldehyde

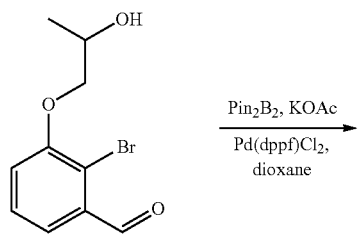

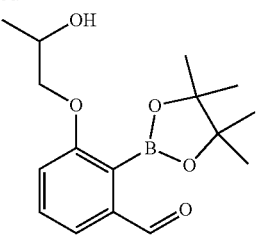

A solution of 2-bromo-3-(2-hydroxypropoxy)benzaldehyde (8.77 g, 34 mmol) 4,4,4',4',5,5,5',5'-octamethyl-2,2'-bi (1,3,2-dioxaborolane) (17.27 g, 68 mmol), Pd(dppf)Cl₂ (2.49 g, 3.4 mmol) and KOAc (9.99 g, 102 mmol) in dioxane (200 mL) was stirred at 100° C. overnight. Then the reaction mixture was quenched by adding water (200 mL) and then extracted with EtOAc (3×200 mL). The combined organic layers were washed with brine (250 mL), dried over anhydrous Na₂SO₄ and concentrated to dryness in vacuo. The residue was purified by column chromatography on silica gel (petroleum ether: ethyl acetate=5:1 to 1:1) to give the target crude compound (6 g). MS (ESI) m/z=307 [M+H]⁺.

(c) 8-methyl-2-(nitromethyl)-7,8-dihydro-2H-1,6,9-trioxa-9a-borabenzo[cd]azulene

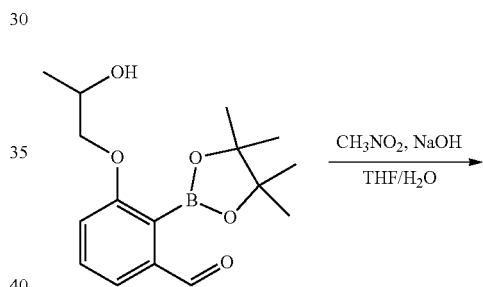

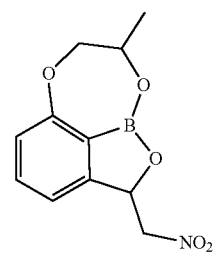

To a solution of NaOH (261.4 mg, 6.54 mmol) in water (8 mL) was added nitromethane (1.2 g, 19.6 mmol) at 5-10° C. After stirring for 15 min at 5-10° C., CTAB (0.19 g, 0.52 mmol) was added to the reaction mixture and followed by the addition of 3-(2-hydroxypropoxy)-2-(4,4,5,5-tetramethyl-1,3,2-dioxaborolan-2-yl)benzaldehyde (2.0 g, 6.54 mmol) at 5-10° C. The reaction mixture was stirred at rt for 5 h. The reaction mixture was acidified to pH=1 using diluted hydrochloric acid and stirred at rt overnight. The reaction mixture was filtered to give the target compound (541 mg, 33%).

(d) (8-methyl-7,8-dihydro-2H-1,6,9-trioxa-9a-borabenzo[cd]azulen-2-yl)methanamine acetate

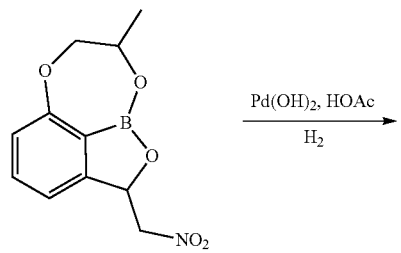

A solution of 8-methyl-2-(nitromethyl)-7,8-dihydro-2H-1,6,9-trioxa-9a-borabenzo[cd]azulene (541 mg, 2.173 mmol) and palladium hydroxide (300 mg) in acetic acid (10 mL) was shaken under an atmosphere of H2 overnight at room temperature. The mixture was filtered through a bed of Celite and the filtrate was concentrated in vacuo to give the crude compound (350 mg). MS (ESI) m/z=220 [M+H]⁺.

(e) tert-butyl ((8-methyl-7,8-dihydro-2H-1,6,9-trioxa-9a-borabenzo[cd]azulen-2-yl)methyl)carbamate

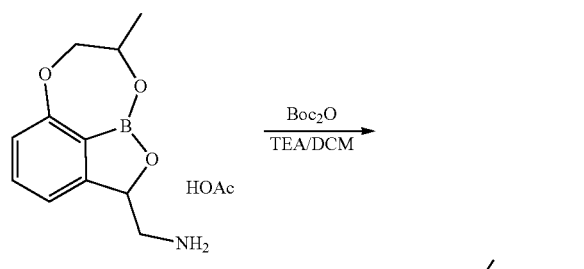

To the mixture of crude compound (8-methyl-7,8-dihydro-2H-1,6,9-trioxa-9a-borabenzo[cd]azulen-2-yl)methanamine acetate (3.0 g, 10.75 mmol) and triethylamine (6.5 g, 64.5 mmol) in dichloromethane (100 mL) at 0° C. was added di-tert-butyl dicarbonate (3.5 g, 16.13 mmol) and the mixture was stirred for 2 h at room temperature. The reaction was quenched with sat. NaHCO₃ (15 mL) and the resulting mixture was extracted with EtOAc (3×80 mL), the combined organic layers were dried over anhydrous Na₂SO₄ and concentrated in vacuo. The residue was purified by preparative-HPLC using a Daisogel 10μ C18 column (250×50 mm), eluted with gradient water/acetonitrile (0.05% TFA) to give the product (700 mg). MS (ESI) m/z=264 [M−56]⁺. ¹H NMR (300 MHz, DMSO-d₆): δ 7.44-7.39 (m, 1H), 7.01-6.98 (m, 2H), 6.88-6.85 (m, 1H), 5.24 (m, 1H), 4.52-4.44 (m, 2H), 4.18-4.00 (m, 1H), 3.39-3.36 (m, 1H), 3.15-3.06 (m, 1H), 1.42-1.09 (m, 15H).

(f) tert-butyl ((3-chloro-8-methyl-7,8-dihydro-2H-1,6,9-trioxa-9a-borabenzo[cd]azulen-2-yl)methyl)carbamate

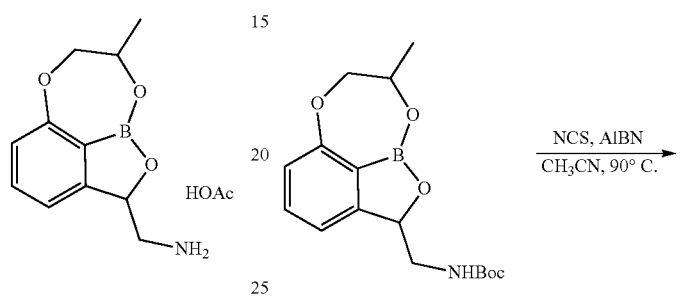

To a solution of tert-butyl ((8-methyl-7,8-dihydro-2H-1,6,9-trioxa-9a-borabenzo[cd]azulen-2-yl)methyl)carbamate (300 mg, 0.94 mmol) and 1-chloropyrrolidine-2,5-dione (151.4 mg, 1.13 mmol) in CH₃CN (20 mL) was added 2,2'-Azobis(2-methylpropionitrile) (15.4 mg, 0.094 mmol) and the mixture was stirred for 2 h at 90° C. The reaction mixture was then concentrated under high vacuum and the residue was purified by preparative-HPLC using a Gemini® 5μ C18 column (150×21.2 mm) and eluted with gradient water/acetonitrile (0.05% TFA) to give the desired product (150 mg, 45%). MS (ESI) m/z=298 [M−56]⁺.

(g) Title Compound

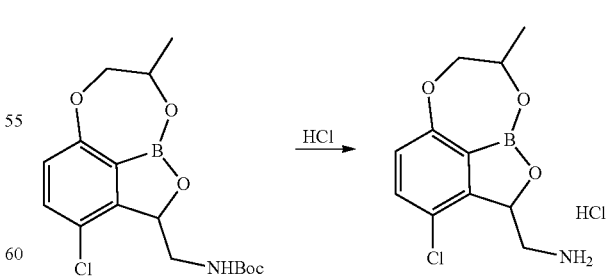

tert-butyl ((3-chloro-8-methyl-7,8-dihydro-2H-1,6,9-trioxa-9a-borabenzo[cd]azulen-2-yl)methyl)carbamate (150 mg, 0.425 mmol) in Et₂O/HCl and Et₂O (10 mL) was stirred at room temperature for 2 h and concentrated to dryness (water bath <30° C.). The residue was washed with acetonitrile (2×5 mL) and the white solid was dried in high vacuo to give the product (120 mg, 97%) as a white solid. $^1$H NMR (300 MHz, DMSO-$d_6$): δ 8.28 (s, 3H), 7.51-7.48 (d, 1H), 7.02-6.99 (d, 1H), 5.58-5.56 (d, 1H), 4.57 (m, 2H), 4.33-4.17 (m, 1H), 3.72-3.56 (m, 1H), 3.05-3.01 (m, 1H), 1.30-1.23 (m, 3H). MS (ESI) m/z=254 [M+H]$^+$.

Example 8 (3-bromo-8-methyl-7,8-dihydro-2H-1,6, 9-trioxa-9a-borabenzo[cd]azulen-2-yl)methanamine hydrochloride (G8-Br)

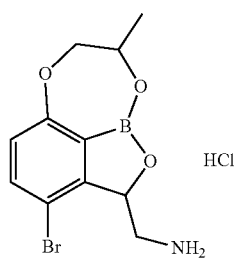 [SMILES: CC1COc2ccc(Br)c3c2B(O1)OC3CN ; Cl]

(a) tert-butyl ((3-bromo-8-methyl-7,8-dihydro-2H-1, 6,9-trioxa-9a-borabenzo[cd]azulen-2-yl)methyl)carbamate

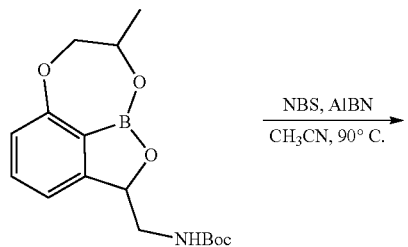

To a solution of tert-butyl ((8-methyl-7,8-dihydro-2H-1, 6,9-trioxa-9a-borabenzo[cd]azulen-2-yl)methyl)carbamate (180 mg, 0.564 mmol) (Example 5, (e)) and 1-bromopyrrolidine-2,5-dione (120 mg, 0.677 mmol) in CH$_3$CN (20 mL) was added 2,2'-Azobis(2-methylpropionitrile (9.2 mg, 0.056 mmol) and the mixture was stirred for 2 h at 90° C. The reaction mixture was then concentrated in high vacuo and the residue was purified by preparative-HPLC using a Gemini® 5 u C18 column (150×21.2 mm) eluted with gradient water/acetonitrile (0.05% TFA) to give the product (60 mg). MS (ESI) m/z=342/344 [M−56]$^+$.

(b) Title Compound

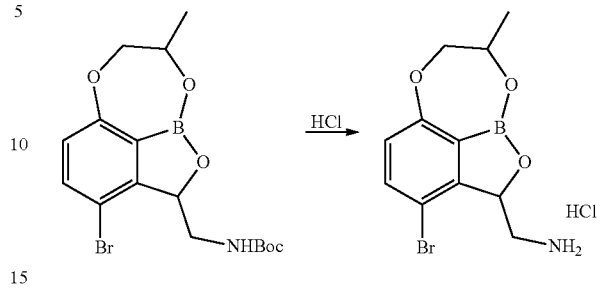

tert-butyl ((3-bromo-8-methyl-7,8-dihydro-2H-1,6,9-trioxa-9a-borabenzo[cd]azulen-2-yl)methyl)carbamate (60 mg, 0.15 mmol) in saturated HCl (gas) in Et$_2$O (10 mL) was stirred at rt for 2 h and concentrated to dryness (water bath temperature <30° C.). The residue purified by preparative-HPLC using a Gemini® 5 u C18 column (150×21.2 mm) eluted with gradient water/acetonitrile (0.05% TFA) to give the product (20 mg) as a white solid. $^1$H NMR (400 MHz, DMSO-$d_6$): δ 8.12 (br, 3H), 7.65 (m, 1H), 6.96 (m, 1H), 5.45 (m, 1H), 4.58 (m, 2H), 4.29-4.16 (m, 1H), 3.77-3.59 (m, 1H), 3.04 (m, 1H), 1.29-1.21 (d, 3H). MS (ESI) m/z=298/300 [M+H]$^+$.

Example 9 (3-bromo-8,8-dimethyl-7,8-dihydro-2H-1,6,9-trioxa-9a-borabenzo[cd]azulen-2-yl)methanamine hydrochloride (G9-Br)

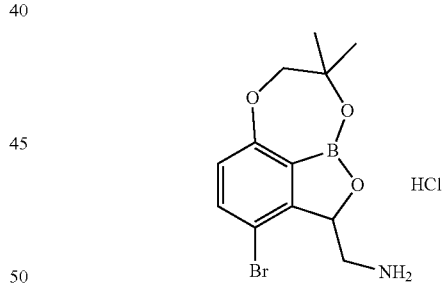

(a) 2-bromo-3-(2-hydroxy-2-methyl propoxy)benzaldehyde

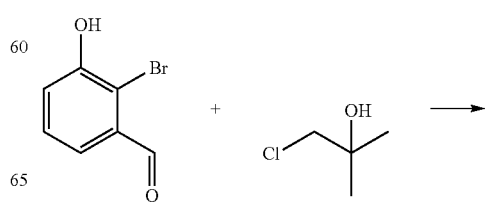

-continued

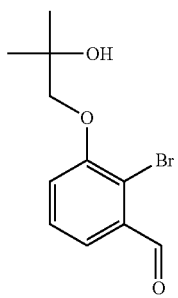

A solution of 2-bromo-3-hydroxybenzaldehyde (7.5 g, 37.3 mmol), 1-chloro-2-methylpropan-2-ol (9.4 g, 85.6 mmol) and Na$_2$CO$_3$ (6.7 g, 63.2 mmol) in 70 mL of DMSO was stirred at 140° C. for 3 hours. Then the mixture was cooled to room temperature, poured into 300 mL of water, extracted with ethyl acetate (600 mL), washed with water (300 mL), brine (50 mL), dried over anhydrous sodium sulfate. The solvent was evaporated at 40° C. under reduced pressure and the residue was purified by silica gel chromatography, eluting with a mixture of ethyl acetate and petroleum ether (1:3) to give the title compound (9.2 g, 90.3%) as a colorless oil. $^1$H NMR (300 MHz, CDCl$_3$): δ 10.43 (s, 1H), 7.54 (dd, 1H, J1=3.0, J2=7.5), 7.40-7.34 (m, 1H), 7.54 (dd, 1H, J1=3, J2=7.5), 3.90 (s, 2H), 1.42 (s, 6H).

(b) 3-(2-hydroxy-2-methylpropoxy)-2-(4,4,5,5-tetramethyl-1,3,2-dioxaborolan-2-yl)benzaldehyde

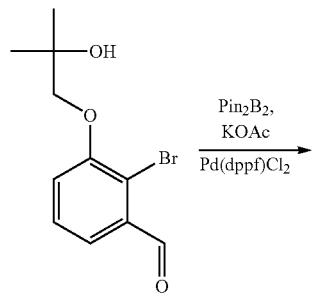

A solution of 2-bromo-3-(2-hydroxy-2-methylpropoxy) benzaldehyde (9.2 g, 33.7 mmol), Pin$_2$B$_2$ (17.1 g, 67.4 mmol), KOAc (9.9 g, 101.1 mmol) and Pd(dppf)Cl$_2$ (2.5 g) in 240 mL of 1,4-dioxane was degassed with N$_2$ for six times. Then the reaction was stirred at 99° C. under nitrogen for 16 hours. The reaction was cooled, filtered, then evaporated at 40° C. under reduced pressure and the residue was purified by silica gel chromatography, eluting with a mixture of ethyl acetate and petroleum ether (1:5) to give the title compound (10 g, crude) including de-Br by-product (used directly in the next step without further purification).

(c) 8,8-dimethyl-2-(nitromethyl)-7,8-dihydro-2H-1,6,9-trioxa-9a-borabenzo[cd]azulene

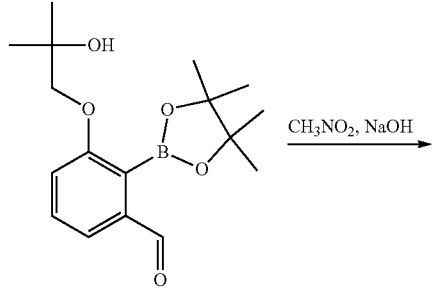

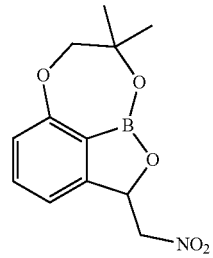

To a stirred solution of 3-(2-hydroxy-2-methylpropoxy)-2-(4,4,5,5-tetramethyl-1,3,2-dioxaborolan-2-yl)benzaldehyde (10 g, 31.3 mmol) and CH$_3$NO$_2$ (5.7 g, 93.8 mmol) in 100 mL of THF was added a solution of NaOH (1.25 g, 31.3 mmol) in 60 mL of water at room temperature. Then the reaction was stirred at room temperature for 16 hours. Then the reaction was acidified by conc. HCl to pH=1 at 0° C. and stirred at room temperature for 1 hour. The mixture was extracted with ethyl acetate (100 mL), washed with water (30 mL), then brine (30 mL), dried over anhydrous sodium sulphate. The solvent was evaporated at 40° C. under reduced pressure and the residue was purified by silica gel chromatography eluting with a mixture of ethyl acetate and petroleum ether (1:10) to give the title compound (3 g, 36.5%) as a colourless oil.

(d) (8,8-dimethyl-7,8-dihydro-2H-1,6,9-trioxa-9a-borabenzo[cd]azulen-2-yl)methanamine acetate

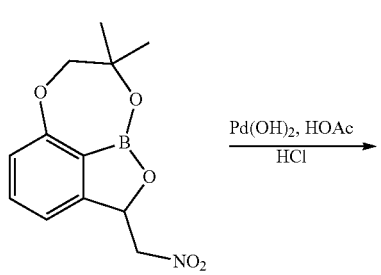

69

-continued

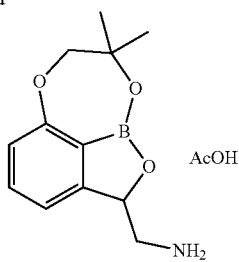

A solution of 8,8-dimethyl-2-(nitromethyl)-7,8-dihydro-2H-1,6,9-trioxa-9a-borabenzo[cd]azulene (1 g, 3.8 mmol) and Pd(OH)$_2$ (10%, 0.2 g) in 20 mL of acetic acid was hydrogenated at 1 atm of H2 at rt for 16 hours. Then the mixture was filtered and the solvent was evaporated at 40° C. under reduced pressure to give the title compound (0.9 g, crude) as an oil (acetate salt). LC-MS: 234.1 [M+H]$^+$.

(e) tert-butyl ((8,8-dimethyl-7,8-dihydro-2H-1,6,9-trioxa-9a-borabenzo[cd]azulen-2-yl)methyl)carbamate

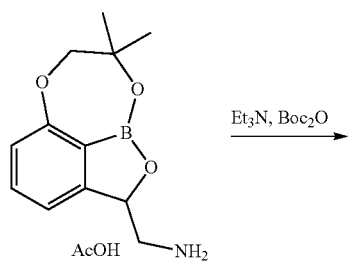

To a stirred solution of (8,8-dimethyl-7,8-dihyd,o-2H-1,6,9-trioxa-9a-borabenzo[cd]azulen-2-yl)methanamine acetate (0.7 g, 2.39 mmol) in 70 mL of CH$_2$Cl$_2$ cooled to 0° C. was added Et$_3$N (0.61 g, 6.0 mmol). Then Boc$_2$O (0.98 g, 4.5 mmol) was added in one portion, and the reaction was stirred at room temperature for 16 hours. The mixture was washed with 0.3 N HCl (30 mL), water (30 mL) and dried over anhydrous sodium sulphate. The solvent was evaporated at 40° C. at reduced pressure and the residue was purified by silica gel chromatography eluting with a mixture of ethyl acetate and petroleum ether (1:4) to give the title compound (0.63 g, 79%) as an oil. LC-MS: 234.1 [M+H−100]$^+$.

70

(f) tert-butyl ((3-bromo-8,8-dimethyl-7,8-dihydro-2H-1,6,9-trioxa-9a-borabenzo[cd]azulen-2-yl)methyl)carbamate

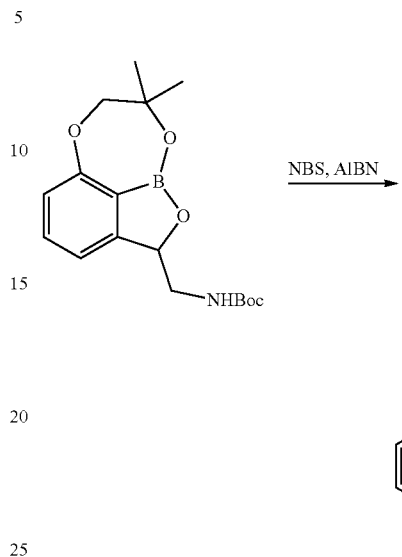

A solution of tert-butyl ((8,8-dimethyl-7,8-dihydro-2H-1,6,9-trioxa-9a-borabenzo[cd]azulen-2-yl)methyl)carbamate (232 g, 0.70 mmol), NBS (143 mg, 0.80 mmol) and AlBN (20 mg) in 30 mL of acetonitrile was stirred at reflux for 1 hour. The solvent was evaporated at 40° C. at reduced pressure and the residue was purified by silica gel chromatography eluting with a mixture of ethyl acetate and petroleum ether (1:4) to give the title compound (260 mg, 88.6%) as a solid. LC-MS: 312.0/314.0 [M+H−100]$^+$.

(g) Title Compound

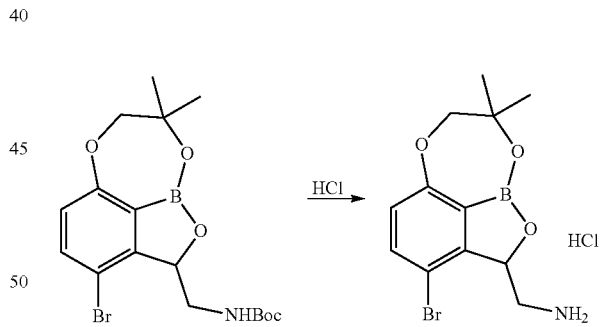

A solution of tert-butyl ((3-bromo-8,8-dimethyl-7,8-dihydro-2H-1,6,9-trioxa-9a-borabenzo[cd]azulen-2-yl)methyl)carbamate (260 mg, 0.63 mmol) in a saturated HCl solution in 1,4-dioxane (20 mL) was stirred at room temperature for 3 hours. The solvent was evaporated at 40° C. under reduced pressure and the residue was purified by preparative-HPLC using a Gemini® 5 u C18 column (150× 21.2 mm) eluted with gradient water/acetonitrile (0.05% TFA) treating with 0.1 mL of concentrated HCl to give the desired product (20 mg, 9.1%) as a white solid. LC-MS: 311.9 [M+H]$^+$. $^1$H NMR (400 MHz, CD$_3$OD): δ 7.63 (d, 1H, J=8), 6.95 (d, 1H, J=8), 5.52-5.45 (m, 1H), 4.41 (d, 1H, J=12), 4.17 (d, 1H, J=16), 4.09-3.85 (m, 1H), 3.13-2.98 (m, 1H), 1.37-1.30 (m, 6H).

Example 10 (S)-(3-bromo-8,8-dimethyl-7,8-di-hydro-2H-1,6,9-trioxa-9a-borabenzo[cd]azulen-2-yl)methanamine hydrochloride G10-Br)

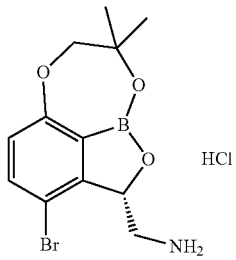 [SMILES: CC1(C)COc2ccc(Br)c3c2B(O[C@@H]3CN)O1 ; Cl]

(a) (S)-tert-butyl ((3-bromo-8,8-dimethyl-7,8-di-hydro-2H-1,6,9-trioxa-9a-borabenzo[cd]azulen-2-yl)methyl)carbamate

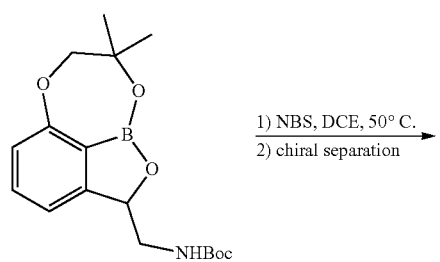

A solution of tert-butyl ((8,8-dimethyl-7,8-dihydro-2H-1,6,9-trioxa-9a-borabenzo[cd]azulen-2-yl)methyl)carbamate (5.5 g, 16.5 mmol) (Example 9, (e)) and NBS (3.2 g, 18.2 mmol) in 100 mL of dichloroethane was stirred at 50° C. for 18 hours. The solvent was evaporated at 40° C. under reduced pressure and the residue was purified by silica gel chromatography eluting with a mixture of ethyl acetate and petroleum ether (1:10) to give the title compound (5.9 g, 86.5%) as an oil. The racemic compound separated via SFC (chiral column CHIRALPAK AD-H, eluted with EtOH (20%) and $CO_2$ (80%)) to give 2.2 g of (S)-isomer (first eluting isomer, RT=3.0 min) and 2.2 g of (R)-isomer (second eluting isomer, RT=4.1 min). LC-MS: 312.0/314.0 [M+H-100]$^+$.

(b) Title Compound

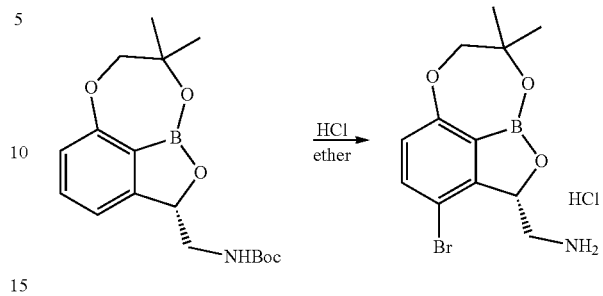

Dry HCl was bubbled through a solution of (S)-tert-butyl ((3-bromo-8,8-dimethyl-7,8-dihydro-2H-1,6,9-trioxa-9a-borabenzo[cd]azulen-2-yl)methyl)carbamate (2.2 g, 5.34 mmol) in diethyl ether (150 mL) at room temperature for 3 hours and then stirred for 18 hours. The solvent was filtered and the filter cake was dried in vacuo to give the (S)-isomer (1.4 g, 76%) as a white solid. LC-MS: 311.9 [M+H]$^+$. $^1$H NMR (400 MHz, DMSO-$d_6$): δ 8.23 (brs, 3H), 7.64 (d, 1H, J=8), 6.96 (d, 1H, J=8), 5.48-5.46 (m, 1H), 4.43-4.40 (m, 1H), 4.21-4.1-0 (m, 1H), 3.75-3.55 (m, 1H), 3.05-2.95 (m, 1H), 1.36-1.27 (ds, 6H). Similarly, the acid treatment of (R)-tert-butyl ((3-bromo-8,8-dimethyl-7,8-dihydro-2H-1,6,9-trioxa-9a-borabenzo[cd]azulen-2-yl)methyl)carbamate gave the corresponding (R)-isomer as a white solid (1.4 g, 76%). LC-MS: 312.0 [M+H]$^+$. $^1$H NMR (400 MHz, DMSO-$d_6$): δ 8.29 (brs, 3H), 7.65 (d, 1H, J=8), 6.96 (d, 1H, J=8), 5.48-5.46 (m, 1H), 4.42-4.39 (m, 1H), 4.22-4.10 (m, 1H), 3.75-3.50 (m, 1H), 3.03-2.93 (m, 1H), 1.36-1.27 (ds, 6H).

Example 11 (3-chloro-8,8-dimethyl-7,8-dihydro-2H-1,6,9-trioxa-9a-borabenzo[cd]azulen-2-yl)methanamine hydrochloride G11-Cl

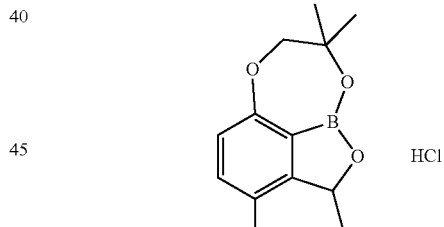

(a) tert-butyl ((3-chloro-8,8-dimethyl-7,8-dihydro-2H-1,6,9-trioxa-9a-borabenzo[cd]azulen-2-yl)methyl)carbamate

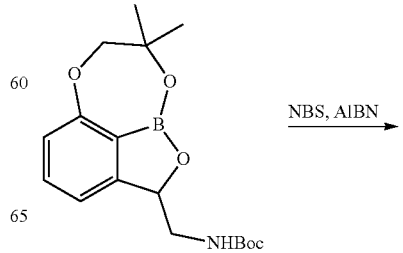

-continued

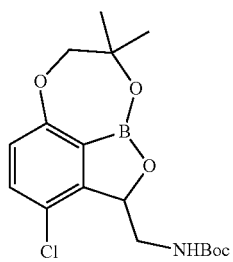

A solution of tert-butyl ((8,8-dimethyl-7,8-dihydro-2H-1,6,9-trioxa-9a-borabenzo[cd]azulen-2-yl)methyl)carbamate (519 mg, 1.56 mmol) (Example 9, (e)), NCS (250 mg, 1.87 mmol) and AIBN (30 mg) in 50 mL of acetonitrile was stirred at reflux for 1 hour. The solvent was evaporated at 40° C. under reduced pressure and the residue was purified by silica gel chromatography eluting with a mixture of ethyl acetate and petroleum ether (1:5) to afford the desired product (300 mg, 52.4%, containing 6-Cl isomer) as a solid. LC-MS: 268.1 [M+H−100]$^+$.

(b) Title Compound

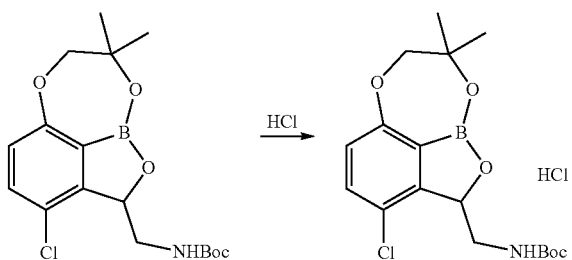 [SMILES: CC(C)(C)OC(=O)NCC1OB2OC(C)(C)COc3ccc(Cl)c1c32 ; Cl ; CC(C)(C)OC(=O)NCC1OB2OC(C)(C)COc3ccc(Cl)c1c32 ; Cl]

A solution of tert-butyl ((3-chloro-8,8-dimethyl-7,8-dihydro-2H-1,6,9-trioxa-9a-borabenzo[cd]azulen-2-yl)methyl)carbamate (300 mg, 0.82 mmol) in a saturated HCl solution in 1,4-dioxane (30 mL) was stirred at room temperature for 3 hours. The solvent was evaporated at 40° C. under reduced pressure and the residue was purified by preparative-HPLC using a Gemini® 5 u C18 column (150× 21.2 mm) eluted with gradient water/acetonitrile (0.05% TFA) followed by treating with 0.1 mL of conc. HCl to give the desired product (94 mg, 37.9%) as a white solid. LC-MS: 268.1 [M+H]$^+$. $^1$H NMR (400 MHz, DMSO-d$_6$): δ 8.40 (brs, 3H), 7.52 (d, 1H, J=8), 7.02 (d, 1H, J=8), 5.60-5.58 (m, 1H), 4.42-4.38 (m, 1H), 4.23-4.07 (m, 1H), 3.67-3.57 (m, 1H), 3.02-2.92 (m, 1H), 1.36-1.27 (m, 6H).

Example 12 (S)-(3-chloro-8,8-dimethyl-7,8-dihydro-2H-1,6,9-trioxa-9a-borabenzo[cd]azulen-2-yl)methanamine hydrochloride (G12-Cl)

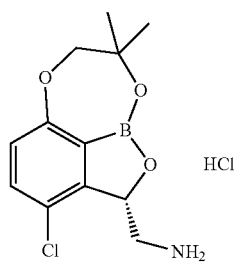 [SMILES: CC1(C)COc2ccc(Cl)c3c2B(O[C@@H]3CN)O1 ; Cl]

(a) (S)-tert-butyl ((3-chloro-8,8-dimethyl-7,8-dihydro-2H-1,6,9-trioxa-9a-borabenzo[cd]azulen-2-yl)methyl)carbamate

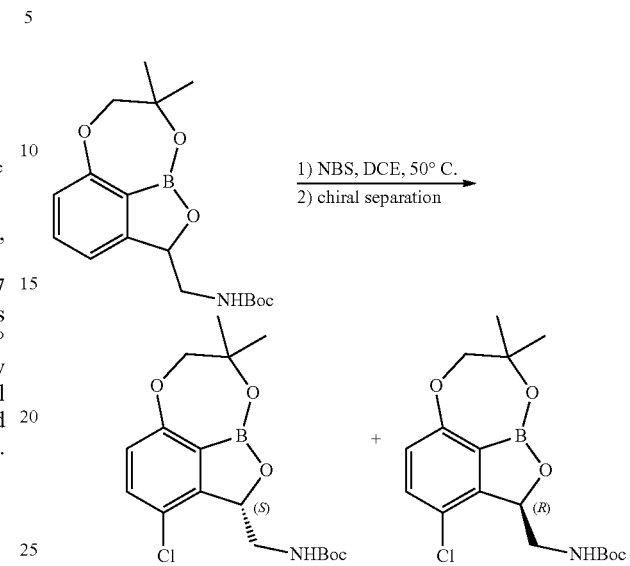

A solution of tert-butyl ((8,8-dimethyl-7,8-dihydro-2H-1,6,9-trioxa-9a-borabenzo[cd]azulen-2-yl)methyl)carbamate (4.1 g, 12.3 mmol) (Example 9, (e)) and NCS (1.73 g, 13 mmol) in 100 mL of dichloroethane was stirred at 50° C. for 5 hours. The solvent was evaporated at 40° C. under reduced pressure and the residue was purified by silica gel chromatography eluting with a mixture of ethyl acetate and petroleum ether (1:10) to give the title compound (2.6 g, 58%) as an oil. The racemic compound was separated via SFC (chiral column CHIRALPAK AD-H, eluted with EtOH (20%) and CO$_2$ (80%)) to give 1.2 g of (S)-isomer (first eluting isomer, RT=2.6 min) and 1.2 g of (R)-isomer (second eluting isomer, RT=3.5 min. LC-MS: 268.0 [M+H−100]$^+$.

(b) Title Compound

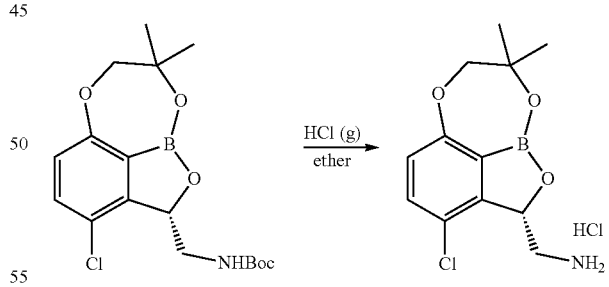

Dry HCl was bubbled through a solution of (S)-tert-butyl ((3-chloro-8,8-dimethyl-7,8-dihydro-2H-1,6,9-trioxa-9a-borabenzo[cd]azulen-2-yl)methyl)carbamate (1.2 g, 3.27 mmol) in diethyl ether (150 mL) at room temperature for 3 hours and then stirred for 18 hours. The solvent was filtered and the filter cake was dried in vacuo to give the (S)-isomer (0.8 g, 80%) as a white solid. LC-MS: 268 [M+H]$^+$. $^1$H NMR (400 MHz, DMSO-d$_6$): δ 8.34 (brs, 3H), 7.52 (d, 1H, J=8), 7.02 (d, 1H, J=8), 5.58-5.56 (m, 1H), 4.42-4.39 (m, 1H), 4.22-4.07 (m, 1H), 3.67-3.53 (m, 1H), 3.03-2.95 (m, 1H), 1.36-1.27 (ds, 6H).

Similarly, the acid treatment of (R)-tert-butyl ((3-chloro-8,8-dimethyl-7,8-dihydro-2H-1,6,9-trioxa-9a-borabenzo[cd]azulen-2-yl)methyl)carbamate gave the corresponding (R)-isomer (G25-Cl(R)) as a white solid (1.2 g, 80%). LC-MS: 268 [M+H]+. 1H NMR (400 MHz, DMSO-d6): δ 8.33 (bs, 3H), 7.52 (d, 1H, J=8), 7.02 (d, 1H, J=8), 5.58 (m, 1H), 4.42-4.39 (m, 1H), 4.21-4.07 (m, 1H), 3.67-3.54 (m, 1H), 3.03-2.95 (m, 1H), 1.36-1.27 (ds, 6H).

Example 13 ((2S,8R)-2-(aminomethyl)-3-fluoro-7,8-dihydro-2H-1,6,9-trioxa-9a-borabenzo[cd]azulen-8-yl)methanol hydrochloride (C15-F)

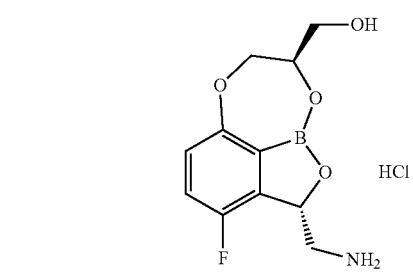 [SMILES: NC[C@H]1OB2O[C@H](CO)COc3ccc(F)c1c32 ; Cl]

(a) (S)-5-((2,2-dimethyl-1,3-dioxolan-4-yl)methoxy)-2-fluorobenzaldehyde

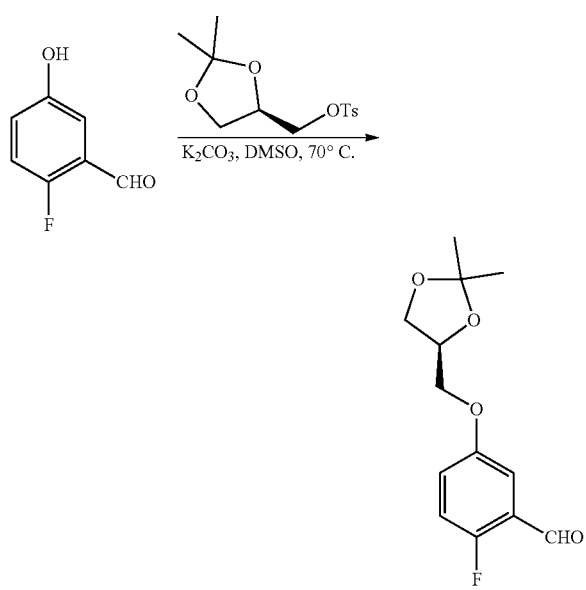

A solution of 2-fluoro-5-hydroxybenzaldehyde (1.9 g, 13.6 mmol), (R)-(2,2-dimethyl-1,3-dioxolan-4-yl)methyl 4-methylbenzenesulfonate (4.3 g, 15 mmol) and K2CO3 (2.37 g, 17.2 mmol) in 40 mL of DMSO was stirred at 70° C. for 16 h. Then the mixture was poured into 300 mL of water, extracted with ethyl acetate (200 mL), washed with water (200 mL) and brine (100 mL), and dried over anhydrous sodium sulfate. The solvent was evaporated at 40° C. under reduced pressure and the residue was purified by silica gel chromatography eluting with ethyl acetate and petroleum ether (1:5) to afford the product (2.9 g, 84%) as a colorless oil. LC-MS: 255.1 [M+H]+. 1H NMR (300 MHz, CD3OD): δ 10.30 (s, 1H), 7.31-7.28 (m, 1H), 7.16-7.05 (m, 2H), 4.49-4.45 (m, 1H), 4.18-3.85 (m, 4H), 1.45-1.40 (d, 6H).

(b) (S)-1-(5-(((S)-2,2-dimethyl-1,3-dioxolan-4-yl)methoxy)-2-fluorophenyl)-2-nitroethanol

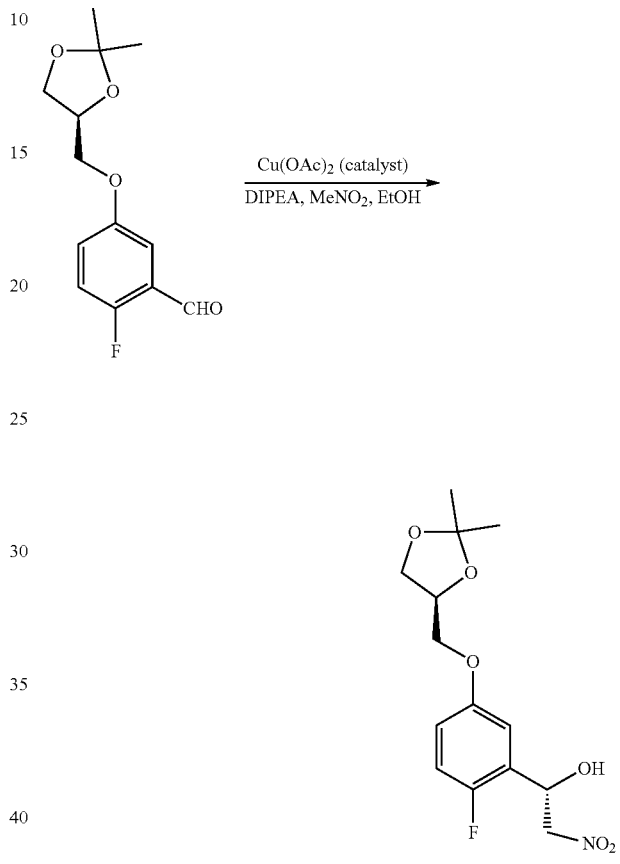

A mixture of copper (II) acetate (0.2 g, 1.1 mmol), (1R)-1,7,7-trimethyl-N-(pyridin-2-ylmethyl)bicyclo[2.2.1]heptan-2-amine (0.3 g, 1.23 mmol) (Example 4, Method B, (b)) in ethanol (30 mL) was stirred at r.t. for 1 h, then a solution of (S)-5-((2,2-dimethyl-1,3-dioxolan-4-yl)methoxy)-2-fluorobenzaldehyde (2.9 g, 11.4 mmol) in ethanol (50 mL) was added. The reaction mixture was cooled to −35° C. to −40° C., and then nitromethane (7 g, 115 mmol) was added dropwise, maintaining the temperature below −35° C., followed by the addition of diisopropylethylamine (0.32 g, 2.50 mmol). The reaction was stirred at −35° C. for 24 h, and then quenched with trifluoroacetic acid (0.29 g, 2.5 mmol). EtOAc (200 mL) was added to the resulting solution. The separated organic phase was washed with water (200 mL) and then concentrated under vacuum. The residue was purified by silica gel chromatography eluting with ethyl acetate and petroleum ether (1:10) to afford the product (3.3 g, 92%) as a colourless oil. LC-MS: 316.1 [M+H]+.

(c) (S)-2-amino-1-(5-(((S)-2,2-dimethyl-1,3-dioxo-lan-4-yl)methoxy)-2-fluorophenyl)ethanol

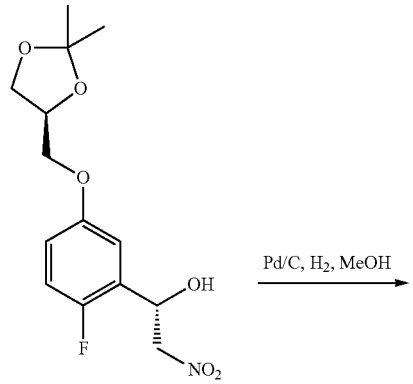

A solution of (S)-1-(5-(((S)-2,2-dimethyl-1,3-dioxolan-4-yl)methoxy)-2-fluorophenyl)-2-nitroethanol (3.2 g, 10.2 mmol) and Pd/C (10%, 0.5 g) in 70 mL of methanol was hydrogenated under 1 atm of H2 at room temperature for 48 h. Then it was filtered through a bed of Celite and the filtrate was concentrated under reduced pressure to afford the crude product (2.9 g, 100%) as a colourless oil. It was used directly in the next step without further purification. LC-MS: 286.2 [M+H]$^+$.

(d) (S)-2-(dibenzylamino)-1-(5-(((S)-2,2-dimethyl-1,3-dioxolan-4-yl)methoxy)-2-fluorophenyl)ethanol

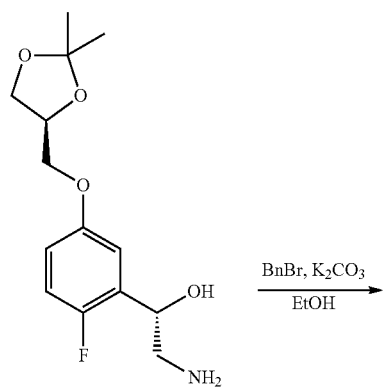

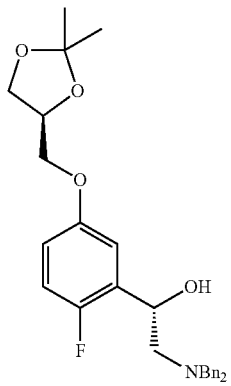

To a stirred solution of (S)-2-amino-1-(5-(((S)-2,2-dimethyl-1,3-dioxolan-4-yl)methoxy)-2-fluorophenyl)ethanol (2.9 g, 10.2 mmol) in 50 mL of EtOH were added K$_2$CO$_3$ (2.8 g, 20.3 mmol) and BnBr (3.6 g, 21 mmol). The reaction mixture was stirred overnight at room temperature. The solvent was removed under reduced pressure and the residue was purified by silica gel chromatography eluting with ethyl acetate and petroleum ether (1:10) to afford the product (3.8 g, 80%) as a colourless oil. LC-MS: 466.2 [M+H]$^+$ (e) (S)-3-((dibenzylamino)methyl)-7-WS)-2,2-dim-ethyl-1,3-dioxolan-4-yl)methoxy)-4-fluorobenzo[c][1,2]oxaborol-1(3H)-ol

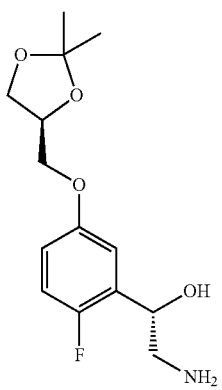

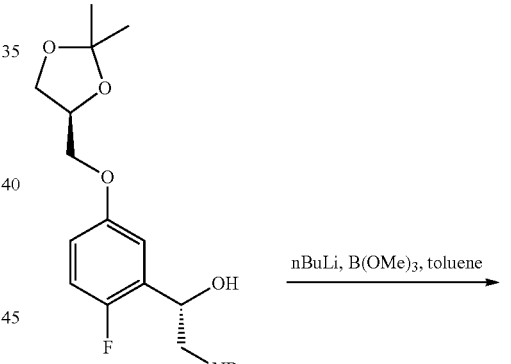

To a solution of (S)-2-(dibenzylamino)-1-(5-(((S)-2,2-dimethyl-1,3-dioxolan-4-yl)methoxy)-2-fluorophenyl)etha-nol (3.3 g, 7.1 mmol) in dry toluene (40 mL) at −30° C. under N$_2$ atmosphere was added n-BuLi (2.5 M in hexane, 20 mL, 50 mmol) dropwise over 30 minutes. After addition, the mixture was stirred at 0° C. for another 2 h, and then cooled to −70° C.; trimethyl borate (5.2 g, 50 mol) was added dropwise keeping the temperature below −50° C. After addition, the reaction mixture was allowed to warm to −40° C. for 3 h and then warmed to r.t. and stirred overnight. The reaction was quenched with 5% aqueous NaHCO₃ (20 mL) and stirred vigorously for 15 min, the resulting suspension was filtered and the filtrate was separated. The organic layer was washed with water (20 mL×3) and concentrated in vacuum to afford the crude product (3 g, 86%) as a yellow oil. LC-MS: 492.2 [M+1]

(f) Title Compound

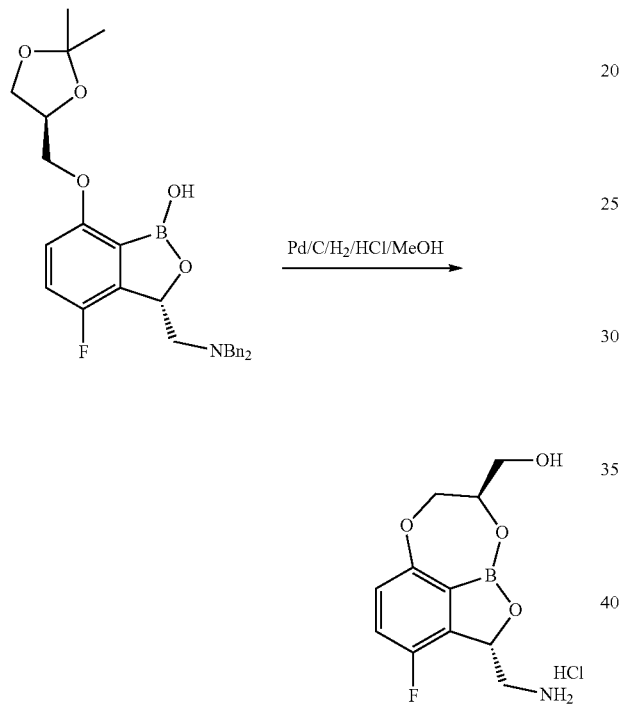

A solution of (S)-3-(((dibenzylamino)methyl)-7-(((S)-2,2-dimethyl-1,3-dioxolan-4-yl)methoxy)-4-fluorobenzo[c][1,2]oxaborol-1(3H)-ol (3 g, 6.1 mmol) and Pd/C (10%, 0.7 g) in 50 mL of methanol with 2 mL of conc HCl was hydrogenated under 1 atm of H2 at room temperature for 48 h. Then it was filtered through a bed of Celite and the filtrate was concentrated at reduced pressure to give an oil. The crude product was purified by preparative-HPLC using Daisogel 10µ C18 column (250×50 mm) and eluted with a gradient of water/acetonitrile (0.05% TFA). The collected fraction was concentrated under reduced pressure. The residue was dissolved in ether (30 mL) and sat. HCl (g) in ether (30 mL) and the mixture was stirred at room temperature for 1 h. The solid was collected by filtration and washed with ether to give the title compound (0.4 g, 23%) as a white solid. LC-MS: 254.2 [M+H]⁺. ¹H NMR (400 MHz, D2O): δ 7.20-7.16 (m, 1H), 6.94-6.91 (m, 1H), 5.55-5.53 (m, 1H), 4.17-4.04 (m, 3H), 3.70-3.62 (m, 3H), 3.19-3.14 (m, 1H).

Example 14 ((2S, 8R or 2R, 8S)-2-(aminomethyl)-3-chloro-8-methyl-7,8-dihydro-2H-1,6,9-trioxa-9a-borabenzo[cd]azulen-8-yl)methanol (C16-Cl)

Example 15 ((2S, 8S, or 2R, 8R)-2-(aminomethyl)-3-chloro-8-methyl-7,8-dihydro-2H-1,6,9-trioxa-9a-borabenzo[cd]azulen-8-yl)methanol (G17-Cl)

Example 14

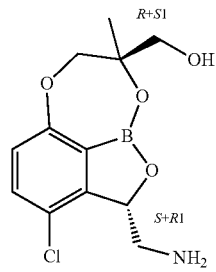

Example 15

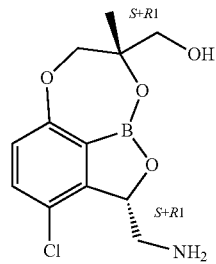

(a) ((2-methylallyloxy)methyl)benzene

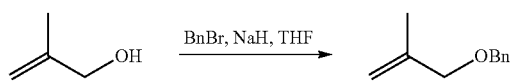

A solution of methallyl alcohol (80 g, 1.1 mol) in THF (100 mL) was added dropwise to a suspension of NaH (66 g, 1.65 mol) in THF (800 mL) at 25° C. under argon. After 1 h, a solution of benzyl bromide (207 g, 1.2 mol) in THF (100 mL) was added slowly and the reaction mixture was stirred at room temperature for 12 h. The reaction mixture was quenched with saturated NH₄Cl solution (200 mL) and extracted with ethyl acetate (3×200 mL). The combined organic layers were washed with water (100 mL) and brine (100 mL), dried over Na₂SO₄. The solvent was removed under reduced pressure. The residue was distilled to afford the desired product (134 g, 74%) as colorless oil. ¹H NMR (400 MHz, CDCl₃): δ 7.40-7.29 (m, 5H), 5.05 (s, 1H), 4.97 (s, 1H), 4.54 (s, 2H), 3.98 (s, 2H), 1.82 (s, 3H).

(2-(benzyloxymethyl)-2-methyloxirane

((2-methylallyloxy)methyl)benzene (41.5 g, 256 mmol) was dissolved in DCM (1200 mL) and cooled to 0° C. m-CPBA (69.7 g, 384 mmol) was added and the mixture was stirred overnight at room temperature for 12 h. After the white precipitate was filtered off, the filtrate was washed with saturated Na₂CO₃ solution (200 mL), H₂O (200 mL), and brine. After the solvent was removed under reduced pressure, the crude reside was purified by silica gel chromatography eluting with ethyl acetate and petroleum ether (1:20) to afford the pure product (20 g, 44%) as colorless oil. $^1$H NMR (400 MHz, CDCl₃): δ 7.40-7.29 (m, 5H), 4.60 (q, J=12.0 Hz, 2H), 3.61 (d, J=11.0 Hz, 1H), 3.48 (d, J=11.0 Hz, 1H), 2.78 (d, J=4.9 Hz, 1H), 2.66 (d, J=4.9 Hz, 1H), 1.43 (s, 3H).

3-(3-(benzyloxy)-2-hydroxy-2-methylpropoxy)-2-bromobenzaldehyde

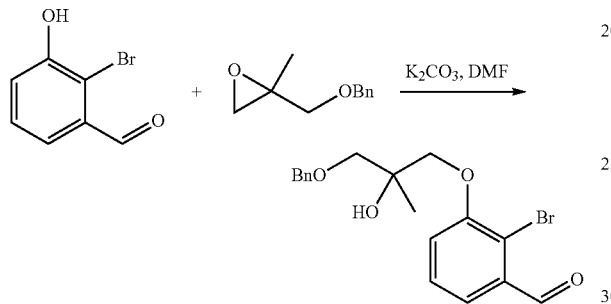

To a solution of (2-(benzyloxymethyl)-2-methyloxirane (26 g, 145.9 mmol) in DMF (700 mL) was added K₂CO₃ (42 g, 304.3 mmol), followed by 2-bromo-3-hydroxybenzaldehyde (30 g, 149.3 mmol). The suspension was stirred at 90° C. for 6 h. The mixture was cooled down to room temperature, diluted with brine and extracted with ethyl acetate (200 mL×3). The organic solvent was removed under vacuum and the residue was purified by silica gel chromatography eluting with ethyl acetate and petroleum ether (1:20) to afford the pure product (27 g, 49%) as light yellow oil. $^1$H NMR (400 MHz, DMSO-d₆): δ 10.29 (s, 1H), 7.512-7.41 (m, 3H), 7.31-7.23 (m, 5H), 4.91 (s, 1H), 4.53 (dd, J₁=12.4 Hz, J₂=17.2 Hz, 2H), 4.06 (d, J=9.2 Hz, 1H), 3.91 (d, J=9.2 Hz, 1H), 3.54 (d, J=9.3 Hz, 1H), 3.47 (d, J=9.3 Hz, 1H), 1.27 (s, 3H).

3-(3-(benzyloxy)-2-hydroxy-2-methylpropoxy)-2-(4,4,5,5-tetramethyl-1,3,2-dioxaborolan-2-yl)benzaldehyde

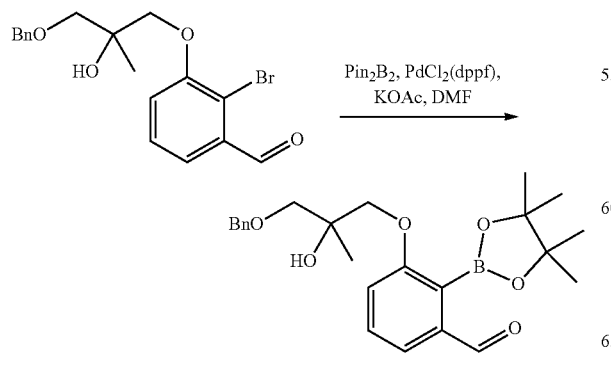

A solution of 3-(3-(benzyloxy)-2-hydroxy-2-methylpropoxy)-2-bromobenzaldehyde (21.3 g, 56.2 mmol), Pin₂B₂ (28.6 g, 112.4 mmol), KOAc (6.1 g, 61.9 mmol), PdCl₂(dppf) DCM (1.23 g, 1.7 mmol) in DMF (150 mL) was degassed for 3 times with nitrogen. The mixture was heated at 90° C. for 16 h. After the reaction was worked up with ethyl acetate and brine, the residue was purified by silica gel chromatography eluting with ethyl acetate and petroleum ether (1:20) to afford the desired product (15.3 g, 64%) as light yellow oil. LC-MS: 367.1 [344+Na]⁺

(3-(benzyloxy)-2-hydroxy-2-methylpropoxy)-3-(nitromethyl)benzo[c][1,2]oxaborol-1(3H)-ol

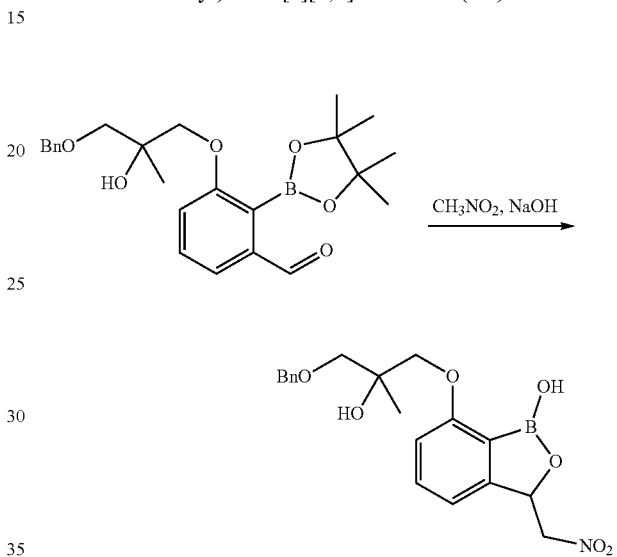

To an ice-cold solution of 3-(3-(benzyloxy)-2-hydroxy-2-methylpropoxy)-2-(4,4,5,5-tetramethyl-1,3,2-dioxaborolan-2-yl)benzaldehyde (18.8 g, 44.1 mmol) in THF was added a solution of NaOH (1.76 g, 44.1 mmol) in water (100 mL). After stirring for 15 min, CH₃NO₂ (3.3 g, 53 mmol) was added and the mixture was stirred at room temperature for 15 h. The reaction solution was acidified with AcOH to pH 3-5. The suspension was extracted with ethyl acetate (50 mL×3). The combined organic layer was evaporated under vacuum, and the residue was purified by silica gel chromatography eluting with ethyl acetate and petroleum ether (1:10) to afford the pure product (6.8 g, 40%) as colorless oil. LC-MS: 386.0 [M−1]⁻

(2-(aminomethyl)-8-methyl-7,8-dihydro-2H-1,6,9-trioxa-9a-borabenzo[cd]azulen-8-yl)methanol acetate

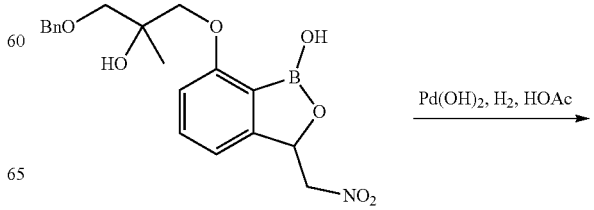

83

-continued

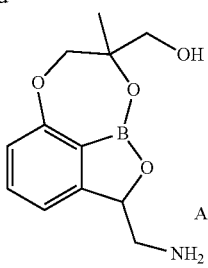

AcOH

Pd(OH)$_2$/C (200 mg) was added to a solution of 7-(3-(benzyloxy)-2-hydroxy-2-methylpropoxy)-3-(nitromethyl) benzo[c][1,2]oxaborol-1(3H)-ol (1 g, crude) in AcOH (20 mL). The solution was degassed 3 times with H2, and stirred at room temperature for 12 h. The reaction mixture was filtered through Celite, and the filtrate was concentrated under vacuum to afford the crude product (1 g, crude) as yellow solid.

tert-butyl ((8-(hydroxymethyl)-8-methyl-7,8-dihydro-2H-1,6,9-trioxa-9a-borabenzo[cd]azulen-2-yl)methyl)carbamate

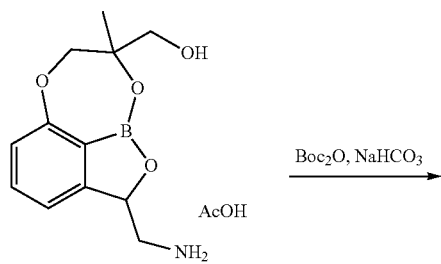

Boc$_2$O, NaHCO$_3$

NaHCO$_3$ (437 mg, 5.2 mmol) was added to a solution of (2-(aminomethyl)-8-methyl-7,8-dihydro-2H-1,6,9-trioxa-9a-borabenzo[cd]azulen-8-yl)methanol acetate (650 mg, 2.1 mmol) in t-BuOH (10 mL) and H$_2$O (10 mL) at room temperature. After stirring for 15 min, (Boc)$_2$O (854 mg, 3.9 mmol) was added and the reaction mixture was stirred at room temperature for 2 h. The mixture was acidified with AcOH to pH 6-7 and extracted with DCM (30 mL×3). Combined organic layers were evaporated under vacuum, and the residue was purified by silica gel chromatography eluting with ethyl acetate and petroleum ether (1:3) to afford the desired product (400 mg, 55%) as courses oil. LC-MS: 294.1 [M−55]$^+$

84 tert-butyl ((3-chloro-8-(hydroxymethyl)-8-methyl-7,8-dihydro-2H-1,6,9-trioxa-9a-borabenzo[cd]azulen-2-yl)methyl)carbamate

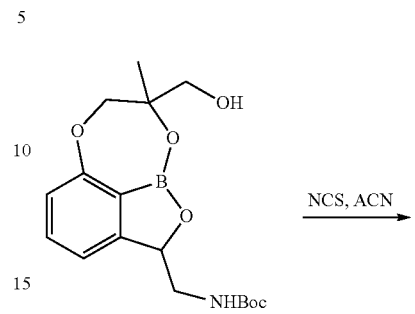

NCS, ACN

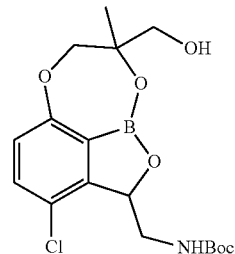

To a solution of tert-butyl ((8-(hydroxymethyl)-8-methyl-7,8-dihydro-2H-1,6,9-trioxa-9a-borabenzo[cd]azulen-2-yl)methyl)carbamate (200 mg, 0.57 mol) in ACN (10 mL) was added NCS (77 mg, 0.57 mmol), and the solution was stirred at 90° C. for 16 h. The reaction was quenched with NH$_4$Cl solution, extracted with ethyl acetate (20 mL×3). The organic layer was washed with brine, dried over Na$_2$SO$_4$, concentrated in vacuum. The crude residue was purified by silica gel chromatography eluting with ethyl acetate and petroleum ether (1:3) to afford the crude product (240 mg, crude) as yellow oil. LC-MS: 284.1 [283+H]$^+$ Title Compounds

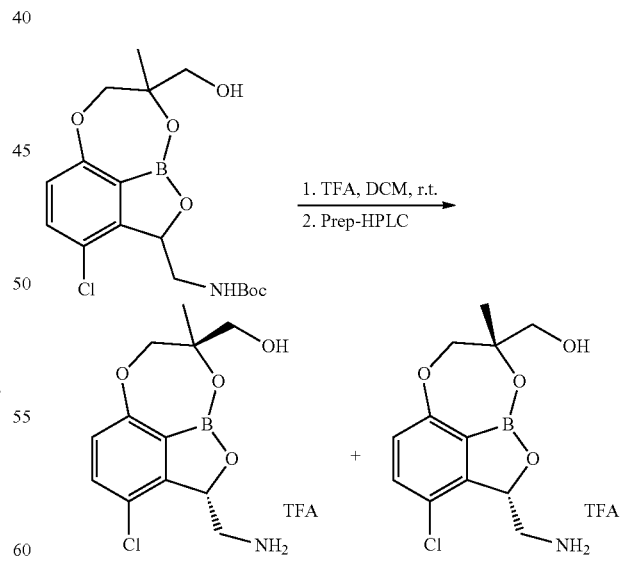

1. TFA, DCM, r.t.
2. Prep-HPLC

Example 14    Example 16 tert-butyl ((3-chloro-8-(hydroxymethyl)-8-methyl-7,8-dihydro-2H-1,6,9-trioxa-9a-borabenzo[cd]azulen-2-yl)methyl)carbamate (240 mg, crude) was dissolved in a solution of TFA (1 mL) in DCM (10 mL). The solution was stirred at room temperature for 1 h, and then was concentrated in vacuum. The crude product was purified by preparative-HPLC using Daisogel 10μ C18 column (250×50 mm) and eluted with a gradient of water/acetonitrile (0.05% TFA). The collected fraction was concentrated under reduced pressure to afford the title compounds. ((2S, 8R or 2R, 8S)-2-(aminomethyl)-3-chloro-8-methyl-7,8-dihydro-2H-1,6,9-trioxa-9a-borabenzo[cd]azulen-8-yl)methanol LC-MS: 284.0 [M+H]$^+$. $^1$H NMR (400 MHz, DMSO-d$_6$): δ 8.23 (s, 3H), 7.52 (d, J=8.6 Hz, 1H), 7.03 (d, J=8.5 Hz, 1H), 5.56 (dd, J=8.5, 2.1 Hz, 1H), 4.55 (s, 1H), 4.15 (s, 1H), 3.59 (s, 1H), 3.45 (s, 2H), 3.04 (s, 1H), 1.21 (s, 3H). ((2S, 8S, or 2R, 8R)-2-(aminomethyl)-3-chloro-8-methyl-7,8-dihydro-2H-1,6,9-trioxa-9a-borabenzo[cd]azulen-8-yl)methanol LC-MS: 284.1 [M+H]$^+$. $^1$H NMR (400 MHz, DMSO-d$_6$): δ 8.12 (s, 2H), 7.51 (s, 1H), 7.02 (s, 1H), 5.55 (s, 1H), 4.54 (s, 1H), 4.24-3.92 (m, 1H), 3.78-3.29 (m, 3H), 3.02 (s, 1H), 1.25 (s, 3H).

Example 16 ((2S, 8R, or 2R, 8S)-2-(aminomethyl)-3-bromo-8-methyl-7,8-dihydro-2H-1,6,9-trioxa-9a-borabenzo[cd]azulen-8-yl)methanol (C18-Br)

Example 17 ((2S, 8S, or 2R, 8R)-2-(aminomethyl)-3-bromo-8-methyl-7,8-dihydro-2H-1,6,9-trioxa-9a-borabenzo[cd]azulen-8-yl)methanol (G19-Br)

Example 16

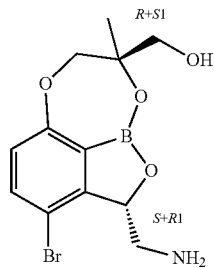

Example 17

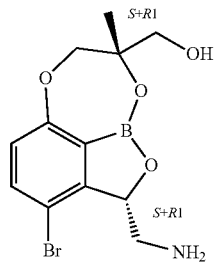

tert-butyl ((3-bromo-8-(hydroxymethyl)-8-methyl-7,8-dihydro-2H-1,6,9-trioxa-9a-borabenzo[cd]azulen-2-yl)methyl)carbamate

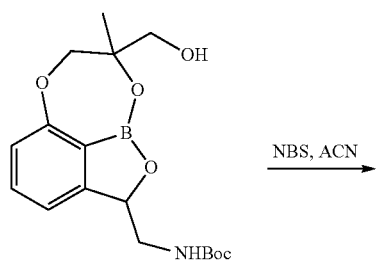

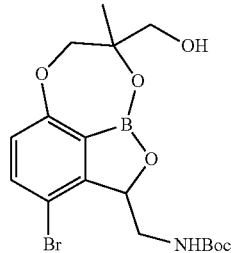

To a solution of tert-butyl ((8-(hydroxymethyl)-8-methyl-7,8-dihydro-2H-1,6,9-trioxa-9a-borabenzo[cd]azulen-2-yl)methyl)carbamate (200 mg, 0.57 mmol) in ACN (10 mL) was added NBS (102 mg, 0.57 mmol), and the solution was stirred at 90° C. for 1 h. The reaction was quenched with NH$_4$Cl solution, extracted with ethyl acetate (20 mL×3). The organic lay was washed with brine, dried over Na$_2$SO$_4$, concentrated in vacuum. The crude residue was purified by silica gel chromatography eluting with ethyl acetate and petroleum ether (1:3) to afford the product (230 mg, crude) as pale solid. LC-MS: 328.1 [M−Boc+H]$^+$.

Title Compounds

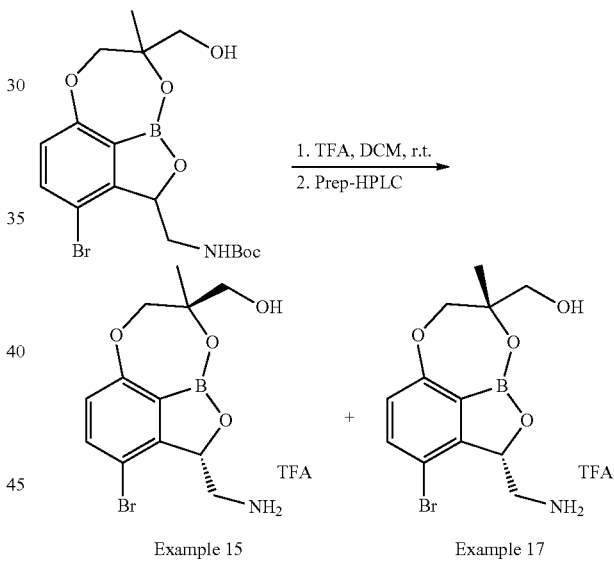

tert-butyl ((3-bromo-8-(hydroxymethyl)-8-methyl-7,8-dihydro-2H-1,6,9-trioxa-9a-borabenzo[cd]azulen-2-yl)methyl)carbamate (230 mg, crude) was dissolved in a solution of TFA (1 mL) in DCM (10 mL). The solution was stirred at room temperature for 1 h, and then was concentrated in vacuum. The crude product was purified by preparative-HPLC using Daisogel 10μ C18 column (250×50 mm) and eluted with a gradient of water/acetonitrile (0.05% TFA). The collected fraction was concentrated under reduced pressure to afford the title compounds. ((2S, 8R, or 2R, 8S)-2-(aminomethyl)-3-bromo-8-methyl-7,8-dihydro-2H-1,6,9-trioxa-9a-borabenzo[cd]azulen-8-yl)methanol LC-MS: 328.0 [M+H]$^+$. $^1$H NMR (400 MHz, DMSO-d$_6$) δ 8.10 (s, 3H), 7.65 (d, J=8.3 Hz, 1H), 7.07-6.88 (m, 1H), 5.56-5.39 (m, 1H), 5.36-5.17 (m, 1H), 4.61-4.52 (m, 1H), 4.19-4.07 (m, 1H), 3.62 (d, J=11.9 Hz, 1H), 3.51-3.39 (m, 2H), 3.04 (s, 1H), 1.18 (s, 3H). ((2S, 8S, or 2R, 8R)-2-(aminomethyl)-3-bromo-8-methyl-7,8-dihydro-2H-1,6,9- trioxa-9a-borabenzo[cd]azulen-8-yl)methanol LC-MS: 328.0 [M+H]$^+$. $^1$H NMR (400 MHz, DMSO-d$_6$): δ 8.13 (s, 2H), 7.65 (s, 1H), 6.98 (s, 1H), 5.47 (s, 1H), 5.26-5.06 (m, 1H), 4.53 (s, 1H), 4.19-3.97 (m, 1H), 3.83-3.56 (m, 1H), 3.51-3.26 (m, 2H), 3.01-2.93 (m, 1H), 1.25 (s, 3H).

In Vitro Assays

Example 18

MIC Determination Against Mycobacteria

The measurement of the Minimum Inhibitory Concentration (MIC) against *M. tuberculosis* strains for each tested compound was performed in 96-well flat-bottom, polystyrene microtiter plates in a final volume of 100 uL. Ten two-fold drug dilutions in neat DMSO starting at 50 mM were performed. Drug solutions were added to Middlebrook 7H9 medium (Difco) and isoniazid (INH) (Sigma Aldrich) was used as a positive control with 2-fold dilutions of INH starting at 160 ug/mL. The inoculum was standardized to approximately 1×10$^7$ cfu/ml and diluted 1 in 100 in Middlebrook 7H9 broth (Difco). This inoculum (100 uL) was added to the entire plate but G-12 and H-12 wells were used as blank controls. All plates were placed in a sealed box to prevent drying out of the peripheral wells and incubated at 37° C. without shaking for six days. A Resazurin solution was prepared by dissolving one tablet of Resazurin (Resazurin Tablets for Milk Testing; Ref 330884Y' VWR International Ltd) in 30 mL of sterile PBS (phosphate buffered saline). Of this solution, 25 uL were added to each well. Fluorescence was measured (Spectramax M5 Molecular Devices, Excitation 530 nm, Emission 590 nm) after 48 hours to determine the MIC value.

Example 19

MIC Against Clinical Strains

The BACTEC MGIT 960 System (Becton Dickinson) was used to carry out MIC determination in clinical isolates (Institute Carlos III) following the manufacturer instructions. The resistance pattern of clinical isolates is indicated by the following abbreviations H: Isoniazide, R: Rifampicin, T: Ethionamide, S: Streptomycin, E: Ethambutol, Z: Pyrazynamide, K: Kanamycin, A: Amikacin and CP: Capreomycin. Results for compound EXAMPLE 4 G4-Cl are shown in Tables 1A, 1B, 2A and 2B, and FIGS. 3 and 4. Results for EXAMPLE 2 G2-Br are shown in Tables 2C and 2D, and FIG. 4.

Table 1 Provides MIC Values for Example 4 G4-Cl Tested Against *M. tuberculosis* Sensitive (A) and Resistant (B) Clinical Isolates

A

| Strain | 362 | 457 | 3 | 356 | 357 | 370 | 137 | 169 | 192 | 199 | 206 | 207 | 208 | 223 |
|---|---|---|---|---|---|---|---|---|---|---|---|---|---|---|
| MIC (μM) | 0.04 | 0.04 | 0.04 | 0.04 | 0.04 | 0.04 | 0.08 | 0.08 | 0.08 | 0.08 | 0.08 | 0.08 | 0.08 | 0.08 |
| Strain | 231 | 237 | 247 | 248 | 249 | 250 | 253 | 255 | 256 | 257 | 261 | 265 | 269 | 281 |
| MIC (μM) | 0.08 | 0.08 | 0.08 | 0.08 | 0.08 | 0.08 | 0.08 | 0.08 | 0.08 | 0.08 | 0.08 | 0.08 | 0.08 | 0.08 |
| Strain | 292 | 296 | 311 | 314 | 316 | 317 | 322 | 323 | 324 | 326 | 327 | 328 | 329 | 332 |
| MIC (μM) | 0.08 | 0.08 | 0.08 | 0.08 | 0.08 | 0.08 | 0.08 | 0.08 | 0.08 | 0.08 | 0.08 | 0.08 | 0.08 | 0.08 |
| Strain | 333 | 337 | 358 | 361 | 371 | 385 | 391 | 424 | 440 | 442 | 460 | 481 | 716 | 729 |
| MIC (μM) | 0.08 | 0.08 | 0.08 | 0.08 | 0.08 | 0.08 | 0.08 | 0.08 | 0.08 | 0.08 | 0.08 | 0.08 | 0.08 | 0.08 |
| Strain | 730 | 731 | 733 | 734 | 736 | 737 | 52 | 267 | 374 | 274 | 325 | 705 | 161 | |
| MIC (μM) | 0.08 | 0.08 | 0.08 | 0.08 | 0.08 | 0.08 | 0.08 | 0.08 | 0.08 | 0.16 | 0.16 | 0.16 | 0.31 | |

B

| | Strain | | | | | | | | |
|---|---|---|---|---|---|---|---|---|---|
| | 1819 | 670 | 330 | 198 | 242 | 409 | 141 | 415 | 330 |
| Resistance | HSRZ | HRZ | RSR | H | H | HR | HRT | HRT | HS |
| MIC (μM) | ≤0.02 | 0.04 | 0.04 | 0.08 | 0.08 | 0.08 | 0.08 | 0.08 | 0.08 |
| | Strain | | | | | | | | |
| | 175 | 709 | 732 | 201 | 202 | 277 | 605 | 123 | 106 |
| Resistance | S | S | S | HRE | S | H | HSERZACp | HSERZKTACp | HR |
| MIC (μM) | 0.08 | 0.08 | 0.08 | 0.08 | 0.08 | 0.08 | 0.16 | 0.16 | 0.16 |
| | Strain | | | | | | | | |
| | 562 | 139 | 514 | 1672 | 167 | 254 | 297 | 192 | CR |
| Resistance | HSERZKTA | HSERZKTACp | HSRT | HSRZ | HSRZ | H | HSR | HS | HSERZ |
| MIC (μM) | 0.08 | 0.08 | 0.08 | 0.08 | 0.08 | 0.16 | 0.16 | 0.31 | 0.31 |

Figure 3:
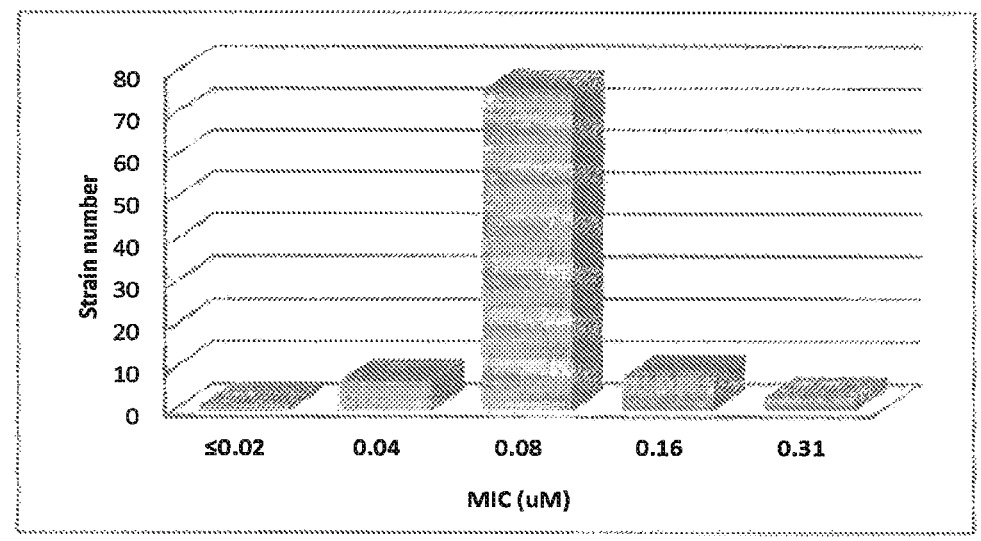
FIG. 3 is a graph of MIC values (from Tables 1A and 1B) for Example 4 G4-Cl against clinical isolates of *M. tuberculosis*.

FIG. 3 Provides a Graphical Representation of the MIC Data in Tables 1A and 1B for Example 4 G4-Cl, Plotted as Number of Strains with a Particular MIC Value (y) Versus the Particular MIC Value Obtained (x) in μM.

As can be seen in FIG. 3, G4-Cl (Example 4) exhibited a MIC value of less than 1 μM for more than 85 clinical isolate strains of 97 tested (sensitive and resistant), indicating the very good activity of this compound against a significant number of *M. tuberculosis* clinical isolate strains. The breakdown is a measured MIC of ≤0.2 μM for 1 strain; a measured MIC of 0.04 μM for 8 strains; a measured MIC of 0.08 μM for 76 strains; a measured MIC of 0.16 μM for 8 strains; and a measured MIC of 0.31 μM for 3 strains.

Tables 2A and 2B Provide MIC Values for Example 4 G4-Cl Tested Against M. tuberculosis Sensitive (A) and Resistant (B) Clinical Isolates

A

| Strain | 137 | 169 | 192 | 199 | 206 | 207 | 208 | 223 | 231 | 237 | 247 | 248 |
|---|---|---|---|---|---|---|---|---|---|---|---|---|
| MIC (µM) | 0.08 | 0.08 | 0.08 | 0.08 | 0.08 | 0.08 | 0.08 | 0.08 | 0.08 | 0.08 | 0.08 | 0.08 |
| Strain | 249 | 255 | 261 | 265 | 269 | 281 | 292 | 314 | 316 | 317 | 322 | 323 |
| MIC (µM) | 0.08 | 0.08 | 0.08 | 0.08 | 0.08 | 0.08 | 0.08 | 0.08 | 0.08 | 0.08 | 0.08 | 0.08 |
| Strain | 324 | 326 | 327 | 328 | 329 | 332 | 333 | 358 | | | | |
| MIC (µM) | 0.08 | 0.08 | 0.08 | 0.08 | 0.08 | 0.08 | 0.08 | 0.08 | | | | |

B

| Strain | 175 | 198 | 242 | 330 | 141 |
|---|---|---|---|---|---|
| Resistance | S | H | H | HSR | HRT |
| MIC (µM) | 0.08 | 0.08 | 0.08 | 0.08 | 0.08 |
| Strain | 1819 | 1672 | 167 | 139 | 123 |
| Resistance | HSRZ | HSRZ | HSRZ | HSERZKTACp | HSERZKTACp |
| MIC (µM) | 0.02 | 0.08 | 0.08 | 0.08 | 0.16 |

Tables 2C and 2D Provide MIC Values for Example 2 G2-Br Tested Against the Same M. tuberculosis Sensitive (A) and Resistant (B) Clinical Isolates

C

| Strain | 137 | 169 | 192 | 199 | 206 | 207 | 208 | 223 | 231 | 237 | 247 | 248 |
|---|---|---|---|---|---|---|---|---|---|---|---|---|
| MIC (µM) | 0.08 | 0.08 | 0.08 | 0.08 | 0.08 | 0.08 | 0.08 | 0.08 | 0.08 | 0.08 | 0.08 | 0.08 |
| Strain | 249 | 255 | 261 | 265 | 269 | 281 | 292 | 314 | 316 | 317 | 322 | 323 |
| MIC (µM) | 0.08 | 0.08 | 0.08 | 0.08 | 0.08 | 0.08 | 0.08 | 0.08 | 0.08 | 0.08 | 0.08 | 0.08 |
| Strain | 324 | 326 | 327 | 328 | 329 | 332 | 333 | 358 | | | | |
| MIC (µM) | 0.08 | 0.08 | 0.08 | 0.08 | 0.08 | 0.08 | 0.08 | 0.08 | | | | |

D

| Strain | 175 | 198 | 242 | 330 | 141 |
|---|---|---|---|---|---|
| Resistance | S | H | H | HSR | HRT |
| MIC (µM) | 0.08 | 0.08 | 0.08 | 0.08 | 0.08 |
| Strain | 1819 | 1672 | 167 | 139 | 123 |
| Resistance | HSRZ | HSRZ | HSRZ | HSERZKTACp | HSERZKTACp |
| MIC (µM) | 0.04 | 0.08 | 0.08 | 0.08 | 0.08 |

Figure 4:
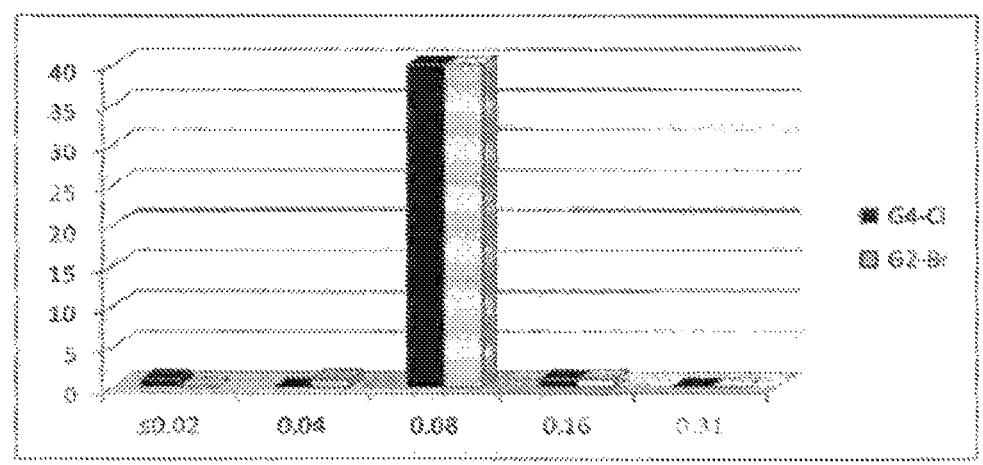
FIG. 4 is a graph of MIC values (from Tables 2A, 2B, 2C and 2D) for Example 2 and Example 4 (G2-Br and G4-Cl, respectively) against clinical isolates of *M. tuberculosis*.

FIG. 4 Provides a Graphical Representation of the MIC Data in Tables 2A Through 2D for G2-Br (Example 2—Light Bar) and G4-Cl (Example 4—Dark Bar), Plotted as Number of Strains with a Particular MIC Value (y) Versus the Particular MIC Value Obtained (x), in µM.

As can be seen in FIG. 4, G4-Cl (Example 4) and G2-Br (Example 2) exhibited a MIC value of less than 1 µM for all of but 1 of the 40 M. tuberculosis clinical isolate strains tested in this experiment. The breakdown is a measured MIC of ≤0.2 µM for 1 strain (EXAMPLE 4); a measured MIC of 0.04 µM for 1 strain (EXAMPLE 2); a measured MIC of 0.08 µM for 40 strains (EXAMPLE 2 and EXAMPLE 4); a measured MIC of 0.16 µM for 1 strain (EXAMPLE 2 and EXAMPLE 4); and no measured MIC of 0.31 µM for EXAMPLE 2 or EXAMPLE 4 for any strain.

Example 20

General Antimicrobial Activity Assay

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically".

Table 3 provides MIC values against bacterial strains K12; E. coli K12 tolC/Tn10; A. baumannii ATCC 17978; and P. aeruginosa PA01 for compounds disclosed in the Examples. As can be seen, the Example compounds do not generally possess significant activity across several pathogenic Gram negative bacteria, as well as an efflux pump deficient E. coli. But as shown in Table 4 below, the compounds disclosed in the Examples do possess significant activity against M. tuberculosis. Moreover, as can be seen, tricyclic comparator benzoxaboroles lacking a 4-halogen (eg C2-H, C5-H and C12-H) have greater activity against these bacterial strains whereas tricyclic benzoxaborole compounds with the third ring being a seven-membered ring between the 1 and 7 positions of the benzoxaborole, additionally having 4-halo, 3-aminomethyl substitution with (S) stereochemistry at the 3 position (eg G2-Br and G4-Cl) have very poor activity against these bacteria. This is in marked contrast to their respective activities against M. tuberculosis, where the 4-halo compounds generally display very good activity but the tricyclic benzoxaboroles without a 4-halogen are poorer (compare the M. tuberculosis MIC values for the same set of compounds in Tables 4A and 4B).

Table 3 Provides MIC Values Against Non-Mycobacterial Strains for Compounds of Formula II or Formula IIa

| Compound | MIC: E. coli K12 [ug/mL] | MIC: E. coli K12 tolC::Tn10 [ug/mL] | MIC: A. baumannii ATCC 17978 [ug/mL] | MIC: P. aeruginosa PA01 [ug/mL] |
|---|---|---|---|---|
| Example 1 G1-Br | >64 | >64 | >64 | >64 |
| Example 2 G2-Br | 64 | 64 | 64 | 64 |
| Example 3 G3-Cl | >64 | >64 | >64 | >64 |
| Example 4 G4-Cl | 64 | 64 | 64 | 64 |
| Example 5 G5-F | 32 | 64 | >64 | 4 |
| Example 6 G6-I | — | — | — | — |
| Example 7 G7-Cl | >64 | >64 | >64 | >64 |

-continued

| Compound | MIC: E. coli K12 [ug/mL] | MIC: E. coli K12 tolC::Tn10 [ug/mL] | MIC: A. baumannii ATCC 17978 [ug/mL] | MIC: P. aeruginosa PA01 [ug/mL] |
|---|---|---|---|---|
| Example 8 G8-Br | >64 | >64 | >64 | >64 |
| Example 9 G9-Br | >64 | >64 | >64 | >64 |
| Example 10 G10-Br | >64 | >64 | >64 | >64 |
| Example 11 G11-Cl | >64 | >64 | >64 | >64 |
| Example 12 G12-Cl | >64 | >64 | >64 | >64 |
| C1-H | — | — | — | — |
| C2-H | 2 | 4 | 2 | 2 |
| C3-H | — | — | — | — |
| C4-Br | 64 | 64 | 64 | 64 |
| C5-H | — | — | — | — |
| C6-Cl | 64 | 64 | 64 | 64 |
| C7-Cl2 | — | — | — | — |
| C8-Cl | — | — | — | — |
| C9-Cl | — | — | — | — |
| C10-H | — | — | — | — |
| C11-H | 2 | 2 | 4 | 2 |
| C12-H | 4 | 2 | 4 | 16 |
| C13-Cl | — | — | — | — |
| C14-Cl2 | — | — | — | — |
| C15-F | — | — | — | — |
| C16-Cl GSK3309930A AN12471.01 | — | — | — | — |
| C17-Cl GSK3309934A AN12470.01 | — | — | — | — |
| C18-Br GSK3337512A AN12344.01 | — | — | — | — |
| C19-Br GSK3309932A AN12343.01 | — | — | — | — |

Example 21

LeuRS Expression and Purification

For biochemical analyses an N-terminal six histidine-tagged LeuRS was over-expressed in *Escherichia coli* which were *E. coli* codon-optimised (GenScript, Piscataway N.J., USA), from human mitochondria and cytoplasm, and *M. tuberculosis*. N-terminal six histidine-tagged LeuRS proteins were over-expressed and purified according to Novagen (Madison, Wis., USA) using an *E. coli* BL21(DE3) T7 RNA polymerase over-expression strain.

Example 22

Aminoacylation Assay

Experiments were performed in 96-well microtiter plates, using 80 μL reaction mixtures containing 50 mM HEPES-KOH (pH 8.0), 30 mM $MgCl_2$ 30 mM KCl, 13 μM L-[$^{14}$C] leucine (306 mCi/mmol, Perkin-Elmer), 15 uM total *E. coli* tRNA (Roche, Switzerland), 0.02% (w/v) BSA, 1 mM DTT, 0.2 μM LeuRS and 4 mM ATP at 30° C. Reactions were started by the addition of 4 mM ATP. After 7 minutes, reactions were quenched and tRNA was precipitated by the addition of 50 μL of 10% (w/v) TCA and transferred to 96-well nitrocellulose membrane filter plates (Millipore Multiscreen HTS, MSHAN4B50). Each well was then washed three times with 100 μL of 5% TCA. Filter plates were then dried under a heat lamp and the precipitated L-[$^{14}$C]leucine tRNALeu were quantified by liquid scintillation counting using a Wallac MicroBeta Trilux model 1450 liquid scintillation counter (PerkinElmer, Waltham, Mass., USA). The only difference was with the human cytoplasmic LeuRS when we used tRNA isolated from Brewer's Yeast (Roche Diagnostics GmbH).

Example 23

$IC_{50}$ Determination

To determine the inhibitor concentration, which reduces enzyme activity by 50% ($IC_{50}$), increasing concentrations of compound (Anacor Pharmaceuticals Inc., Palo Alto, CA, USA) were incubated with LeuRS enzyme, tRNA and L-leucine 20 minutes. Reactions were initiated by the addition of 4 mM ATP. Reactions were stopped after 7 minutes then precipitated and counted to quantify radioactivity. IC50 values were determined using the Graphpad Prism software package (Graphpad Software Inc. (La Jolla, Calif., USA).

Example 24

HepG2 Cytotoxicity Assay

HepG2 cells (HB-8065) were fed fresh medium (Essential Minimum Eagle Medium, EMEM, supplemented with 5% fetal calf serum and 2 mM L-glutamine) the day before subculturing the plates. On the day of plate seeding, a cell suspension of 100,000 cells/mL in culture medium was prepared. Cell suspension (100 uL) was added in each well of a black 96-well microplate with clear bottom, collagen coated, (Becton Dickinson) except in column 11, that was dispensed only 100 uL of culture medium. The plates were incubated for 24 h. It was made up a range of 10 doses of test substances by preparing serial dilutions 1:2 from the stock solution in 100% DMSO and made a dilution of 1:200 of each dose in medium, to achieve a final concentration of 0.5% of DMSO. After 24 h, culture medium was removed from the plate and 150 uL of test compound dilutions were added in two replicates and 150 uL of 0.5% DMSO in culture medium to columns 11 and 12 (blank control). Plates were incubated for 48 and at 37° C., 5% CO2, 95% relative humidity. The medium was then removed and 200 uL of fresh culture medium was added and 50 uL of Resazurin solution to each well and incubated for 1 h and a half. Plates were removed from incubator to allow the fluorescence to stabilise at room temperature protected from light for 15 min. For read out of viability of cells we used Resazurine (BDH). Resazurin is used as an oxidation-reduction indicator that yields a colorimetric change and a fluorescent signal in response to metabolic activity. As cell grows, metabolic activity results in a chemical reduction of Resazurin indicated by a change from non-fluorescent blue to the reduced fluorescent pink form. The degree of Resazurin fluorescence is therefore, an indicator of the number of viable cells in the culture system. Fluorescence was measured at an excitation wavelength of 515 nm and an emission wavelength of 590 nm in a Microplate reader1420 Multilabel HTS counter, Victor 2, (Wallac).

The fluorescence value of each well is corrected by subtracting the background value (average of column 11) from the absolute value. The percentages of inhibition are calculated relatively to the DMSO control wells (average of column 12). For each compound, the average value of the duplicate samples is calculated and the curve is fitted to Sigmoidal dose-response (variable slope) nonlinear regression curve adjustment (GraphPad) in order to calculate the IC50 (Tox50).

Example 25

The Effect of Compounds Described Herein Against *Mycobacterium tuberculosis*

Compounds of the present invention were tested for antibacterial activity against a *Mycobacterium tuberculosis* species and also tested for human liver cell toxicity using HepG2 cells. Exemplary compounds of the invention were compared to comparator compounds C1-H through C19-Br, as shown in Tables 4A and 4B.

Table 4A provides LeuRS inhibition IC50 values, MIC values against the *M. tuberculosis* standard strain Mtb H37Rv, toxicity values against human HepG2 cells, and selectivity values for Certain Comparator Tricyclic Benzoxaborole Compounds

| Compound Designation | Compound Structure | Mtb LeuRS $IC_{50}$ (uM) | Human cyto LeuRS $IC_{50}$ (μM) | Human mito LeuRS $IC_{50}$ (μM) | Mtb H37Rv MIC (μM) (B) | HepG2 cell 48 h Tox50 (μM) (A) | Selectivity Index (A/B) |
|---|---|---|---|---|---|---|---|
| C1-H | 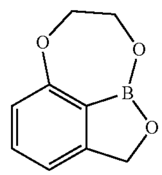 [SMILES: c1cc2c3c(c1)OCCOB3OC2] | 12.2 | 101 | — | 31 | — | — |
| C2-H (racemic) | 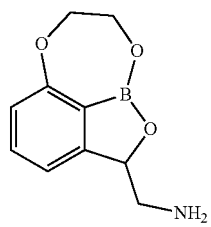 [SMILES: NCC1OB2OCCOc3cccc1c32] | 0.506 | 272 | >300 | 188 | >50 | >26 |
| C3-H | 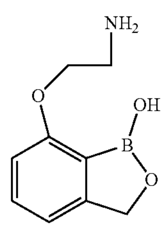 [SMILES: NCCOc1cccc2c1B(O)OC2] | 17.6 | 35.7 | — | 62 | >50 | >0.8 |
| C4-Br | 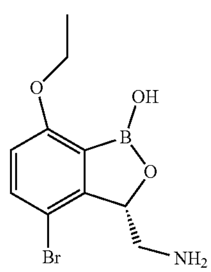 [SMILES: CCOc1ccc(Br)c2c1B(O)O[C@@H]2CN] | 0.07 | 31, (73, 67) | >300 | 0.1 | 32 | 320 |
| C5-H | 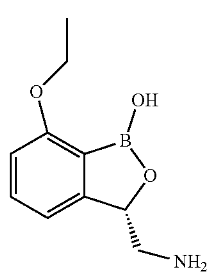 | 0.111 | 25.6 | >300 | 0.6 | 1.8 | 3 |

-continued

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| C6-Cl | 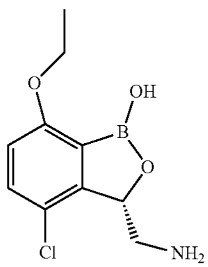 [SMILES: CCOc1ccc(Cl)c2c1B(O)O[C@@H]2CN] | 0.05 | 38.8 | >300 | 0.1 | 36.3 | 363 |
| C7-Cl$_2$ | 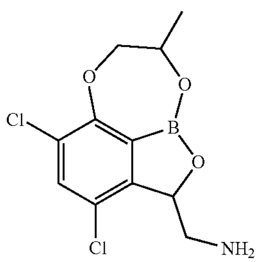 [SMILES: CC1COc2c(Cl)cc(Cl)c3c2B(O1)OC3CN] | 7.97 | — | — | 2.5 | >50 | >20 |
| C8-Cl | 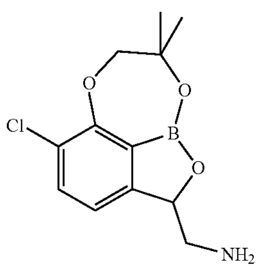 [SMILES: CC1(C)COc2c(Cl)ccc3c2B(OC3CN)O1] | 6.05 | — | — | >5.0 | >50 | 10 |
| C9-Cl | 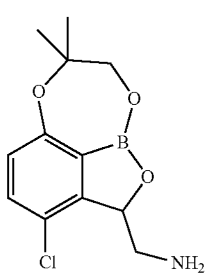 [SMILES: CC1(C)COB2OC(CN)c3c(Cl)ccc(c32)O1] | 37.59 | — | — | 5.0 | >50 | >10 |
| C10-H | 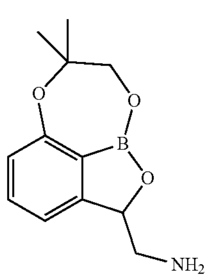 [SMILES: CC1(C)COB2OC(CN)c3cccc(c32)O1] | >300 | — | — | >5.0 | >50 | 10 |

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| C11-H | 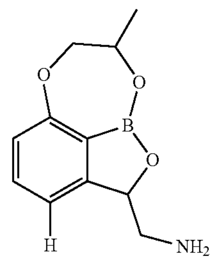 [SMILES: CC1COc2cccc3c2B(O1)OC3CN] | 0.51 | — | — | 1.56 | >50 (40%) | >32 |
| C12-H | 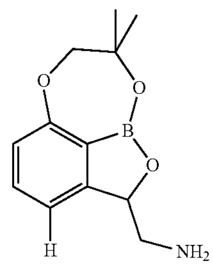 [SMILES: CC1(C)COc2cccc3c2B(OC3CN)O1] | 1.33 | — | — | >5.0 | 24.5 | >4.9 |
| C13-Cl | 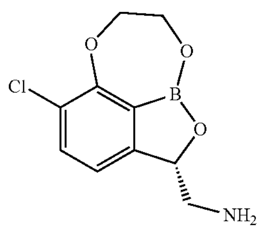 [SMILES: NC[C@H]1OB2OCCOc3c(Cl)ccc1c32] | 2.16 | | | 5.0 | >50 | >10 |
| C14-Cl$_2$ | 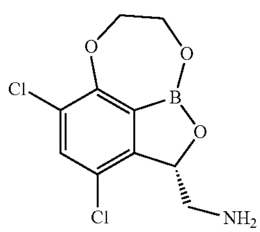 [SMILES: NC[C@H]1OB2OCCOc3c(Cl)cc(Cl)c1c32] | 4.67 | | | >5.0 | >50 | >10 |
| EXAMPLE 13 C15-F ((2S,8R)-2-(aminomethyl)-3-fluoro-7,8-dihydro-2H-1,6,9-trioxa-9a-borabenzo[cd]azulen-8-yl)methanol | 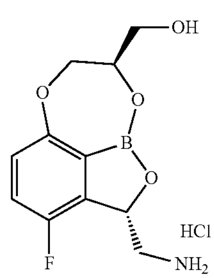 [SMILES: NC[C@H]1OB2O[C@H](CO)COc3ccc(F)c1c32 ; Cl] | 0.48 | — | — | 0.55 | >50 | >10 |
| EXAMPLE 14 C16-Cl ((8R)-2-(aminomethyl)-3-chloro-8-methyl-7,8-dihydro-2H-1,6,9-trioxa-9a-borabenzo[cd]azulen-8-yl)methanol | 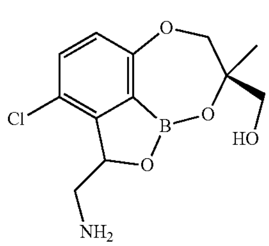 [SMILES: C[C@@]1(CO)COc2ccc(Cl)c3c2B(OC3CN)O1] | 4.17 | — | — | 1.25 | >50 | >4 |

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| EXAMPLE 15 C17-Cl ((8S)-2-(aminomethyl)-3-chloro-8-methyl-7,8-dihydro-2H-1,6,9-trioxa-9a-borabenzo[cd]azulen-8-yl)methanol | 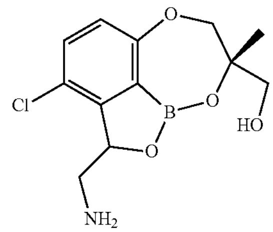 [SMILES: C[C@]1(CO)COc2ccc(Cl)c3c2B(OC3CN)O1] | 3.13 | — | — | 0.93 | >50 | >50 |
| EXAMPLE 16 C18-Br ((8R)-2-(aminomethyl)-3-bromo-8-methyl-7,8-dihydro-2H-1,6,9-trioxa-9a-borabenzo[cd]azulen-8-yl)methanol | 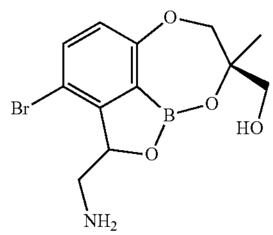 [SMILES: C[C@@]1(CO)COc2ccc(Br)c3c2B(OC3CN)O1] | 2.69 | — | — | 1.25 | >50 | >40 |
| EXAMPLE 17 C19-Br ((8S)-2-(aminomethyl)-3-bromo-8-methyl-7,8-dihydro-2H-1,6,9-trioxa-9a-borabenzo[cd]azulen-8-yl)methanol | 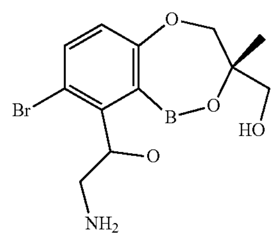 | 1.97 | — | — | 0.925 | >50 | >50 |

Table 4B provides LeuRS inhibition IC50 values, MIC values against the *M. tuberculosis* standard strain Mtb H37Rv, toxicity values against human HepG2 cells, and selectivity values for Compounds of Formula II or Formula IIa

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| EXAMPLE 1 G1-Br | 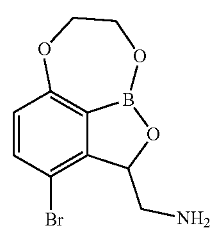 [SMILES: NCC1OB2OCCOc3ccc(Br)c1c32] | 0.154 | | | 0.18 | >50 | >277 |

-continued

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| EXAMPLE 2 G2-Br | 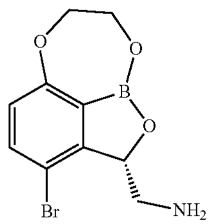 [SMILES: NC[C@H]1OB2OCCOc3ccc(Br)c1c32] | 0.115 | 118 | >300 | 0.07 | 292.4 | 4177 |
| EXAMPLE 3 G3-Cl | 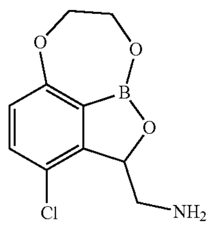 | 0.244 | | | 0.47 | >50 | >106 |
| EXAMPLE 4 G4-Cl | 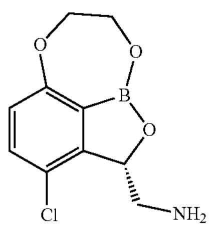 | 0.148 | 94.7 | >300 | 0.08 | >1000 | >12500 |
| EXAMPLE 5 G5-F | 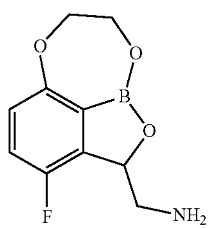 [SMILES: NCC1OB2OCCOc3ccc(F)c1c32] | 0.46 | | | 0.6 | 49.1 | 164 |
| EXAMPLE 6 G6-I | 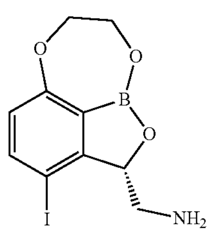 [SMILES: NC[C@H]1OB2OCCOc3ccc(I)c1c32] | 0.33 | | | 0.3 | 36.4 | 121 |
| EXAMPLE 7 G7-Cl | 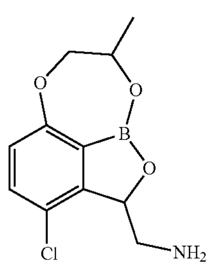 | 1.08 | >300 | — | 0.20 | >50 | >250 |

-continued

| Compound Designation | Compound Structure | Mtb LeuRS IC$_{50}$ (uM) | Human cyto LeuRS IC$_{50}$ (μM) | Human mito LeuRS IC$_{50}$ (μM) | Mtb H37Rv MIC (μM) (B) | HepG2 cell 48 h Tox50 (μM) (A) | Selectivity Index (A/B) |
|---|---|---|---|---|---|---|---|
| EXAMPLE 8 G8-Br | 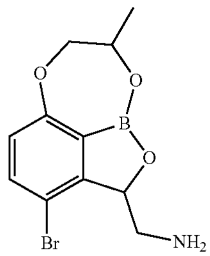 [SMILES: CC1COc2ccc(Cl)c3c2B(O1)OC3CN] | 1.43 | >300 | — | 0.30 | >50 | >167 |
| EXAMPLE 9 G9-Br | 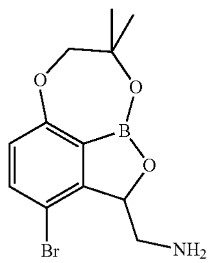 | 1.25 | >300 | — | 0.30 | >50 | >167 |
| EXAMPLE 10 G10-Br | 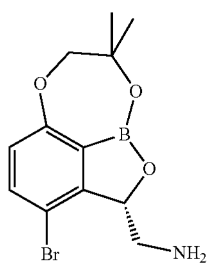 [SMILES: CC1(C)COc2ccc(Br)c3c2B(O[C@@H]3CN)O1] | 1.13 | >300 | | 0.16 | 460 | 2875 |
| EXAMPLE 11 G11-Cl | 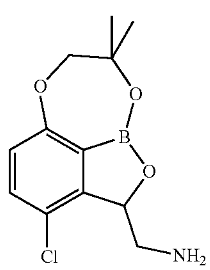 [SMILES: CC1(C)COc2ccc(Cl)c3c2B(OC3CN)O1] | 0.68 | >300 | — | 0.27 | >50 | >185 |
| EXAMPLE 12 G25-Cl | 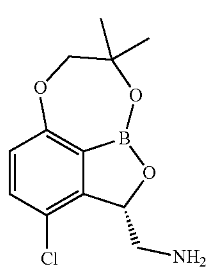 [SMILES: CC1(C)COc2ccc(Cl)c3c2B(O[C@@H]3CN)O1] | 0.78 | >300 | | 0.08 | 322 | 4025 |

As can be seen in Table 4B, for Examples 2, 4, 10 and 12 (G2-Br, G4-Cl, G10-Br and G12-Cl) there appears to be increased selectivity for inhibiting growth of *M. tuberculosis* versus toxicity for human HepG2 cells for a tricyclic benzoxaborole compound with the third ring being a seven-membered ring between the 1 and 7 positions of the benzoxaborole, additionally having 4-halo, 3-aminomethyl substitution with (S) stereochemistry at the 3 position.

Tables 4A and 4B show a comparison of certain tricyclic benzoxaborole compounds with and without halogen substitution, certain tricyclic benzoxaborole compounds with and without halogen substitution at position 4 of the benzoxaborole ring structure, and certain bicyclic compounds. From the Mtb H37Rv MIC values (B), and the HepG2 cell 48 h Tox$_{50}$ values (A), it is possible to determine selectivity for inhibition of *M. tuberculosis* versus inhibition (toxicity) of human cells for these compounds (see far right column of Tables 4A and 4B).

Compounds Example 2 G2-Br and Example 4 G4-Cl were found to have selectivity indices against *M. tuberculosis* of 4177 and >12,500, respectively (see Table 4B). Further, as seen in Table 4B the IC$_{50}$ values for these compounds against *M. tuberculosis* were found to be sub-micromolar, at 0.13 and 0.1, respectively. As can be seen, the selectivity index (SI) of Example 2 G2-Br and Example 4 G4-Cl against *M. tuberculosis* is unexpectedly improved over other benzoxaborole compounds. Example 2 G2-Br and Example 4 G4-Cl, which are tricyclic benzoxaborole compounds having a halogen substituent at the C-4 position of the benzoxaborole ring and an aminomethyl substituent at position C3 of the benzoxaborole ring having "(S)" relative stereochemistry at that stereocenter, are surprisingly more selective for activity against *M. tuberculosis* than other benzoxaborole compounds lacking some of these features versus inhibition (toxicity) of human cells for these compounds. In addition, the MIC values against *M. tuberculosis* H37Rv strain for Example. 2 G2-Br and Example 4 G4-Cl are both <0.1 µM in contrast to other benzoxaborole compounds in this study.

Thus, as seen in Table 4B, compounds Example 2 G2-Br and Example 4 G4-Cl were found to have a SI against *Mycobacterium tuberculosis* of 4177 (Example 2 G2-Br) and >12,500 (Example 4 G4-Cl), respectively. These SI values are surprisingly better than any of the comparator compounds tested to date.

Addition of a chloro or bromo substituent at C4 of the benzoxaborole ring confers an unexpected increase in the selectivity index. C2-H (racemic; no halogen substituent at C4 of the benzoxaborole ring) has a selectivity index of >26 whereas Example 1 G1-Br (racemic; bromo substituent at C-4 of the benzoxaborole ring) has an SI of >277. Similarly, Example 3 G3-Cl (racemic; chloro substituent at C-4 of the benzoxaborole ring) has an SI of >106 compared to C2-H with an SI of >26.

Formation of a third ring involving the 1 and 7 positions of the benzoxaborole ring confers an unexpected increase in the selectivity index. C4-Br, the (S) enantiomer of a non-tricyclic benzoxaborole comparator compound with a Br at the C4 position of the benzoxaborole ring, has an SI of 320, whereas Example 2 G2-Br, the (S) enantiomer of a tricyclic benzoxaborole with a Br at the C-4 position, has an SI of 4177. Similarly, C6-Cl, the (S) enantiomer of a non-tricyclic benzoxaborole comparator compound with a Cl at the C4 position of the benzoxaborole ring, has an SI of 363, whereas Example 4 G4-Cl, the (S) enantiomer of a tricyclic benzoxaborole with a Cl at the C-4 position, has an SI of >12,500.

If one compares the SI of Example 2 G2-Br and Example 4 G4-Cl to the SI of C5-H, the (S) enantiomer of a non-tricyclic benzoxaborole comparator compound with a H at the C4 position of the benzoxaborole ring, one can see the SI of such a compound without a halogen substituent at C4 is only 3, indicating such a compound has very little selectivity for inhibiting *M. tuberculosis* compared to killing human cells.

Certain substitutions of the 7-membered tricyclic ring confer an unexpected increase in the selectivity index. Table 4B shows Example 9 G9-Br and Example 11 G11-Cl with SI indices of >167 and >185, respectively, whereas comparator compounds C9-Cl (a tricyclic benzoxaborole with a chloro substituent at C4 and —CH$_3$ substitution at R$^3$ and R$^4$ of the 7-membered ring) and C10-H (a tricyclic benzoxaborole with a hydrogen at C4 and —CH$_3$ substitution at R$^3$ and R$^4$ of the 7-membered ring) have SI indices of 10. This arguably indicates that substitution at the R$^3$ and R$^4$ positions is not favored for selectivity for *M. tuberculosis* versus inhibition (toxicity) of human cells for these compounds. It also suggests that the presence of a halogen at position C4 of the benzoxaborole ring (see C9-Cl) is not sufficient to overcome the negative effect of methyl substitution at both R$^3$ and R$^4$ of the 7-membered tricyclic ring at the R$^3$/R$^4$ position.

In other respects Example 2 G2-Br and Example 4 G4-Cl also have SI values unexpectedly higher than related open ring benzoxaboroles (substituted benzoxaboroles) lacking a halogen substituent at the C4 position of the benzoxaborole ring. Compare the SI for C5-H (5) to the SIs for Example 2 G2-Br and Example 4 G4-Cl. Benzoxaboroles that are not tricyclic benzoxaboroles but which have a halogen at the C4 position of the benzoxaborole ring show improved SIs relative to no halogen, but still exhibit SI values significantly lower than the SIs for Example 2 G2-Br and Example 4 G4-Cl (compare C5-H to C3-Br and C6-Cl; but then compare all three C5-H, C3-Br and C6-Cl to the SI values of Example 2 G2-Br and Example 4 G4-Cl).

Thus, the tricyclic benzoxaboroles of the invention, particularly Example 2 G2-Br and Example 4 G4-Cl, show surprisingly higher SIs relative to the SIs of related benzoxaboroles for *M. tuberculosis* versus human cells.

It is to be understood that the invention covers all combinations of aspects with all other suitable aspects and/or exemplary embodiments described herein. It is to be understood that the invention also covers all combinations of exemplary embodiments with all other suitable aspects and/or exemplary embodiments described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a disease resulting from a mycobacterial infection in an animal, the method comprising:
  administering to the animal in need of such treatment a combination comprising
    a first therapeutic agent which is (S)-(3-chloro-7,8-dihydro-2H -1,6,9-trioxa-9a-borabenzo[cd]azulen-2-yl)methanamine or a pharmaceutically acceptable salt thereof, and
    a second therapeutic agent which is not the first therapeutic agent.

2. The method according to claim 1, wherein the first therapeutic agent is ((S)-(3-chloro-7,8-dihydro-2H-1,6,9-trioxa-9a        -borabenzo[cd]azulen-2-yl)methanamine dihydrogensulfate.H$_2$O.

3. The method according to claim 1, wherein the second therapeutic agent is independently selected from isoniazid, rifampin, pyrazinamide, ethambutol, moxifloxacin, rifapentine, clofazimine, bedaquiline (TMC207), nitroimidazo-oxazine PA-824, delamanid (OPC-67683), an oxazolidinone, EMB analogue SQ109, a benzothiazinone, and a dinitrobenzamide.

4. The method according to claim 3, wherein the oxazolidinone is linezolid, tedizolid, radezolid, sutezolid (PNU-100480), or posizolid (AZD-5847).

5. The method according to claim 1, wherein the second therapeutic agent is an antiviral agent.

6. The method according to claim 5, wherein the antiviral agent is an antiretroviral agent.

7. The method according to claim 6, wherein the antiretroviral agent is zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

8. The method according to claim 1, wherein the combination includes a pharmaceutically acceptable excipient, adjuvant, or diluent.

9. The method according to claim 1, wherein the second therapeutic agent is a therapeutic agent approved or recommended for the treatment of tuberculosis.

10. The method according to claim 1, wherein the mycobacterial infection is an infection of a mycobacterium selected *Mycobacterium tuberculosis, Mycobacterium avium, Mycobacterium kansasii, Mycobacterium malmoense, Mycobacterium simiae, Mycobacterium szulgai, Mycobacterium xenopi, Mycobacterium scrofulaceum, Mycobacterium abscessus, Mycobacterium chelonae, Mycobacterium haemophilum, Mycobacterium leprae, Mycobacterium marinum, Mycobacterium fortuitum, Mycobacterium parafortuitum, Mycobacterium gordonae, Mycobacterium vaccae, Mycobacterium bovis, Mycobacterium bovis* BCG, *Mycobacterium africanum, Mycobacterium canetti, Mycobacterium caprae, Mycobacterium microti, Mycobacterium pinnipedi, Mycobacterium leprae, Mycobacterium ulcerans, Mycobacterium intracellulare, Mycobacterium avium* complex (MAC), *Mycobacterium avian*-intracellulare complex (MAIC), *Mycobacterium gordonae* clade; *Mycobacterium kansasii* clade; *Mycobacterium chelonae* clade; *Mycobacterium fortuitum* clade; *Mycobacterium parafortuitum* clade; and *Mycobacterium vaccae* clade.

11. The method according to claim 10, wherein the mycobacterium is *Mycobacterium avium*.

12. The method according to claim 10, wherein the mycobacterium is *Mycobacterium abscessus*.

13. The method according to claim , wherein the disease is tuberculosis.

14. The method according to claim 1, wherein the disease is selected from Johne's disease, Crohn's disease, Lady Windermere syndrome, *Mycobacterium avium* complex (MAC) lung disease, disseminated *Mycobacterium avium* complex (DMAC), disseminated *Mycobacterium avium intraceullulare* complex (DMAIC), hot-tub lung, MAC mastitis, MAC pyomyositis, *Mycobacterium avium* paratuberculosis, or granuloma disease.

15. The method according to claim 1, wherein the animal is a mammal.

16. The method according to claim 1, wherein the animal is a human.

17. The method according to claim 10, wherein *Mycobacterium avium* comprises subspecies (subsp.) *Mycobacterium avium* subsp. *avium, Mycobacterium avium* subsp. *hominissuis, Mycobacterium avium* subsp. *silvaticum*, or *Mycobacterium avium* subsp. *paratuberculosis*.

18. The method according to claim 1, wherein the disease is a pulmonary disease or a pulmonary infection.

* * * * *